(12) United States Patent
Lofton-Day et al.

(10) Patent No.: US 7,943,308 B2
(45) Date of Patent: May 17, 2011

(54) METHODS AND NUCLEIC ACIDS FOR THE DETECTION OF METASTASIS OF COLON CELL PROLIFERATIVE DISORDERS

(75) Inventors: Catherine Lofton-Day, Seattle, WA (US); Matthias Ebert, Munich (DE)

(73) Assignee: Epigenomics AG, Berlin (DE)

( * ) Notice: Subject to any disclaimer, the term of this patent is extended or adjusted under 35 U.S.C. 154(b) by 702 days.

(21) Appl. No.: 11/630,620

(22) PCT Filed: Jun. 23, 2005

(86) PCT No.: PCT/US2005/022391
§ 371 (c)(1),
(2), (4) Date: Dec. 7, 2007

(87) PCT Pub. No.: WO2006/002344
PCT Pub. Date: Jan. 5, 2006

(65) Prior Publication Data
US 2010/0035242 A1    Feb. 11, 2010

Related U.S. Application Data

(60) Provisional application No. 60/582,675, filed on Jun. 23, 2004.

(51) Int. Cl.
*C12Q 1/68*    (2006.01)
(52) U.S. Cl. .......................................................... 435/6
(58) Field of Classification Search .......................... None
See application file for complete search history.

(56) References Cited

U.S. PATENT DOCUMENTS

| | | | |
|---|---|---|---|
| 5,474,796 A * | 12/1995 | Brennan | 427/2.13 |
| 5,565,552 A | 10/1996 | Magda et al. | |
| 5,567,810 A | 10/1996 | Weis et al. | |
| 5,574,142 A | 11/1996 | Meyer, Jr. et al. | |
| 5,585,481 A | 12/1996 | Arnold, Jr. et al. | |
| 5,587,371 A | 12/1996 | Sessler et al. | |
| 5,597,696 A | 1/1997 | Linn et al. | |
| 5,786,146 A | 7/1998 | Herman et al. | |
| 5,958,773 A | 9/1999 | Monia et al. | |
| 6,251,594 B1 | 6/2001 | Gonzalgo et al. | |
| 6,265,171 B1 | 7/2001 | Herman et al. | |
| 6,331,393 B1 | 12/2001 | Laird et al. | |

FOREIGN PATENT DOCUMENTS

| | | |
|---|---|---|
| WO | WO 95/00669 | 1/1995 |
| WO | WO 95/15373 | 6/1995 |
| WO | WO 97/46705 | 12/1997 |
| WO | WO 99/28498 | 6/1999 |
| WO | WO 00/26401 | 5/2000 |
| WO | WO 03072821 A2 * | 9/2003 |
| WO | WO 2004/020662 | 3/2004 |
| WO | WO 2005/001140 | 1/2005 |

OTHER PUBLICATIONS

Baylin and Bestor ("Altered methylation patterns in cancer cell genomes: cause or consequence?" Cancer Cell. May 2002;1(4):299-305).*

Zhu et al. ("Use of DNA methylation for cancer detection and molecular classification" J Biochem Mol Biol. Mar. 31, 2007;40(2):135-41).*
Jankowski et al. (Am J Gastroenterol. May 2009;104(5):1093-6).*
Sabbioni et al. (Mol Diagn. 2003;7(3-4):201-7).*
Database EMBL, "Sequence 4 from Patent WO 03/014388," Apr. 4, 2003, Database accession No. AX705335.
Database EMBL, "Sequence 38 from Patent WO 2004/020662," Mar. 24, 2004, Database accession No. CQ787188.
Database EMBL, "Sequence 222 from Patent WO 2004/020662," Mar. 24, 2004, Database accession No. CQ787372.
Database EMBL, "Sequence 223 from Patent WO 2004/020662," Mar. 24, 2004, Database accession No. CQ787373.
Database EMBL, "Sequence 240 from Patent WO 2004/020662," Mar. 24, 2004, Database accession No. CQ787390.
Database EMBL, "Sequence 241 from Patent WO 2004/020662," Mar. 24, 2004, Database accession No. CQ787391.
Database EMBL, "Sequence 52 from Patent WO 2004/035803," May 10, 2004, Database accession No. CQ806602.
Bläker te al., "Comparison of Losses of Heterozygosity and Replication Errors in Primary Colorectal Carcinomas and Corresponding Liver Metastases," Journal of Pathology, 1999, pp. 258-262, vol. 188.
Brinck et al., "Methylation of the MLH1 and APC promoter regions correlate with decreased and lost expression of MLH1 and APC in melanoma brain metastases," Study Group: Dermatopathology/Pathology—Research and Practice 200, 2004, pp. 351-354.
Eads et al., "CpG Island Hypermethylation in Human Colorectal Tumors Is Not Associated with DNA Methyltransferase Overexpression," Cancer Research, May 15, 1999, pp. 2302-2306, vol. 59.
Eads et al., "MethyLight: a high-thoughput assay to measure DNA methylation," Nucleic Acids Research, 2000, pp. e32 (i)-(viii), vol. 28, No. 8.
Esteller et al., "Analysis of Adenomatous Polyposis Coli Promoter Methylation in Human Cancer," Cancer Research, Aug. 15, 2001, pp. 4366-4371, vol. 60.
Feil et al., "Methylation analysis on individual chromosomes: improved protocol for bisulphite genomic sequencing," Nucleic Acids Research, 1994, pp. 695-696, vol. 22, No. 4.
Frommer et al., "A genomic sequencing protocol that yields a positive display of 5-methylcytosine residues in individual DNA strands," PNAS, Mar. 1992, pp. 1827-1831, vol. 89.
Gonzalez-Gomez et al., "Promoter methylation status of multiple genes in brain metastases of solid tumors," International Journal of Molecular Medicine, 2004, pp. 93-98, vol. 13.
Gonzalgo et al., "Identification and Characterization of Differentially Methylated Regions of Genomic DNA by Methylation-sensitve Arbitrarily Primed PCR," Cancer Research, Feb. 15, 1997, pp. 594-599, vol. 57.
Gonzalgo et al., Rapid quantitation of methylation differences at specific sites using methylation-sensitive single nucleotide primer extension (Ms-SNuPE), Nucleic Acids Research, 1997, pp. 2529-2531, vol. 25, No. 12.
Grigg et al., "Sequencing 5-Methylcytosine Residues in Genomic DNA," BioEssays, Jun. 1994, pp. 431-436, vol. 16, No. 6.

(Continued)

*Primary Examiner* — Christopher M. Babic
(74) *Attorney, Agent, or Firm* — DLA Piper LLP (US)

(57) ABSTRACT

The invention provides methods, nucleic acids and kits for detecting metastasis of colon cell proliferative disorders. The invention discloses genomic sequences the methylation patterns of which have utility for the improved detection of metastasis of colon cell proliferative disorders, thereby enabling the improved diagnosis and treatment of patients.

16 Claims, 2 Drawing Sheets

OTHER PUBLICATIONS

Gut et al, "DNA and Matrix Assisted Laser Desorption Ionization Mass Spectrometry," Molecular Biology: Current Innovations and Future Trends, 1995, pp. 147-157, Horizon Scientific Press, Wymondham, United Kingdom.

Gut et al., "A procedure for selection DNA alkylation and detection by mass spectrometry," Nucleic Acids Research, 1995, pp. 1367-1373, vol. 23, No. 8.

Heid et al., "Real Time Quantitative PCR," Genome Research, 1996, pp. 986-994, vol. 6.

Herman et al., "Methylation-specific PCR: A novel PCR assay for methylation status of CpG islands," Sep. 1996, pp. 9821-9826, vol. 93.

Hiltunen et al., "Hypermethylation of the APC (Adenomatous Polyposis Coli) Gene Promoter Region in Human Colorectal Carcinoma," International Journal of Cancer, 1997, pp. 644-648, vol. 70.

Karas et al., "Laser Desorption Ionization of Proteins with Molecular Masses Exceeding 10 000 Daltons," Analytical Chemistry, Oct. 15, 1988, pp. 2299-2301, vol. 60, No. 20.

Lin et al., "Promoter CpG methylation of tumor suppressor genes in colorectal cancer and its relationship to clinical features," Oncology Reports, 2004, pp. 341-348, vol. 11.

Martin et al., "Genomic sequencing indicates a correlation between DNA hypomethylation in the 5' region of the pS2 gene and its expression in human breast cancer cell lines," Gene, 1995, pp. 261-265, vol. 157.

Olek et al., "A modified and improved method for bisulphite based cytosine methylation analysis," Nucleic Acids Research, 1996, pp. 5064-5066, vol. 24, No. 24.

Olek et al., "The pre-implantation ontogeny of the H19 methylation imprint," Nature Genetics, Nov. 1997, pp. 275-276, vol. 17.

Rein et al., "Identifying 5-methylcytosine and related modifications in DNA genomes," Nucleic Acids Research, 1998, pp. 2255-2264, vol. 26, No. 10.

Sadri et al., "Rapid analysis of DNA methylation using new restriction enzyme sites created by bisulfite modification," Nucleic Acids Research, 1996, pp. 5058-5059, vol. 24, No. 24.

Sakamoto et al., "Methylation of CpG Loci in 5'-Flanking Region Alters Steady-State Expression of Adenomatous Polyposis Coli Gene in Colon Cancer Cell Lines," Journal of Cellular Biochemistry, 2001, pp. 415-423, vol. 80.

Sanger et al., "DNA sequencing with chain-terminating inhibitors," PNAS, Dec. 1977, pp. 5463-5467, vol. 74, No. 12.

Toyota et al., "Identification of Differentially Methylated Sequences in Colorectal Cancer by Methylated CpG Island Amplification," Cancer Research, May 15, 1999, pp. 2307-2312, vol. 59.

Van Der Krol et al., "Modulation of Eukaryotic Gene Expression by Complementary RNA or DNA Sequences," BioTechniques, Nov.-Dec. 1988, pp. 958-976, vol. 6, No. 10.

Xiong et al., "COBRA: a sensitive and quantitative DNA methylation assay," Nucleic Acids Research, 1997, pp. 2532-2534, vol. 25, No. 12.

Yu et al., "Specific Inhibition of PCR by Non-Extendable Oligonucleotides Using a 5' to 3' Exonuclease-Deficient DNA Polymerase," BioTechniques, Oct. 1997, pp. 714-720, vol. 23.

Zauber et al., "Molecular changes in the Ki-ras and APC genes in primary colorectal carcinoma and synchronous metastases compared with the findings in accompanying adenomas," Molecular Pathology, 2003, pp. 137-140, vol. 56.

Zeschnigk et al., "Imprinted segments in the human genome: different DNA methylation pattersn in the Prader-Willi/Angelman syndrome region as determined by the genomic sequencing method," Human Molecular Genetics, 1997, pp. 387-395, vol. 6, No. 3.

Zeschnigk et al., "A single-tube PCR test for the diagnosis of Angelman and Prader-Willi syndrome based on allelic methylation differences at the SNRPN locus," European Journal of Human Genetics, Mar.-Apr. 1997, pp. 94-98, vol. 5, No. 2.

Zon, "Oligonucleotide Analogues as Potential Chemotherapeutic Agents," Pharmaceutical Research, Sep. 1988, pp. 539-549, vol. 5, No. 9.

* cited by examiner

METHODS AND NUCLEIC ACIDS FOR THE DETECTION OF METASTASIS OF COLON CELL PROLIFERATIVE DISORDERS

CROSS-REFERENCE TO RELATED APPLICATIONS

The application claims the benefit of priority to U.S. Provisional Patent Application Ser. No. 60/582,675, filed 23 Jun. 2004, which is incorporated by reference herein in its entirety.

FIELD OF THE INVENTION

Aspects of this invention relate to cancer and cancer progression and metastasis, and more particularly to colon cancer progression and metastasis and to novel methods and compositions for detection of colon cancer and progression and metastasis thereof.

BACKGROUND

Colorectal cancer is one of the leading causes of cancer-related death throughout the world, it has a high 5-year mortality rate and 50% of the cases are advanced at the time of diagnosis. Advanced colon cancer is often accompanied by metastasis to peritoneum, lymph nodes or other organs. In recent years, a number of genetic and epigenetic alterations including allelic losses on specific chromosomal arms, mutations of oncogenes, tumor suppressor genes and mismatch repair genes, microsatellite instability in coding repeat sequences of target genes and methylation defects in gene promoters have been described in the tumorigenesis of colorectal cancers and a stepwise model of colorectal carcinogenesis has been proposed. However, the molecular mechanisms underlying the progression and the formation of metastasis of colon cancer are still largely unknown.

The adenomatous polyposis coli (APC) tumor suppressor gene, isolated and mapped to chromosomal band 5q21 (3,4), encodes a large 300 kDa protein with multiple cellular functions and interactions, including signal transduction in the Wnt-signalling pathway, mediation of intercellular adhesion, stabilization of the cytoskeleton and possibly regulation of the cell cycle and apoptosis. Germ-line mutations of the APC gene are associated with hereditary familial adenomatous polyposis (FAP), while somatic mutations in APC occur in ~80% of sporadic colorectal tumors and appear very early in colorectal tumor progression.

Mutation is the most common and primary cause of APC inactivation in colorectal tumors.

DNA methylation is a powerful mechanism for the suppression of gene activity. This frequent epigenetic change in cancer involves aberrantly hypermethylated CpG islands in gene promoters, with loss of transcription of these genes.

A significant proportion of tumor-related genes, including well-characterized tumor suppressor genes (p16$^1$, p15, p14, p73), DNA repair genes (hMLH1), and genes related to metastasis and invasion (CDH1, TIMP3, and DAPK) have been demonstrated to be silenced by methylation in a variety of cancers. Recently, hypermethylation of the APC promoter has also been described in a subset of colorectal adenomas and carcinomas and is considered to be an early step in the process of colorectal cancer pathogenesis.

Although genetic and epigenetic changes of the APC gene have been linked to the early development of colorectal cancer in previous studies, its role in colon cancer metastasis is still largely unknown. Blaker et al. compared the loss of heterozygosity (LOH) pattern of 5q in 15 cases of primary colorectal cancer and the corresponding metastatic liver tumours, and found that the LOH patterns of 5q in the primary and the metastatic tumours were identical in eight cases (Blaker, H., Graf, M., Rieker, R. J., Otto, H. F., Comparison of losses of heterozygosity and replication errors in primary colorectal carcinomas and corresponding liver metastases. J. Pathol., 188,258-262, 1999.). n a recent study, Zauber et al. reported that in their series of 42 colorectal cancers LOH at the APC locus was identical for 39 paired carcinomas and synchronous metastases (Zauber, P., Sabbath-Solitare, M., Marotta, S. P., Bishop, D. T., Molecular changes in the Ki-ras and APC genes in primary colorectal carcinoma and synchronous metastases compared with the findings in accompanying adenomas. *Mol. Pathol.*, 56,137-140, 2003). These studies indicate that genetic changes of the APC gene in metastases are consistent with the primary colorectal cancer. However, epigenetic changes of the APC gene in colorectal cancer metastasis have not been explored yet.

The APC gene has two promoter regions, 1A and 1B; promoter 1A is most commonly active. Hypermethylation of the 1A promoter region of APC has previously been reported in some colorectal adenomas and carcinomas, but not in adjacent normal colonic mucosa. APC 1A promoter methylation has also been found in a number of other human gastrointestinal tumors, including oesophageal, gastric, pancreatic and hepatic cancers.

Bisulfite modification of DNA is an art-recognized tool used to assess CpG methylation status. 5-methylcytosine is the most frequent covalent base modification in the DNA of eukaryotic cells. It plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing, because 5-methylcytosine has the same base pairing behavior as cytosine. Moreover, the epigenetic information carried by 5-methylcytosine is completely lost during, e.g., PCR amplification.

The most frequently used method for analyzing DNA for the presence of 5-methylcytosine is based upon the specific reaction of bisulfite with cytosine whereby, upon subsequent alkaline hydrolysis, cytosine is converted to uracil which corresponds to thymine in its base pairing behavior. Significantly, however, 5-methylcytosine remains unmodified under these conditions. Consequently, the original DNA is converted in such a manner that methylcytosine, which originally could not be distinguished from cytosine by its hybridization behavior, can now be detected as the only remaining cytosine using standard, art-recognized molecular biological techniques, for example, by amplification and hybridization, or by sequencing. All of these techniques are based on differential base pairing properties, which can now be fully exploited.

The prior art, in terms of sensitivity, is defined by a method comprising enclosing the DNA to be analyzed in an agarose matrix, thereby preventing the diffusion and renaturation of the DNA (bisulfite only reacts with single-stranded DNA), and replacing all precipitation and purification steps with fast dialysis (Olek A, et al., A modified and improved method for bisulfite based cytosine methylation analysis, *Nucleic Acids Res.* 24:5064-6, 1996). It is thus possible to analyze individual cells for methylation status, illustrating the utility and sensitivity of the method. An overview of art-recognized methods for detecting 5-methylcytosine is provided by Rein, T., et al., *Nucleic Acids Res.*, 26:2255, 1998.

The bisulfite technique, barring few exceptions (e.g., Zeschnigk M, et al., *Eur J Hum Genet*. 5:94-98, 1997), is currently only used in research. In all instances, short, specific fragments of a known gene are amplified subsequent to a bisulfite treatment, and either completely sequenced (Olek & Walter, *Nat Genet.* 1997 17:275-6, 1997), subjected to one or more primer extension reactions (Gonzalgo & Jones, *Nucleic Acids Res.*, 25:2529-31, 1997; WO 95/00669; U.S. Pat. No. 6,251,594) to analyze individual cytosine positions, or treated by enzymatic digestion (Xiong & Laird, *Nucleic Acids Res.*, 25:2532-4, 1997). Detection by hybridization has also been described in the art (Olek et al., WO 99/28498). Additionally, use of the bisulfite technique for methylation detection with respect to individual genes has been described (Grigg & Clark, *Bioessays,* 16:431-6, 1994; Zeschnigk M, et al., *Hum Mol. Genet.,* 6:387-95, 1997; Feil R, et al., *Nucleic Acids Res.,* 22:695-, 1994; Martin V, et al., *Gene,* 157:261-4, 1995; WO 9746705 and WO 9515373).

Bisulfite Methylation Assay Procedures. Various methylation assay procedures are known in the art, and can be used in conjunction with the present invention. These assays allow for determination of the methylation state of one or a plurality of CpG dinucleotides (e.g., CpG islands) within a DNA sequence. Such assays involve, among other techniques, DNA sequencing of bisulfite-treated DNA, PCR (for sequence-specific amplification), Southern blot analysis, and use of methylation-sensitive restriction enzymes.

For example, genomic sequencing has been simplified for analysis of DNA methylation patterns and 5-methylcytosine distribution by using bisulfite treatment (Frommer et al., *Proc. Natl. Acad. Sci. USA* 89:1827-1831, 1992). Additionally, restriction enzyme digestion of PCR products amplified from bisulfite-converted DNA is used, e.g., the method described by Sadri & Hornsby (*Nucl. Acids Res.* 24:5058-5059, 1996), or COBRA (Combined Bisulfite Restriction Analysis) (Xiong & Laird, *Nucleic Acids Res.* 25:2532-2534, 1997).

COBRA. COBRA™ analysis is a quantitative methylation assay useful for determining DNA methylation levels at specific gene loci in small amounts of genomic DNA (Xiong & Laird, *Nucleic Acids Res.* 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (*Proc. Natl. Acad. Sci. USA* 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Other assays used in the art include "MethyLight™" (a fluorescence-based real-time PCR technique) (Eads et al., *Cancer Res.* 59:2302-2306, 1999), Ms-SNuPE™ (Methylation-sensitive Single Nucleotide Primer Extension) reactions (Gonzalgo & Jones, *Nucleic Acids Res.* 25:2529-2531, 1997), methylation-specific PCR ("MSP"; Herman et al., *Proc. Natl. Acad. Sci. USA* 93:9821-9826, 1996; U.S. Pat. No. 5,786, 146), and methylated CpG island amplification ("MCA"; Toyota et al., *Cancer Res.* 59:2307-12, 1999). These may be used alone or in combination with other of these methods.

MethyLight. Methylight™ is a novel high-throughput methylation assay that utilizes fluorescence-based real-time PCR technology that requires no further manipulation after the PCR step. It is a highly sensitive assay, capable of detecting methylated alleles in the presence of a 10,000-fold excess of unmethylated alleles, and can very accurately determine the relative prevalence of a particular pattern of DNA methylation The MethyLight™ assay utilizes fluorescence-based real-time PCR (TaqMan®) technology that requires no further manipulations after the PCR step (Eads et al., *Cancer Res.* 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the nuorescence detection process, or both.

The MethyLight™ assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight™ process can by used with a "TaqMan®" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Alternatively the Methylight™ process can be used with 'Lightcycler™' probes. A LightCycler™ probe is a pair of single-stranded fluorescent-labeled oligonucleotides. The first oligonucleotide probe is labeled at its 3' end with a donor fluorophore dye and the second is labeled at its 5' end with an acceptor fluorophore dyes. The free 3' hydroxyl group of the second probe is blocked with a phosphate group to prevent polymerase mediated extension. During the annealing step of real-time quantitative PCR, the PCR primers and the Light-Cycler™ probes hybridize to their specific target regions causing the donor dye to come into close proximity to the acceptor dye. When the donor dye is excited by light, energy is transferred by Fluorescence Resonance Energy Transfer (FRET) from the donor to the acceptor dye. The energy transfer causes the acceptor dye to emit fluorescence wherein the increase of measured fluorescence signal is directly proportional to the amount of target DNA.

Typical reagents (e.g., as might be found in a typical Methy Light™-based kit) for MethyLight™ analysis may include, but are not limited to: PCR primers for specific gene (or methylation-altered DNA sequence or CpG island); TaqMan® and/or LightCycler™ probes; optimized PCR buffers and deoxynucleotides; and Taq polymerase.

Ms-SNuPE. The Ms-SNuPE™ technique is a quantitative method for assessing methylation differences at specific CpG sites based on bisulfite treatment of DNA, followed by single-nucleotide primer extension (Gonzalgo & Jones, *Nucleic Acids Res.* 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific gene (or methylation-altered DNA sequence or CpG island); optimized PCR buffers and deoxynucleotides; gel extraction kit; positive control primers; Ms-SNuPE™ primers for specific gene; reaction buffer (for the Ms-SNuPE™ reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP. MSP (methylation-specific PCR) allows for assessing the methylation status of virtually any group of CpG sites within a CpG island, independent of the use of methylation-sensitive restriction enzymes (Herman et al. *Proc. Natl. Acad. Sci. USA* 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. This technique has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG dinucleotide. MSP primers specific for non-methylated DNA contain a "T" at the 3' position of the C position in the CpG. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

Treatment of metastatic colon cancer currently has a low success rate. Although a number of patients with isolated metastases to the liver have undergone surgical removal of liver metastases and been reported to experience long-term cancer-free survival, the majority of patients with isolated liver metastases ultimately fail treatment because the cancer recurs locally in the liver and/or elsewhere in the body. Therefore, in order to improve the results achieved with surgical removal of the liver metastases, therapy must be directed at controlling both cancer recurrence in the liver and elsewhere in the body. Administration of systemic chemotherapy has the potential to eradicate cancer cells remaining in the body following surgical removal of the liver metastases, and direct infusion of chemotherapy into the liver via the hepatic artery has the potential to destroy remaining cancer cells in the liver.

Pronounced need in the art. Therefore, in view of the incidence of colon cancer metastasis and the low success rate of treatment thereof there is a need for identifying patients who would benefit from systemic adjuvant treatment. Additionally, there is a pronounced need in the art for the development of molecular markers that could be used to provide sensitive, accurate and non-invasive methods (as opposed to, e.g., biopsy) for the diagnosis, prognosis and treatment of colon cell proliferative disorders.

SUMMARY OF THE DRAWINGS

FIGS. 1A and 1B show status of promoter methylation of the APC gene as assessed by Methylight assay. PMR: percentage methylated reference. FIG. 1A: APC promoter methylation in 39 primary colorectal cancers and 14 matched normal colon mucosa. FIG. 1B: APC promoter methylation in 39 primary colorectal cancers and 24 liver metastasis.

FIG. 2 shows APC protein expression in 5 matched non-neoplastic colon mucosa and primary colon cancer (N1T1-N5T5), 2 matched primary colon cancer and liver metastases (T6M6 and T7M7) using Western blot analysis. N, non-neoplastic mucosa; T, primary colon cancer; M, liver metastasis. Two isoforms of the APC protein (300 and 200 kDa, respectively) were observed. APC was expressed in all 5 matched non-neoplastic colon and cancerous tissues and 1 matched colon cancer and liver metastasis. In general the expression level of APC was decreased in colon cancer when compared with the corresponding non-neoplastic mucosa. In one matched colon cancer and liver metastasis the expression of APC protein was completely absent. No significant difference among the tissues with APC promoter methylation (T2, T5) versus cases without APC methylation (T1, T3, T4, T6M6 and T7M7) was observed. P, positive control.

FIG. 3 shows immunohistochemical expression of APC in colon and tumor tissue. The distribution and expression pattern of APC in colon cancer was investigated by immunohistochemistry. Non-tumorous epithelium, tumor, lymph node and liver metastases were stained with anti-APC antibodies. APC was found in the cytoplasm. In the majority of the patients studied, the intensity of immunostaining and the number of immunoreactive cells was decreased in tumorous epithelium (B) when compared with the corresponding non-tumorous epithelium (A). Hematoxylin counterstain; Original magnification: ×400.

DETAILED DESCRIPTION OF THE INVENTION

Figure 1:
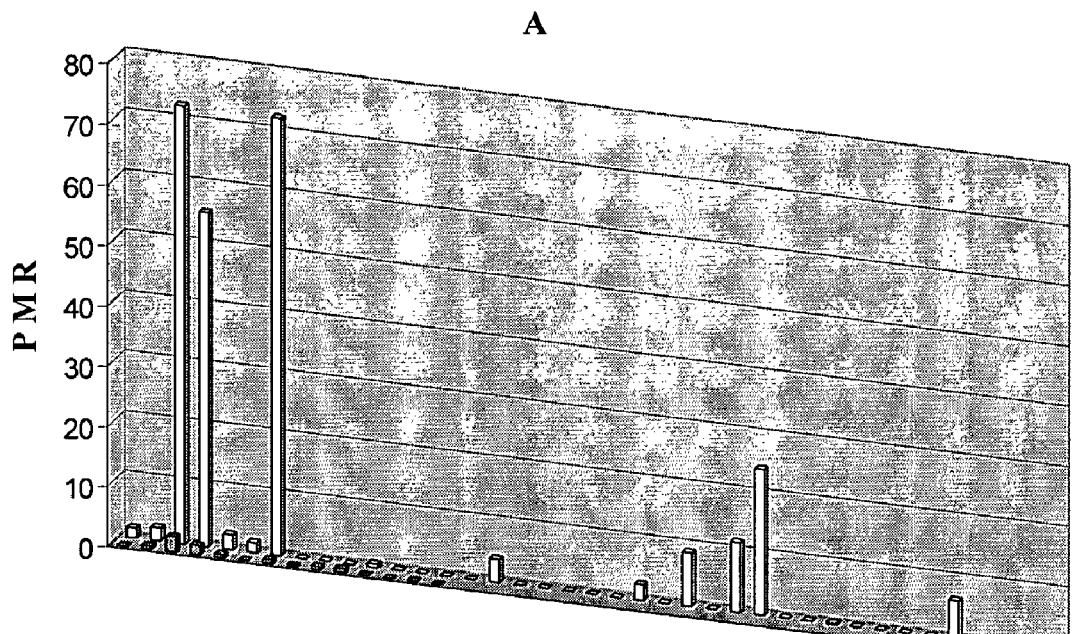
FIGS. 1 to 3 relate to Example 1.

For the purposes of the following invention the terms 'sensitivity' and 'specificity' refer to values calculated by reference to a sample set according to that described in the examples contained herein.

Definitions:

The term "Observed/Expected Ratio" ("O/E Ratio") refers to the frequency of CpG dinucleotides within a particular DNA sequence, and corresponds to the [number of CpG sites/(number of C bases×number of G bases)]×band length for each fragment.

The term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 kb in length.

The term "methylation state" or "methylation status" refers to the presence or absence of 5-methylcytosine ("5-mCyt") at one or a plurality of CpG dinucleotides within a DNA sequence. Methylation states at one or more particular palindromic CpG methylation sites (each having two CpG CpG dinucleotide sequences) within a DNA sequence include "unmethylated," "fully-methylated" and "hemi-methylated."

The term "hemi-methylation" or "hemimethylation" refers to the methylation state of a double stranded DNA comprising on each strand CpG methylation site, where only the CpGs of one strand are methylated.

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "microarray" refers broadly to both "DNA microarrays," and 'DNA chip(s),' as recognized in the art, encompasses all art-recognized solid supports, and encompasses all methods for affixing nucleic acid molecules thereto or synthesis of nucleic acids thereon.

"Genetic parameters" are mutations and polymorphisms of genes and sequences further required for their regulation. To be designated as mutations are, in particular, insertions, deletions, point mutations, inversions and polymorphisms and, particularly preferred, SNPs (single nucleotide polymorphisms).

"Epigenetic parameters" are, in particular, cytosine methylations. Further epigenetic parameters include, for example, the acetylation of histones which, however, cannot be directly analyzed using the described method but which, in turn, correlate with the DNA methylation.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The term "methylation assay" refers to any assay for determining the methylation state of one or more CpG dinucleotide sequences within a sequence of DNA.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al., *Cancer Research* 57:594-599, 1997.

The term "MethyLight®" refers to the art-recognized fluorescence-based real-time PCR technique described by Eads et al., *Cancer Res.* 59:2302-2306, 1999.

The term "HeavyMethyl™" assay, in the embodiment thereof implemented herein, refers to a HeavyMethyl Methylight® assay, which is a variation of the Methylight® assay, wherein the Methylight® assay is combined with methylation specific blocking probes covering CpG positions between the amplification primers.

The term "Ms-SNuPE™" (Methylation-sensitive Single Nucleotide Primer Extension) refers to the art-recognized assay described by Gonzalgo & Jones, *Nucleic Acids Res.* 25:2529-2531, 1997.

The term "MSP" (Methylation-specific PCR) refers to the art-recognized methylation assay described by Herman et al. *Proc. Natl. Acad. Sci. USA* 93:9821-9826, 1996, and by U.S. Pat. No. 5,786,146.

The term "COBRA™" (Combined Bisulfite Restriction Analysis) refers to the art-recognized methylation assay described by Xiong & Laird, *Nucleic Acids Res.* 25:2532-2534, 1997.

The term "MCA" (Methylated CpG Island Amplification) refers to the methylation assay described by Toyota et al., *Cancer Res.* 59:2307-12, 1999, and in WO 00/26401A1.

The term "hybridization" is to be understood as a bond of an oligonucleotide to a complementary sequence along the lines of the Watson-Crick base pairings in the sample DNA, forming a duplex structure.

"Stringent hybridization conditions," as defined herein, involve hybridizing at 68° C. in 5×SSC/5×Denhardt's solution/1.0% SDS, and washing in 0.2×SSC/0.1% SDS at room temperature, or involve the art-recognized equivalent thereof (e.g., conditions in which a hybridization is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognized equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

The term 'primary' when used in reference to cancer or other cell proliferative disorder shall be taken to mean the first to develop.

The term 'metastasis' as used herein shall be taken to mean the transfer of a disease-producing agent (such as bacteria, cancer or other cell proliferative disorder cells) from an original site of disease to another part of the body with development of a similar lesion in the new location.

Overview:

Despite intensive efforts to improve treatment of colon cell proliferative disorders, most cases are diagnosed in an advanced stage with regional or distant metastasis which are associated with poor survival. The herein described invention discloses genetic methylation markers that have novel utility for detection of metastasis of colon cell proliferative disorders or determining likelihood of development thereof, and in further embodiments provides sensitive assay methods for the improved prognostic analysis of said disorders. The invention is particularly preferred for the detection of metastasis of colon carcinoma located in the liver or determining the likelihood of development thereof.

The invention presents improvements over the state of the art in that it provides a means for the detection and/or prediction of metastasis of colon cell proliferative disorders, most particularly colon carcinoma by analysis of the methylation patterns of at least one or a plurality of genes and/or their regulatory sequences. In one embodiment the gene is APC and/or its regulatory sequences. The invention is particularly preferred for the detection of metastasis of colon carcinoma located in the liver or likelihood of metastasis of colon carcinoma. Furthermore APC methylation can be used as a marker to confirm that liver metastasis of unknown origin is from colon cancer primary and also to distinguish between liver cancer originating from a metastasis from a liver heptocellular carcinoma.

In a further preferred embodiment the methylation of the gene APC and/or its regulatory sequences and one or more genes of a panel of genes consisting of TPEF, p16/INK4A and ALX4, and/or their regulatory sequences is determined and therefrom a prognosis concerning likelihood of progression to metastases is determined. Said embodiments having a combined utility for the detection and prognosis of colon carcinoma.

In one aspect, the present invention provides for the use of the bisulfite technique, in combination with one or more methylation assays, for determination of the methylation status of CpG dinucleotide sequences of at least one of the genes taken from the group consisting ALX4, TPEF, p16/INK4A, APC and/or their regulatory sequences. It is most preferred that said gene is APC. According to the present invention, determination of the methylation status of CpG dinucleotide sequences within the gene APC has prognostic utility.

Although hypermethylation is commonly known in a wide variety of cancers, it has not been widely investigated as a prognostic marker and hypermethylation of genes in metastasis from colon carcinoma is not known in the art. Although hypermethylation of the gene APC is known in colon cancer, a person skilled in the art would not necessarily be led to investigate its use as a prognostic marker. There is nothing in the art to indicate that the gene APC is capable of distinguishing between primary and metastasized tumors or suchlike. Furthermore, hypermethylation of a gene is widely accepted as a modulating factor in gene expression (and thereby protein levels) wherein gene transcription is hindered by methylation thereby leading to decreased levels of expression. As can be seen from the examples that follow, protein levels of the gene APC are not significantly different between colon tissue, colon carcinoma and colon carcinoma metastasis. Therefore a person skilled in the art would not as a matter of course be lead to investigate the use of methylation analysis as a prognostic marker (i.e., one capable of differentiating between primary colon carcinoma and colon carcinoma metastasis) on the basis of its hypermethylation in colon carcinoma.

Particular embodiments of the present invention provide a novel application of the analysis of methylation levels and/or patterns of the gene APC and/or its regulatory sequences that enable a precise prognosis of the likelihood of metastasis and thereby enable the improved treatment and thus overall prognosis of colon cell proliferative disorders. The invention is particularly preferred for the detection of metastasis of colon carcinoma located in the liver. The disclosed method thereby enables the physician and patient to make better and more informed treatment decisions.

In particular aspects, the present invention provides improved means for the prognosis of metastasis of colorectal cell proliferative disorders. This aim is achieved by the analysis of the CpG methylation status of at least one or a plurality of genes and/or their regulatory regions. In one embodiment the CpG methylation status of the gene APC and/or its regulatory sequences is analysed. The invention is particularly preferred for the detection of metastasis of colon carcinoma located in the liver.

In a further aspect the aim of the invention is achieved by the methylation analysis of said gene, APC and/or its regulatory sequences and one or more genes selected from the group consisting ALX4, TPEF, p16/INK4A, APC and/or their regulatory sequences. Said group of genes consisting ALX4, TPEF, p16/INK4A, APC and/or their regulatory sequences having heretofore unknown utility in the detection of colon carcinoma. Therefore said analysis is particularly suited to a combined diagnostic and prognostic colon cell proliferative disorder test.

The present invention is further based upon the analysis of methylation levels within said gene, APC and/or its regulatory sequences and one or more genes selected from the group consisting ALX4, TPEF and p16/INK4A and/or their regulatory sequences said group of genes being further preferred markers for the detection of colon cancer.

Accordingly, the invention also disclose the genomic sequences of said genes in SEQ ID NOS:1 to SEQ ID NO:4, according to TABLE 2. Additional embodiments provide modified variants of SEQ ID NOS:1 to SEQ ID NO:4, as well as oligonucleotides and/or PNA-oligomers for analysis of cytosine methylation patterns within SEQ ID NOS:1 to SEQ ID NO:4. Said modified variants of SEQ ID NO: 1 to 4, namely SEQ ID NO: 5 to 20 (as shown in Table 2) providing the sequences of said genomic nucleic acids subsequent to a treatment suitable for the conversion of all unmethylated cytosine positions to uracil (e.g. bisulfite treatment).

According to the present invention aberrant methylation patterns are associated with the development of metastasis in colon cell proliferative disorders. In particular hypermethylation of the gene APC and/or its regulatory sequences is correlated with metastasis of colon cell proliferative disorders. The invention is particularly preferred for the detection of metastasis of colon carcinoma located in the liver. Methylation analysis of this gene is herein shown to have the surprising effect of being a prognostic marker. Furthermore this prognostic marker is improved by a combined analysis of the gene APC and one or more genes selected from the group consisting of TPEF, p16/INK4A, APC said analysis having a further utility as a diagnostic marker.

The present invention discloses the analysis of methylation within said genes and/or their regulatory sequences in the form of a panel enabling the combined detection and prediction of metastasis and thereby treatment and overall prognosis of colon cell proliferative disorders.

Aberrant methylation of the genes TPEF, p16/INK4A, caveolin-2, DAPK and TIMP3 have to date been associated with the development of colorectal cell proliferative disorders. The present invention provides specific combinations of these genes with the gene APC which were determined to be particularly useful as diagnostic and prognostic markers of colorectal cell proliferative disorders. Accordingly, it is further preferred that the methylation of the gene APC and/or its regulatory sequences and at least one or more of the genes selected from the group consisting ALX4, TPEF and p16 and/or their regulatory sequences are analysed.

An objective of the invention comprises analysis of the methylation state of one or more CpG dinucleotides within SEQ ID NO:1. In a further embodiment the methylation status of at least one CpG position of SEQ ID NO:1 and at least one CpG position taken from the group of sequences consisting of SEQ ID NOS:1 to SEQ ID NO:4 and sequences complementary thereto are analysed.

It is further preferred that the methylation status of at least one CpG position of SEQ ID NO:1 and at least one CpG position taken from the group of sequences consisting of SEQ ID NOS:2-4 are analysed.

The disclosed invention further provides treated nucleic acids, derived from genomic SEQ ID NOS:1 to SEQ ID NO:4, wherein the treatment is suitable to convert at least one unmethylated cytosine base of the genomic DNA sequence to uracil or another base that is detectably dissimilar to cytosine in terms of hybridization. The genomic sequences in question may comprise one, or more, consecutive or random methylated CpG positions. Said treatment preferably comprises use of a reagent selected from the group consisting of bisulfite, hydrogen sulfite, disulfite, and combinations thereof. Nucleic acids treated accordingly are herein also referred to as 'modified' nucleic acids.

In a preferred embodiment of the invention, the objective comprises analysis of at least one modified nucleic acid comprising a sequence of at least 16 contiguous nucleotide bases in length of a sequence selected from the group consisting of SEQ ID NO:5, 6, 13 and 14, wherein said sequence comprises at least one CpG, TpA or CpA dinucleotide and sequences complementary thereto. It is also preferred that at least one modified nucleic acid comprising a sequence of at least 16 contiguous nucleotide bases in length of a sequence selected from the group consisting of SEQ ID NO:5 to SEQ ID NO:20 are analysed in addition to at least 16 contiguous nucleotide bases in length of a sequence selected from the group consisting of SEQ ID NO:5, 6, 13 and 14, wherein said sequence comprises at least one CpG, TpA or CpA dinucleotide and sequences complementary thereto.

The analysed nucleic acids may comprise at least 16, 20, 25, 30 or 35 nucleotides in length of SEQ ID NO: 5 to 20.

The sequences of SEQ ID NOS:5 to SEQ ID NO:20 provide modified versions of the nucleic acid according to SEQ ID NOS:1 to SEQ ID NO:4, wherein the modification of each genomic sequence results in the synthesis of a nucleic acid having a sequence that is unique and distinct from said genomic sequence as follows. For each sense strand genomic DNA, e.g., SEQ ID NO:1, four converted versions are disclosed. A first version wherein 'C' is converted to 'T' but 'CpG' remains 'CpG' (i.e., corresponds to case where, for the genomic sequence, all 'C' residues of CpG dinucleotide sequences are methylated and are thus not converted); a second version discloses the complement of the disclosed genomic DNA sequence (i.e., antisense strand), wherein 'C' is converted to 'T' but 'CpG' remains 'CpG' (i.e., corresponds to case where, for all 'C' residues of CpG dinucleotide sequences are methylated and are thus not converted). The 'upmethylated' converted sequences of SEQ ID NO:1 to SEQ ID NO: 4 correspond to SEQ ID NO:5 to SEQ ID NO:12 (see TABLE 2). A third chemically converted version of each genomic sequences is provided, wherein 'C' is converted to 'T' or all 'C' residues, including those of 'CpG' dinucleotide sequences (i.e., corresponds to case where, for the genomic sequences, all 'C' residues of CpG dinucleotide sequences are umethylated); a final chemically converted version of each sequence, discloses the complement of the disclosed genomic DNA sequence (i.e. antisense strand), wherein 'C' is converted to 'T' for all 'C' residues, including those of 'CpG' dinucleotide sequences (i.e., corresponds to case where, for the complement (antisense strand) of each genomic sequence, all 'C' residues of CpG dinucleotide sequences are unmethylated). The 'downmethylated' converted sequences of SEQ ID NO: 1 to SEQ ID NO: 4 correspond to SEQ ID NO:13 to SEQ ID NO:20 and.

Particularly useful as a prognostic marker of colon cell proliferative disorders are the non-naturally occurring sequences according to SEQ ID Nos:5, 6, 14 and 15 which correspond to methylation specific converted sequences of part of the gene APC (SEQ ID NO:1).

In an alternative preferred embodiment, such analysis comprises the use of an oligonucleotide or oligomer for detecting the cytosine methylation state within genomic or treated (chemically modified) DNA, according to and particularly preferred SEQ ID NO:1, but also SEQ ID NOS: 2 to SEQ ID NO:4. Said oligonucleotide or oligomer comprising a nucleic acid sequence having a length of at least nine (9) nucleotides which hybridizes, under moderately stringent or stringent conditions (as defined herein above), to a pretreated nucleic acid sequence according to SEQ ID NOS:5 to SEQ ID NO:20 and/or sequences complementary thereto, or to a genomic sequence according to SEQ ID NOS:1 to SEQ ID NO:4 and/or sequences complementary thereto.

Preferably said oligomers comprise at least one T nucleotide wherein the corresponding base position within genomic (i.e. untreated) DNA is a C, said genomic equivalent of SEQ ID NO: 2 to SEQ ID NO: 4 as provided in the sequence listing (see Table 2).

Thus, the present invention includes nucleic acid molecules (e.g., oligonucleotides and peptide nucleic acid (PNA) molecules (PNA-oligomers)) that hybridize under moderately stringent and/or stringent hybridization conditions to all or a portion of the sequences SEQ ID NOS: 1 to SEQ ID NO: 20, or to the complements thereof. The hybridizing portion of the hybridizing nucleic acids is typically at least 9, 15, 20, 25, 30 or 35 nucleotides in length. However, longer molecules have inventive utility, and are thus within the scope of the present invention.

Preferably, the hybridizing portion of the inventive hybridizing nucleic acids is at least 95%, or at least 98%, or 100% identical to the sequence, or to a portion thereof of SEQ ID NOS:1 to SEQ ID NO:20, or to the complements thereof.

Hybridizing nucleic acids of the type described herein can be used, for example, as a primer (e.g., a PCR primer), or a diagnostic and/or prognostic probe or primer. Preferably, hybridization of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NOS:1 to SEQ ID NO:4 (such as allelic variants and SNPs), rather than identical, it is useful to first establish the lowest temperature at which only homologous hybridization occurs with a particular concentration of salt (e.g., SSC or SSPE). Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., SEQ ID NO:1, include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions:

n to (n+(X−1));

where n=1, 2, 3, ... (Y−(X−1));

where Y equals the length (nucleotides or base pairs);

where X equals the common length (in nucleotides) of each oligonucleotide in the set (e.g., X=20 for a set of consecutively overlapping 20-mers); and where the number (Z) of consecutively overlapping oligomers of length X for a given sequence of length Y is equal to Y−(X−1).

Preferably, the set is limited to those oligomers that comprise at least one CpG, TpG or CpA dinucleotide.

Examples of inventive 20-mer oligonucleotides within a sequence of length 2470 base pairs include the following set of 2470 oligomers (and the antisense set complementary thereto), indicated by polynucleotide positions 1-20, 2-21, 3-22, 4-23, 5-24 to 2451-2470.

Preferably, the set is limited to those oligomers that comprise at least one CpG, TpG or CpA dinucleotide.

The present invention encompasses, for each of SEQ ID NOS:1 to SEQ ID NO:20 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequence corresponding to SEQ ID NOS:1 to SEQ ID NO:4. Preferred sets of such oligonucleotides or modified oligonucleotides of length X are those consecutively overlapping sets of oligomers corresponding to SEQ ID NOS:1 to SEQ ID NO:20 (and to the complements thereof). Preferably, said oligomers comprise at least one CpG, TpG or CpA dinucleotide.

Particularly preferred oligonucleotides or oligomers according to the present invention are those in which the cytosine of the CpG dinucleotide (or of the corresponding converted TpG or CpA dinculeotide) sequences is within the middle third of the oligonucleotide; that is, where the oligonucleotide is, for example, 13 bases in length, the CpG, TpG or CpA dinucleotide is positioned within the fifth to ninth nucleotide from the 5'-end.

The oligonucleotides of the invention can also be modified by chemically linking the oligonucleotide to one or more moieties or conjugates to enhance the activity, stability or prognosis of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., BioTechniques 6:958-976, 1988) or intercalating agents (Zon, Pharm. Res. 5:539-549, 1988). To this end, the oligonucleotide may be conjugated to another molecule, e.g., a chromophore, fluorophor, peptide, hybridization-triggered cross-linking agent, transport agent, hybridization-triggered cleavage agent, etc.

The oligonucleotide may also comprise at least one art-recognized modified sugar and/or base moiety, or may comprise a modified backbone or non-natural internucleoside linkage.

The oligonucleotides or oligomers according to particular embodiments of the present invention are typically used in 'sets,' which contain at least one oligomer for analysis of each of the CpG dinucleotides of the genomic sequences to be analysed, in a preferred embodiment SEQ ID NOS:1 to SEQ ID NO:4 and sequences complementary thereto, or to the corresponding CpG, TpG or CpA dinucleotide within a sequence of the pretreated nucleic acids according to SEQ ID NOS:5 to SEQ ID NO:20 and sequences complementary thereto. In a further preferred embodiment the set comprises contain at least one oligomer for analysis of each of the CpG dinucleotides of genomic sequence SEQ ID NO:1 and sequences complementary thereto, or to the corresponding CpG, TpG or CpA dinucleotide within a sequence of the pretreated nucleic acids according to SEQ ID NOS: 5, 6, 13 and 14.

However, it is anticipated that for economic or other factors it may be preferable to analyze a limited selection of the CpG dinucleotides within said sequences, and the content of the set of oligonucleotides is altered accordingly.

Therefore, in particular embodiments, the present invention provides a set of at least two (2) (oligonucleotides and/or PNA-oligomers) useful for detecting the cytosine methylation state in pretreated genomic DNA of the gene APC and/or its regulatory sequences (SEQ ID NO:1) or in pretreated genomic DNA thereof(SEQ ID NOS: 5, 6, 13 and 14).

In further embodiments, the present invention provides a set of at least two (2) (oligonucleotides and/or PNA-oligomers) useful for detecting the cytosine methylation state in pretreated genomic DNA of the gene APC and/or its regulatory sequences (SEQ ID NO:1) or in pretreated genomic DNA thereof (SEQ ID NOS: 5, 6, 13 & 14) and pretreated genomic DNA of at least two genes selected from ALX4, TPEF and p16 (SEQ ID NOS:7 to SEQ ID NO:12 and SEQ ID NOS:15 to SEQ ID NO:20), or in genomic DNA (SEQ ID NOS:2 to SEQ ID NO:4 and sequences complementary thereto).

In further embodiments, the present invention provides a set of at least two (2) (oligonucleotides and/or PNA-oligomers) useful for detecting the cytosine methylation state in pretreated genomic DNA of the gene APC and/or its regulatory sequences (SEQ ID NO:1) or in pretreated genomic DNA thereof (SEQ ID NOS:5, 6, 13 & 14) and pretreated genomic DNA of at least two genes selected from ALX4, TPEF, p16, (SEQ ID NOS:7 to SEQ ID NO:12, SEQ ID NOS:15 to SEQ ID NO:20), or in genomic DNA (SEQ ID NOS:2 to SEQ ID NO:4 and sequences complementary thereto).

In preferred embodiments, at least one, and more preferably all members of the set of oligonucleotides is bound to a solid phase.

In further embodiments, the present invention provides a set of at least two (2) oligonucleotides that are used as 'primer' oligonucleotides for amplifying DNA sequences. Most preferably said primer oligonucleotides hybridise to at least one of SEQ ID NOS: 1, 5, 6, 13 and 14. In a further embodiment said set of primers further comprise oligonucleotides which hybridise to at least one of the group consisting SEQ ID NOS:2 to SEQ ID NO:20 and sequences complementary thereto, or segments thereof.

It is anticipated that the oligonucleotides may constitute all or part of an 'array' or 'DNA chip' (i.e., an arrangement of different oligonucleotides and/or PNA-oligomers bound to a solid phase). Such an array of different oligonucleotide- and/or PNA-oligomer sequences can be characterized, for example, in that it is arranged on the solid phase in the form of a rectangular or hexagonal lattice. The solid-phase surface may be composed of silicon, glass, polystyrene, aluminum, steel, iron, copper, nickel, silver, or gold. Nitrocellulose as well as plastics such as nylon, which can exist in the form of pellets or also as resin matrices, may also be used. An overview of the Prior Art in oligomer array manufacturing can be gathered from a special edition of Nature Genetics (*Nature Genetics Supplement, Volume* 21, January 1999, and from the literature cited therein). Fluorescently labeled probes are often used for the scanning of immobilized DNA arrays. The simple attachment of Cy3 and Cy5 dyes to the 5'-OH of the specific probe are particularly suitable for fluorescence labels. The prognosis of the fluorescence of the hybridized probes may be carried out, for example, via a confocal microscope. Cy3 and Cy5 dyes, besides many others, are commercially available.

It is particularly preferred that the oligomers according to the invention are utilised for the prognosis of colorectal carcinoma.

The present invention further provides a method for ascertaining the CpG methylation state of selected CpG positions within the genes ALX4, TPEF, p16, APC, and/or their regulatory sequences within a subject and determining therefrom upon the presence of metastasis of colon cell proliferative disorders or determining likelihood of development thereof.

It is particularly preferred that the methylation state of at least one CpG position of the gene APC and or its regulatory sequences is analysed. In a further embodiment of the method it is preferred that the methylation status of at least one CpG position of the gene APC and/or its regulatory sequences and at least one CpG position of one or more of the genes of the group consisting TPEF, p16, ALX4 and/or their regulatory sequences are analysed.

Accordingly, it is preferred that the methylation state of at least one CpG position of the genomic sequence SEQ ID NO:1 is analysed. In a further embodiment of the method it is preferred that the methylation state of at least one CpG position of the genomic sequence SEQ ID NO:1 and at least one CpG position of one or more of the group consisting the genomic sequences SEQ ID NOS: 2-4 are analysed.

Said method comprising contacting a nucleic acid comprising the appropriate gene(s) and/or their regulatory sequences, most preferably SEQ ID NO:1 or SEQ ID NO:1 and one or more of SEQ ID NOS:2 to SEQ ID NO:4 in a biological sample obtained from said subject with at least one reagent or a series of reagents, wherein said reagent or series of reagents, distinguishes between methylated and non-methylated CpG dinucleotides within the target nucleic acid.

It is preferred that the methylation state of at least one CpG position of the genomic sequence SEQ ID NO:1 is analysed.

In a further embodiment of the method it is preferred that the methylation status of at least one CpG position of the genomic sequence SEQ ID NO:1 and one or more of the group consisting the genomic sequences SEQ ID NOS: 2-4 are analysed.

Said method comprising contacting a nucleic acid comprising the appropriate gene(s) and/or their regulatory sequences or SEQ ID NO:1 or SEQ ID NO:1 and one or more of SEQ ID NOS:2 to SEQ ID NO:4 in a biological sample obtained from said subject with at least one reagent or a series of reagents, wherein said reagent or series of reagents, distinguishes between methylated and non-methylated CpG dinucleotides within the target nucleic acid.

Preferably, said method comprises the following steps: In the first step, a sample of the tissue to be analysed is obtained. The source may be any suitable source, such as colon cell lines, histological slides, biopsies, tissue embedded in paraffin and all possible combinations thereof. Genomic DNA is then isolated from said biological sample, this may be by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

Once the nucleic acids have been extracted, the genomic double stranded DNA is used in the analysis.

In the second step of the method, the genomic DNA sample is treated in such a manner that cytosine bases which are unmethylated at the 5'-position are converted to uracil, thymine, or another base which is dissimilar to cytosine in terms of hybridization behavior. This will be understood as 'pretreatment' herein.

The above described pretreatment of genomic DNA is preferably carried out with bisulfite (hydrogen sulfite, disulfite) and subsequent alkaline hydrolysis which results in a conversion of non-methylated cytosine nucleobases to uracil or to another base which is detectably dissimilar to cytosine in terms of base pairing behavior. If bisulfite solution is used for the reaction, then an addition takes place at the non-methylated cytosine bases. Moreover, a denaturating reagent or solvent as well as a radical interceptor must be present. A subsequent alkaline hydrolysis then gives rise to the conversion of non-methylated cytosine nucleobases to uracil. The converted DNA is then used for the detection of methylated cytosines.

It is particularly preferred that the genomic DNA of SEQ ID NO: 1 to 4 is thereby converted to the equivalent sequence selected from the group consisting SEQ ID NO: 5 SEQ ID NO: 20. Particularly preferred according to the present invention is the analysis of at least one CpG position of an amplificate of said sequences amplifiable by the use of corresponding primers of Table 1 or hybridizing to the oligonucleotides of Table 1.

In the third step of the method, fragments of the pretreated DNA are amplified, using sets of primer oligonucleotides according to the present invention, and an amplification enzyme. The amplification of several DNA segments can be carried out simultaneously in one and the same reaction vessel. Said amplification may be carried out as a 'singleplex' reaction wherein only a single amplification is carried out, or as a 'multiplex' reaction wherein the amplification of a plurality of sequences is carried out simultaneously. Because of statistical and practical considerations, wherein said amplification is a multiplex reaction preferably more than five different fragments having a length of 75-2000 base pairs are amplified. Typically, the amplification is carried out using a polymerase chain reaction (PCR). The set of primer oligonucleotides includes at least two oligonucleotides whose sequences are each reverse complementary, identical, or hybridize under stringent or highly stringent conditions to an at least 16-base-pair long segment of the base sequences. Most preferably this sequence is one of SEQ ID NOS: 5, 6, 13 and 14. In a further embodiment said set further comprises at least one or more pairs of oligonucleotides whose sequences are each reverse complementary, identical, or hybridize under stringent or highly stringent conditions to an at least 16-base-pair long segment of the base sequences of one or more of SEQ ID NOS:7 to SEQ ID NO:12 and SEQ ID NOS:15 to SEQ ID NO:20 and sequences complementary thereto.

In an alternate embodiment of the method, the methylation status of at least one CpG position within the previously specified nucleic acid sequences may be detected by use of methylation-specific primer oligonucleotides. Most preferably this sequence comprises SEQ ID NO:1, and in a further embodiment SEQ ID NO:1 and one or more of SEQ ID NOS:2 to SEQ ID NO:4. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG dinucleotide. MSP primers specific for non-methylated DNA contain a "T" at the 3' position of the C position in the CpG. Preferably, therefore, the base sequence of said primers is required to comprise a sequence having a length of at least 9 nucleotides which hybridizes to a pretreated nucleic acid sequence according to SEQ ID NOS: 5, 6, 13 and 14. In a further embodiment a set of MSP primers are used wherein said set comprises at least one pair of primers having a length of at least 9 nucleotides which hybridizes to a pretreated nucleic acid sequence according to SEQ ID NOS: 5, 6, 13 and 14 and furthermore at least one pair of SEQ ID NOS:7 to SEQ ID NO:20 and sequences complementary thereto, wherein the base sequence of said oligomers comprises at least one CpG dinucleotide.

A further preferred embodiment of the method comprises the use of blocker oligonucleotides. The use of such blocker oligonucleotides has been described by Yu et al., *BioTechniques* 23:714-720, 1997. Blocking probe oligonucleotides are hybridized to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for prognosis of methylated nucleic acids within a population of unmethylated nucleic acids, suppression of the amplification of nucleic acids which are unmethylated at the position in question would be carried out by the use of blocking probes comprising a 'CpA' or 'TpA' at the position in question, as opposed to a 'CpG' if the suppression of amplification of methylated nucleic acids is desired.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivitized at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-terminii thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

Preferably, therefore, the base sequence of said blocking oligonucleotides is required to comprise a sequence having a length of at least 9 nucleotides which hybridizes to a pretreated nucleic acid sequence according to one of SEQ ID NO: 5, 6, 13 & 14 and sequences complementary thereto, wherein the base sequence of said oligonucleotides comprises at least one CpG, TpG or CpA dinucleotide.

In a further embodiment it is preferred that said blocking oligonucleotides includes at least two oligonucleotides wherein at least one oligonucleotide comprises a sequence having a length of at least 9 nucleotides which hybridizes to a pretreated nucleic acid sequence according to one of SEQ ID NOS:5, 6, 13 and 14, and further at least one oligonucleotide comprises a sequence having a length of at least 9 nucleotides which hybridizes to a pretreated nucleic acid sequence according to one of SEQ ID NOS:7-20.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labeled amplificates have a single positive or negative net charge, allowing for better detectability in the mass spectrometer. The prognosis may be carried out and visualized by means of, e.g., matrix assisted laser desorption/ionization mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas & Hillenkamp, *Anal Chem.*, 60:2299-301, 1988). An analyte is embedded in a light-absorbing matrix. The matrix is evaporated by a short laser pulse thus transporting the analyte molecule into the vapour phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut & Beck, *Current Innovations and Future Trends*, 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionization process via the matrix is considerably less efficient. In MALDI-TOF spectrometry, the selection of the matrix plays an eminently important role. For desorption of peptides, several very efficient matrixes have been found which produce a very fine crystallisation. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut & Beck, *Nucleic Acids Res.* 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the prognosis of unmodified substrates considerably more difficult.

In the fourth step of the method, the amplificates obtained during the third step of the method are analysed in order to ascertain the methylation status of the CpG dinucleotides prior to the treatment.

In embodiments where the amplificates were obtained by means of MSP amplification, the presence or absence of an amplificate is in itself indicative of the methylation state of the CpG positions covered by the primer, according to the base sequences of said primer.

Amplificates obtained by means of both standard and methylation specific PCR may be further analyzed by means of hybridization-based methods such as, but not limited to, array technology and probe based technologies as well as by means of techniques such as sequencing and template directed extension.

In one embodiment of the method, the amplificates synthesised in step three are subsequently hybridized to an array or a set of oligonucleotides and/or PNA probes. In this context, the hybridization takes place in the following manner: the set of probes used during the hybridization is preferably composed of at least 2 oligonucleotides or PNA-oligomers; in the process, the amplificates serve as probes which hybridize to oligonucleotides previously bonded to a solid phase; the non-hybridized fragments are subsequently removed; said oligonucleotides contain at least one base sequence having a length of at least 9 nucleotides which is reverse complementary or identical to a segment of the base sequences specified in the present Sequence Listing; and the segment comprises at least one CpG, TpG or CpA dinucleotide.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. One oligonucleotide exists for the analysis of at least one CpG dinucleotide within the sequence according to SEQ ID NO: 1 and in a further embodiment said set further comprises one oligonucleotide for the analysis of at least one CpG dinucleotide within the sequence according to contains to SEQ ID NOS:2-4, and the equivalent positions within SEQ ID NOS:5 to SEQ ID NO: 12 & SEQ ID NOS:15 to SEQ ID NO:20. Said oligonucleotides may also be present in the form of peptide nucleic acids. The non-hybridized amplificates are then removed. The hybridized amplificates are then detected. In this context, it is preferred that labels attached to the amplificates are identifiable at each position of the solid phase at which an oligonucleotide sequence is located.

In yet a further embodiment of the method, the genomic methylation status of the CpG positions may be ascertained by means of oligonucleotide probes that are hybridised to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., *Genome Res.* 6:986-994, 1996; also see U.S. Pat. No. 6,331,393) employing a dual-labeled fluorescent oligonucleotide probe (TaqMan™ PCR, using an ABI Prism 7700 Sequence Prognosis System, Perkin Elmer Applied Biosystems, Foster City, Calif.). The TaqMan™ PCR reaction employs the use of a nonextendible interrogating oligonucleotide, called a TaqMan™ probe, which, in preferred imbodiments, is designed to hybridize to a GpC-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. For analysis of methylation within nucleic acids subsequent to bisulfite treatment, it is required that the probe be methylation specific, as described in U.S. Pat. No. 6,331,393, (hereby incorporated by reference in its entirety) also known as the Methylight™ assay. Variations on the TaqMan™ prognosis methodology that are also suitable for use with the described invention include the use of dual-probe technology (Lightcycler™) or fluorescent amplification primers (Sunrise™ technology). Both these techniques may be adapted in a manner suitable for use with bisulfite treated DNA, and moreover for methylation analysis within CpG dinucleotides.

A further suitable method for the use of probe oligonucleotides for the assessment of methylation by analysis of bisulfite treated nucleic acids In a further preferred embodiment of the method, the fourth step of the method comprises the use of template-directed oligonucleotide extension, such as MS-SNuPE™ as described by Gonzalgo & Jones, *Nucleic Acids Res.* 25:2529-2531, 1997.

In yet a further embodiment of the method, the fourth step of the method comprises sequencing and subsequent sequence analysis of the amplificate generated in the third step of the method (Sanger F., et al., *Proc Natl Acad Sci USA* 74:5463-5467, 1977).

Best Mode

In the most preferred embodiment of the method the nucleic acid according to SEQ ID NO:1 is isolated and treated according to the first three steps of the method outlined above, namely:

a. obtaining, from a subject, a biological sample having subject genomic DNA;

b. extracting or otherwise isolating the genomic DNA;

c. treating the genomic DNA of b), or a fragment thereof, with one or more reagents to convert cytosine bases that are unmethylated in the 5-position thereof to uracil or to another base that is detectably dissimilar to cytosine in terms of hybridization properties;

and wherein the subsequent amplification of d) is carried out in a methylation specific manner, namely by use of methylation specific primers or blocking oligonucleotides, and further wherein the prognosis of the amplificates is carried out by means of a real-time prognosis probes, as described above.

Wherein the subsequent amplification of d) is carried out by means of methylation specific primers, as described above, said methylation specific primers comprise a sequence having a length of at least 9 nucleotides which hybridizes to a pretreated nucleic acid sequence according to one of SEQ ID NOS: 5, 6, 13 and 14 and sequences complementary thereto, wherein the base sequence of said oligomers comprises at least one CpG dinucleotide.

It is also preferred that said set of MSP primer oligonucleotides further includes at least two oligonucleotides whose sequences comprise a sequence having a length of at least 9 nucleotides which hybridizes to a pretreated nucleic acid sequence according to one or more of SEQ ID NOS:7-20.

Step e) of the method, namely the analysis of the specific amplificates indicative of the methylation status of one or more CpG positions according to SEQ ID NO:1, and in further embodiments of one or more CpG positions according to SEQ ID NOS:2-4 is carried out by means of real-time prognosis methods as described above.

In an alternative most preferred embodiment of the method the subsequent amplification of d) is carried out in the presence of blocking oligonucleotides, as described above. Said blocking oligonucleotides comprising a sequence having a length of at least 9 nucleotides which hybridizes to a pretreated nucleic acid sequence according to one of SEQ ID NOS: 5, 6, 13 and 14 and sequences complementary thereto.

In a further embodiment it is preferred that said set of blocking oligonucleotides includes at least one oligonucleotides sequence having a length of at least 9 nucleotides which hybridizes to a pretreated nucleic acid sequence according to one of SEQ ID NOS: 5, 6, 13 and 14 and sequences complementary thereto and furthermore at least one oligonucleotides sequence having a length of at least 9 nucleotides which hybridizes to a pretreated nucleic acid sequence according to one of SEQ ID NOS:7-20.

Step e) of the method, namely the prognosis of the specific amplificates indicative of the methylation status of one or more CpG positions according to SEQ ID NOS:1 to SEQ ID NO:4 is carried out by means of real-time prognosis methods as described above.

Additional embodiments of the invention provide a method for the analysis of the methylation status of genomic DNA according to the invention (SEQ ID NO:1, and in further embodiments SEQ ID NOS:2 to SEQ ID NO:4, and complements thereof) without the need for pretreatment.

It is preferred that the methylation of at least one CpG dinucleotide of SEQ ID NO:1 is analysed. In a further embodiment the methylation staus of at least one CpG dinucleotide of SEQ ID NO:1 and one or more sequences selected from the group consisting SEQ ID NOS: 2-4 are analysed.

In the first step of such additional embodiments, the genomic DNA sample is isolated from tissue or cellular sources. Preferably, such sources include colon cell lines, histological slides or tissue embedded in paraffin. In the second step, the genomic DNA is extracted. This may be by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

In a preferred embodiment, the DNA may be cleaved prior to the treatment, and this may be by any means standard in the state of the art, in particular with methylation-sensitive restriction endonucleases.

In the third step, the DNA is then digested with one or more methylation sensitive restriction enzymes. The digestion is carried out such that hydrolysis of the DNA at the restriction site is informative of the methylation status of a specific CpG dinucleotide.

In the fourth step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels.

In the fifth step the amplificates are detected. The prognosis may be by any means standard in the art, for example, but not limited to, gel electrophoresis analysis, hybridization analysis, incorporation of detectable tags within the PCR products, DNA array analysis, MALDI or ESI analysis.

In the final step of the of the method the presence or absence of colon cell proliferative disorder is deduced based upon the methylation state of at least one CpG dinucleotide sequence of the analysed genes. Most preferably the presence or absence of colon cell proliferative disorder is deduced based upon the methylation state of at least one CpG dinucleotide sequence of SEQ ID NO1 or an average, or a value reflecting an average methylation state of a plurality of CpG dinucleotide sequences of SEQ ID NO1. In a further embodiment the presence or absence of colon cell proliferative disorder is deduced based upon the methylation state of at least one CpG dinucleotide sequence of SEQ ID NO1 and at least one sequences selected from SEQ ID NOS:2-4 or an average, or a value reflecting an average methylation state of a plurality of CpG dinucleotide sequences of SEQ ID NO1 and at least one sequences selected from SEQ ID NOS:2-4.

Prognostic Assays for Colon Cell Proliferative Disorders

The present invention enables prognosis of events which are disadvantageous to patients or individuals with colon cancer by analysis of aberrant genomic methylation patterns. Most preferably such a prognosis is based on important genetic and/or epigenetic parameters within the gene APC and/or its regulatory sequences, including that according to SEQ ID NO: 1 alone or in combination with at least one sequence selected from the group consisting SEQ ID NOS:2 to 4 may be used as markers. Said parameters obtained by means of the present invention may be compared to another set of genetic and/or epigenetic parameters, the differences serving as the basis for a diagnosis and/or prognosis of events which are disadvantageous to patients or individuals.

Specifically, the present invention provides for diagnostic cancer assays based on measurement of differential methylation of one or more CpG dinucleotide sequences of genomic sequences. In a preferred embodiment said sequence being SEQ ID NO:1 alone or in combination with at least one sequence selected from the group consisting SEQ ID NOS:2 to 4, or of subregions thereof that comprise such a CpG dinucleotide sequence. Typically, such assays involve obtaining a tissue sample from a test tissue, performing an assay to measure the methylation status of at least one of one or more CpG dinucleotide sequences of SEQ ID NO:1 alone or in combination with at least one sequence selected from the group consisting SEQ ID NOS:2 to 4 and derived from the tissue sample, relative to a control sample, or a known standard and making a diagnosis or prognosis based thereon.

In particular preferred embodiments, inventive oligomers are used to assess the CpG dinucleotide methylation status, such as those based on SEQ ID NO:1 alone or in combination with at least one sequence selected from the group consisting SEQ ID NOS:2 to 4 and, as well as in kits based thereon and useful for the diagnosis and/or prognosis of colon cell proliferative disorders.

Kits

Moreover, an additional aspect of the present invention is a kit comprising, for example: a bisulfite-containing reagent; a set of primer oligonucleotides containing at least two oligonucleotides whose sequences in each case correspond, are complementary, or hybridize under stringent or highly stringent conditions to a 16-base long segment of the sequences SEQ ID NOS: 1, 5, 6, 7, 13 and 14 alone or in combination with at least one sequence selected from the group consisting SEQ ID NOS:2 to 4, 7 to 20,; oligonucleotides and/or PNA-oligomers; as well as instructions for carrying out and evaluating the described method.

In a further preferred embodiment, said kit may further comprise standard reagents for performing a CpG position-specific methylation analysis, wherein said analysis comprises one or more of the following techniques: MS-SNuPE™, MSP, MethyLight®, HeavyMethyl™, COBRA™, and nucleic acid sequencing. However, a kit along the lines of the present invention can also contain only part of the aforementioned components.

Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Typical reagents (e.g., as might be found in a typical MethyLight®-based kit) for MethyLight® analysis may include, but are not limited to: PCR primers for specific gene (or methylation-altered DNA sequence or CpG island); TaqMan® probes; optimized PCR buffers and deoxynucleotides; and Taq polymerase.

Typical reagents (e.g., as might be found in a typical Ms-SNuPE-based kit) for Ms-SNuPE™ analysis may include, but are not limited to: PCR primers for specific gene (or methylation-altered DNA sequence or CpG island); optimized PCR buffers and deoxynucleotides; gel extraction kit; positive control primers; Ms-SNuPE™ primers for specific gene; reaction buffer (for the Ms-SNuPE™ reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

The described invention further provides a composition of matter useful for determining the presence of metastasis of colon cell proliferative disorders or determining likelihood of development thereof. Said composition comprising at least one nucleic acid 18 base pairs in length of a segment of the nucleic acid sequence disclosed Table 1, and one or more substances taken from the group comprising: magnesium chloride, dNTP, taq polymerase, bovine serum albumen. It is preferred that said composition of matter comprises a buffer solution appropriate for the stabilization of said nucleic acid in an aqueous solution and enabling polymerase based reactions within said solution. Suitable buffers are known in the art and commercially available. It is particularly preferred that the composition of matter comprises one of the following groups of nucleic acids SEQ ID NO: 21-23; SEQ ID NO:24-26; SEQ ID NO:27-29; SEQ ID NO:30-32; SEQ ID NO:33-35; SEQ ID NO:36-38; SEQ ID NO:39-41; SEQ ID NO:42-44. Particularly preferred is a composition of matter comprising SEQ ID NO:36-38.

While the present invention has been described with specificity in accordance with certain of its preferred embodiments, the following example serves only to illustrate the invention and is not intended to limit the invention within the principles and scope of the broadest interpretations and equivalent configurations thereof.

Example 1

Subjects

Metastatic lesions were obtained from 24 patients (13 male, 11 female, median age 64.5 yrs, range 41-79) with colorectal cancer that developed liver metastasis after prior successful colon cancer resection. In 2 patients the primary colon cancer and a single liver metastasis were resected at the same time. Primary colon cancer tissue was obtained by surgical resection from 39 patients (26 male, 13 female; median age of 74 years, range 40-93 years) with sporadic colorectal cancer. In 14 of these patients corresponding non-cancer colon tissue was also obtained from a tumor-free location which was at least 2 cm distant from the tumor and which was confirmed to be without any tumor cell infiltration by histology. Immediately after surgery, tissue samples were put in liquid nitrogen and stored at −80° C. until use. Formalin fixed tissues were processed as previously described and sections were stained with hematoxylin and eosin (H&E) for histological evaluation. Tumor stages were assessed using the TNM-system.

DNA Extraction

Genomic DNA of all samples was extracted from the tissues using the proteinase K digestion method.

Western blot Analysis

Sixteen patients were selected for the analysis. from the non-tumorous colon, colon cancer and liver metastases were lysed in a buffer containing 1 mM EDTA, 50 mM β-glycerophosphate, 2 mM sodium orthovanadate, 1% Triton-100, 10% glycerol, 1 mM DTT and protease inhibitors (10 mg/ml benzamidine, 2 mg/ml antipain, and 1 mg/ml leupeptin). The protein concentration of the supernatants was determined by the BCA assay (Bio-rad). Twenty µg protein of each sample was adjusted to Laemmli buffer composition [2% SDS, 10% glycerol, 62.5 mM Tris-HCl (pH 6.8), 100 mM DTT, and 0.1% bromphenol blue], denatured by heating at 95° C. for 5 min, and subsequently separated on 5% polyacrycamide gels by SDS-gel electrophoresis. After separation, proteins were transferred onto immuno-Blot polyvinylidene difluoride (PVDF) membrane (Bio-rad). The membrane was blocked in 5% non-fat milk in 1% TBST for 1 h at room temperature, and then incubated with 1:200 anti-APC(C-20) antibody (Santa Cruz Biotechology, Santa Cruz, Calif.) overnight at 4° C. Membranes were then washed three times in Tris-buffered saline/0.1% Tween 20, incubated for 2 h with peroxidase-labeled anti-rabbit IgG (1:2500, KPL) diluted in blocking solution. Membrane-bound secondary antibodies were detected by an enhanced chemiluminescence method following the instructions of the manufacturer (ECL plus western blotting detection reagents, Amersham Biosciences).

Figure 2:
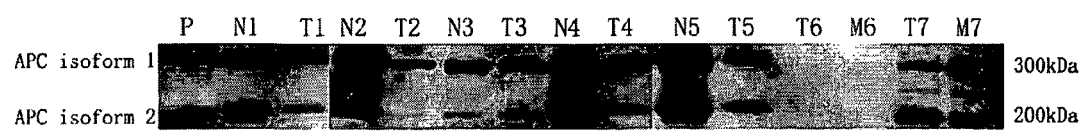
Figure 3:
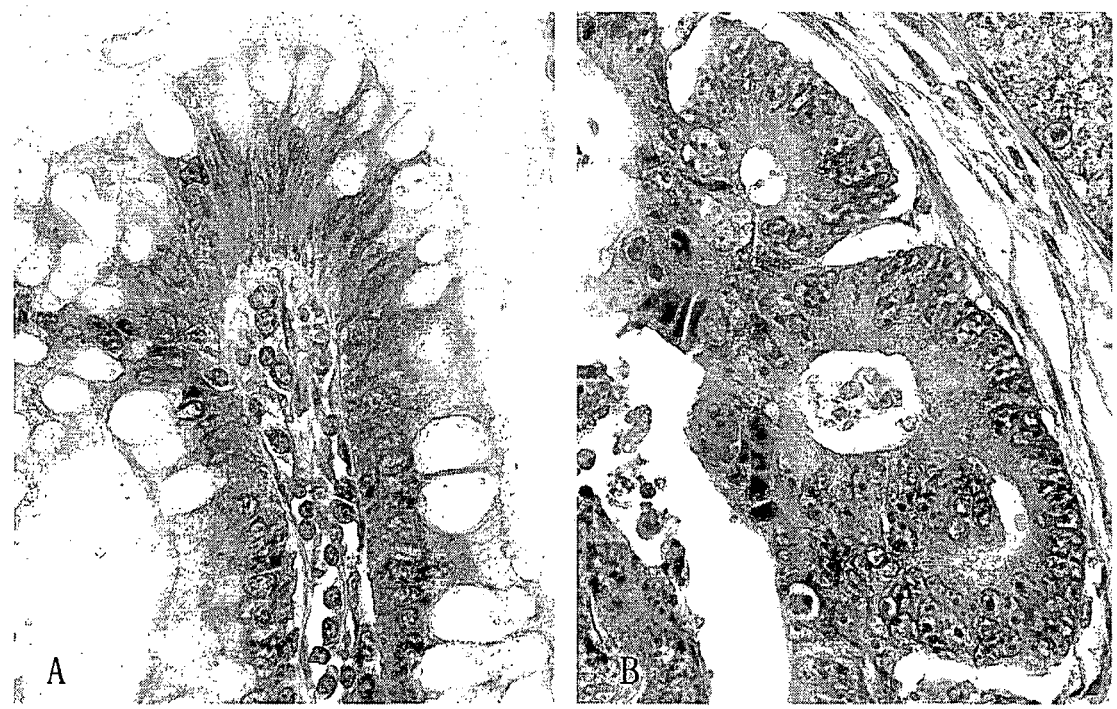

In the Western blot analysis, two isoforms of the APC protein (300 and 200 kDa, respectively) were observed while no truncated APC proteins was detected. In general, the level of both APC isoforms was decreased in 10 primary cancer tissues when compared with the corresponding normal colon tissues. However, APC protein levels were similar in 2 liver metastases and increased in 2 liver metastases when compared with the corresponding normal colon tissues. In one matched primary colon cancer and liver metastasis tissues the expression of APC protein was completely absent, while in one case APC protein levels were higher in the liver metastasis than in corresponding primary colon cancer. Furthermore, when we compared the APC protein levels in tumor tissues with the presence of APC promoter methylation, we observed no significant difference among the tissues with methylation of the APC promoter versus cases without methylation. (Table 1, FIG. 2).

Immunohistochemistry

The distribution and expression pattern of APC protein in 12 out of these 16 patients selected for western blot analysis were also investigated by immunohistochemistry. Tissue samples used for immunohistochemistry analysis had been obtained after surgery, fixed in 10% neutralized formalin and embedded in paraffin. Deparaffinized sections were stained using H&E. For immunostaining of paraffin-embedded sections, the slides were deparaffinized and rehydrated in a graded alcohol series. Immunostaining was performed with the anti-APC(C-20) antibody (Santa Cruz, Calif.) directed against human APC (dilution 1:20). Incubation with the primary antibody was performed in a moist chamber at 37° C. for 1 hour. Polyvalent anti-rabbit IgG (30 min, room temperature; Immunotech, Marseilles, France) served as a secondary anti-body. Slides were washed between steps with Tris-buffered saline. Immunoreactions were visualized via a streptavidin-biotin complex, using the Vectastain ABC alkaline phosphatase kit (distributed by CAMON, Wiesbaden, Germany). Neufuchsin (Sigma-Aldrich, Steinheim, Germany) served as chromogen. The specimens were counter-stained with hematoxylin. Primary antibodies were omitted for negative controls. Evaluation of the slides was performed by an experienced pathologist who was blinded to the results of the methylation analysis (see below). Immunostaining was graded semiquantitatively as negative, weak, moderate, or strong corresponding to positive staining of 0%, <10%, 10-50%, or more than 50% of the total cells.

Results. APC was found in the cytoplasm of each of the samples obtained from non-tumorous mucosal epithelium, tumorous epithelium of the primary tumor site, lymph node metastases and liver metastases. The intensity of immunostaining and the number of immunoreactive cells was decreased in tumorous epithelium of 5 patients, when compared with the corresponding non-tumorous epithelium. The expression of APC was similar in tumorous and non-tumorous epithelium of 3 patients, as well as in the primary tumor and lymph node metastases of 4 patients.

MethyLight Analysis of APC Gene

Methylation analysis of genomic DNA of all samples was analyzed by the MethyLight™ technique after bisulfite conversion as previously reported by Eads et al. (Eads, C. A., Danenberg, K. D., Kawakami, K., Saltz, L. B., Blake, C., Shibata, D., Danenberg, P. V., Laird, P. W. (2000) Methy Light: a high-throughput assay to measure DNA methylation. *Nucleic Acids Res., 28,* E32).

Briefly, two locus-specific PCR primers flank an oligonucleotide probe with a 5' fluorescent reporter dye (6FAM) and a 3' quencher dye (BHQ-1). For this analysis primers and probes are specifically designed to bind to bisulfite-converted DNA, which generally span 7 to 10 CpG dinucleotides. The gene of interest is then amplified and normalized to a reference set (β-actin). The specificity of the reactions for methylated DNA is confirmed using unmethylated human sperm DNA and CpGenome Universal Methylated DNA (Chemicon Inc.). TaqMan PCR reactions are performed in parallel with primers specific for the bisulfite-converted methylated sequence for a particular locus and with the ACTB reference primers. The ratio between the values is calculated in these two TaqMan analyses. The extent of methylation at a specific locus is determined by the following formula: [(gene/actb) sample: (gene/actb) SssI-treated genomic DNA]*100. A cut off value of 4% gave the best discrimination between normal and cancerous samples, as previously reported. Therefore, samples with ≧4% fully methylated molecules were termed methylated, whereas samples with <4% were considered unmethylated. The primer and probe sequences for APC promoter analysis (GeneBank accession number U02509) are: forward primer (5'-3'): GAA CCA AAA CGC TCC CCA T SEQ ID NO: 36; reverse primer (5'-3'): TTA TAT GTC GGT TAC GTG CGT TTA TAT SEQ ID NO: 37; probe sequence (5'-3'): 6FAM-CCC GTC GAA AAC CCG CCG ATT A-BHQ1 SEQ ID NO: 38 (as listed in Table 1).

Statistical Analysis

The PMR (percentage of methylated reference) values of the Methylight™ assays were dichotomized for statistical purposes as previously reported by Eads et al. The frequency of APC promoter methylation in primary and metastatic colon cancers was compared by Fisher's exact test. All tests were two-sided, and a p-value of <0.05 was considered statistically significant.

Results. Using the Methylight assay, the promoter 1A methylation status of the APC gene in 39 primary colon cancers and 14 corresponding samples from non-neoplastic colon mucosa was assesed. Seven cancers exhibited a PMR>4% (7/39) APC promoter methylation was not observed in any of the 14 non neoplastic colon samples (FIG. 1A). The frequency of APC promoter methylation in 24 liver metastases was then assessed and compared with the frequency thereof in the 39 primary colon cancers. In this series, primary colon cancer and liver metastases were obtained from the same patients in two cases, while the remaining 22 liver metastasis and 37 primary colon cancer samples were obtained from separate patient populations. The analysis showed a higher frequency of APC promoter methylation in metastatic colon cancer (10/24) compared with primary colon cancer (7/39) (p=0.047), although in the two matched primary colon cancer and metastatic tissues, no APC promoter methylation was observed in both the primary cancer and liver metastasis (FIG. 1B).

Using the Methylight assay, APC promoter 1A methylation was observed in 7 of 39 (17.95%) primary colorectal cancers and in none of the matched non-neoplastic colon mucosa samples. Furthermore, a significantly higher frequency (41.67%) of APC promoter methylation in liver metastases of colorectal cancers was observed.

Although the majority of the primary cancers and the liver metastases in this study were from different patients, the fact that APC promoter was more frequently methylated in the liver metastases of colon cancer still indicates that the epigenetic change of the APC gene plays a role in the progression of colorectal cancer. There are two possibilities for the contribution of APC promoter methylation to the metastasis of colorectal cancer; one possibility is that methylation of APC gene promoter occurs early in colorectal cancer and increases during disease progression. Moreover, our results also indicate the other possibility that methylation of the APC gene promoter may occur de novo in the metastatic cancer cells even in the absence of methylation in the primary cancer cells.

Furthermore, APC protein expression in a subset of primary and metastatic colorectal cancer samples was analysed. By Western blot analysis, two isoforms of the APC protein (300 and 200 kDa, respectively) were observed in all non-neoplastic colon mucosa samples, primary tumors and liver metastases. The 300 kDa isoform is the conventional form of the APC protein encoded by exons 1-15 and is critical for the differentiation of intestinal epithelial cells; while the 200 kDa isoform is an alternative splice-form of APC without exon 1 that has been shown to be enriched in non-dividing, terminally-differentiated cells and may contribute to suppression of proliferation (27, 28). In general, the levels of both APC isoforms was decreased in primary cancer tissues when compared with corresponding non-neoplastic mucosa, but APC levels in colon cancer metastases were similar or even increased compared with corresponding non-neoplastic mucosa or primary cancers. The APC protein distribution pattern in non-neoplastic mucosa, colon cancer and liver metastases was also confirmed by immunohistochemistry. Thus, although the APC promoter was more frequently methylated in the liver metastases of colon cancer, there was no significant association between APC promoter methylation and APC protein expression in metastases. From these results it is possible to infer that metastatic cancer cells seem to harbour a heterogenous epigenetic background, in which only few cells exhibit APC promoter methylation. As the Methylight™ assay detected APC promoter methylation more frequently in metastases compared to primary cancers, this result indicates the presence of methylation independent of the number of cancer cells exhibiting APC methylation. In contrast, APC protein expression was determined in a tissue homogenate including cells with and without APC methylation. Therefore, despite the fact that APC methylation may be detected in these cancer cells, other cancer cells may retain APC expression due to a normal APC gene. Apart from that, even in cells with APC promoter methylation, only one allele may be affected, which may still allow the expression of the unmodified allele.

In summary, it is demonstrated that APC promoter methylation is a frequent epigenetic alteration in colorectal cancer metastases. However, the levels of the APC protein may remain unchanged indicating that metastatic cancer cells seem to either harbour a heterogenous epigenetic background, in which only few cells exhibit APC promoter methylation and others retain APC expression, or that the unaltered second allele still allows sufficient APC expression.

In a further analysis the methylation status of known colon cancer associated marker genes TPEF, p16, TIMP3, DAPK and Caveolin 2 and a novel methylation marker ALX4 were analysed in normal, colon and colon metastasis using the MethyLight™ assay as described above, with primers and probes according to Table 1. See Table 3 for results of methylation Methylight™ assays and Table 4 for comparisons of methylation, Western Blot and Immunohistological APC analyses.

TABLE 1

List of primers and probes used for Methylight analysis

| Gene | forward primer (5'-3') | reverse primer (5'-3') | probe sequence (5'-3') |
|---|---|---|---|
| ALX4 | CGCGGTTTCGATTT TAATGC SEQ ID NO: 21 | ACTCCGACTTAACC CGACGAT SEQ ID NO: 22 | 6FAM-CGACGAAATTCCTA ACGCAACCGCTTA A-BHQ1 SEQ ID NO: 23 |
| Caveolin 2 | TTTCGGATGGGAAC GGTGTA SEQ ID NO: 24 | CTCCCACCGCCGTT ACC SEQ ID NO: 25 | 6FAM-CCCGTCCTAACCGT CCGCCCT-BHQ1 SEQ ID NO: 26 |
| DAPK | TCGTCGTCGTTTCG GTTAGTT SEQ ID NO: 27 | CCCTCCGAAACGCT ATCGA SEQ ID NO: 28 | 6FAM-CGACCATAAACGCC AACGCCG-BHQ1 SEQ ID NO: 29 |
| TPEF | TTTTTTTTTCGGAC GTCGTTG SEQ ID NO: 30 | CCTCTACATACGCC GCGAAT SEQ ID NO: 31 | 6FAM-AATTACCGAAAACA TCGACCGA-BHQ1 SEQ ID NO: 32 |
| p16/INK4A | TGGAATTTTCGGTT GATTGGTT SEQ ID NO: 33 | AACAACGTCCGCAC CTCCT SEQ ID NO: 34 | 6FAM-ACCCGACCCCGAAC CGCG-BHQ1 SEQ ID NO: 35 |
| APC | GAACCAAAACGCTC CCCAT SEQ ID NO: 36 | TTATATGTCGGTTA CGTGCGTTTATAT SEQ ID NO: 37 | 6FAM-CCCGTCGAAACCC GCCGATTA-BHQ1 SEQ ID NO: 38 |

TABLE 1-continued

List of primers and probes used for Methylight analysis

| Gene | forward primer (5'-3') | reverse primer (5'-3') | probe sequence (5'-3') |
|---|---|---|---|
| TIMP3 | GCGTCGGAGGTTAA GGTTGTT SEQ ID NO: 39 | CTCTCCAAAATTAC CGTACGCG SEQ ID NO: 40 | 6FAM-AACTCGCTCGCCCG CCGAA-BHQ1 SEQ ID NO: 41 |
| Caveolin | TTTCGGATGGGAAC GGTGTA SEQ ID NO: 42 | CTCCCACCGCCGTT ACC SEQ ID NO: 43 | 6FAM-CCCGTCCTAACCGT CCGCCCT-BHQ1 SEQ ID NO: 44 |

TABLE 2

Genes and sequences according to the invention.

| Gene name | Genomic SEQ ID NO | Methylated treated SEQ ID NOs: | Unmethylated treated SEQ ID NOs: |
|---|---|---|---|
| APC | 1 | 5 & 6 | 13 & 14 |
| ALX4 | 2 | 7 & 8 | 15 & 16 |
| TPEF | 3 | 9 & 10 | 17 & 18 |
| p16 | 4 | 11 & 12 | 19 & 20 |
| DAPK | 45 | 48 & 49 | 54 & 55 |
| TIMP3 | 46 | 50 & 51 | 56 & 57 |
| Caveolin 2 | 47 | 52 & 53 | 58 & 59 |

TABLE 3

Summary of results from analysis of gene methylation in primary cancer and metastasis.

| Gene | Normal (n = 21) | Tumor (n = 47) | Metastasis (n = 24) |
|---|---|---|---|
| ALX4 | 0/21 | 30/47 | 16/24 |
| TPEF | 1/21 | 36/47 | 19/24 |
| p16 | 0/21 | 15/47 | 6/24 |
| APC | 0/21 | 10/47 | 10/24 |
| TIMP3 | 1/21 | 11/47 | 2/24 |
| DAPK | 0/21 | 1/47 | 0/24 |
| Caveolin 2 | 0/21 | 5/47 | 1/24 |

TABLE 4

Expression of APC protein in colon cancer: patient characteristics and molecular changes.

| | | | Methylation | | | Western blot | | | Immunohistochemistry | | |
|---|---|---|---|---|---|---|---|---|---|---|---|
| No | Age | Sex | T | M | | N | T | M | N | T | M |
| 1 | 61 | M | + | | | ++ | + | | +++ | +++ | +++[a] |
| 2 | 51 | F | + | | | ++ | + | | +++ | + | +[a] |
| 3 | 66 | F | − | | | ++ | + | | ND | +++ | +++[a] |
| 4 | 63 | M | + | | | ++ | + | | +++ | +++ | ND |
| 5 | 62 | F | + | | | ++ | + | | +++ | +++ | ND |
| 6 | 55 | M | − | | | ++ | + | | ND | ND | ND |
| 7 | 59 | M | − | | | ++ | ++ | | ND | ND | ND |
| 8 | 64 | M | − | | | ++ | + | | +++ | +++ | ND |
| 9 | 49 | M | − | | | ++ | + | | +++ | ++ | +[a] |
| 10 | 77 | F | − | | | ++ | + | | +++ | ++ | ND |
| 11 | 52 | F | | + | | ++ | | ++ | +++ | ++ | ND |
| 12 | 70 | M | | + | | + | | ++ | ND | ND | ++[b] |
| 13 | 79 | F | | − | | + | | ++ | ND | ND | +[b] |
| 14 | 65 | M | | − | | ++ | | ++ | ND | ND | +++[b] |

TABLE 4-continued

Expression of APC protein in colon cancer: patient characteristics and molecular changes.

| No | Age | Sex | Methylation | | | Western blot | | | Immunohistochemistry | | |
|----|-----|-----|---|---|---|---|---|---|---|---|---|
| | | | T | M | N | T | M | N | T | M | |
| 15 | 43 | F | – | | | – | – | | ND | ND | ND |
| 16 | 74 | F | – | | | + | ++ | | ND | ND | ND |

Legend:
M, male;
F, female;
N, normal colon;
T, colon cancer;
M, metastasis;
[a], Lymph node metastasis;
[b], liver metastasis;
ND, not determined;
+, positive;
–, negative.
Immunohistochemical analysis:
–, negative;
+, <10% expression;
++, 10-50% expression;
+++, >50% expression.

The invention claimed is:

1. A method for the detection of metastasis or the likelihood of metastasis of colon cell proliferative disorders, comprising:
    obtaining, from a subject, a biological sample having subject genomic DNA;
    determining, using the genomic DNA, a CpG methylation status of at least one CpG dinucleotide of each the TPEF and p16/INK4A gene sequences; and
    determining, from said determined methylation status the presence or absence of a metastasis or likelihood thereof of a colon cell proliferative disorder, wherein an increase in methylation status as compared to the status from genomic DNA of a subject not having a colon cell proliferative disorder is indicative of metastasis or likelihood thereof.

2. The method of claim 1, wherein said metastasis is located in the liver.

3. The method of claim 1, comprising:
    obtaining, from a subject, a biological sample having subject genomic DNA;
    contacting the genomic DNA, or a fragment thereof, with one reagent or a plurality of reagents suitable for distinguishing between methylated and non methylated CpG dinucleotide sequences within at least one target sequence of each of the TPEF and p16/INK4A gene sequences or portions thereof, wherein the target sequences comprise, or hybridize under stringent conditions to, at least 16 contiguous nucleotides of SEQ ID NOS:3 and 4, respectively, said contiguous nucleotides thereof comprising at least one CpG dinucleotide sequence; and determining, based at least in part on said distinguishing, the methylation state of at least one TPEF target CpG dinucleotide sequence and at least one p16/INK4A target CpG dinucleotide sequence, or an average, or a value reflecting an average methylation state of a plurality of TPEF and p16/INK4A target CpG dinucleotide sequences, wherein detecting metastasis of colon cell proliferative disorders is afforded.

4. The method of claim 3, wherein distinguishing between methylated and non methylated CpG dinucleotide sequences within the at least one target sequence of each of TPEF and p16/INK4A comprises converting unmethylated cytosine bases within the target sequence to uracil or to another base that is detectably dissimilar to cytosine in terms of hybridization properties.

5. The method of claim 4, wherein the biological sample is at least one selected from the group consisting of colon cell lines, histological slides, biopsies, paraffin-embedded tissue, and combinations thereof.

6. The method of claim 4, wherein distinguishing between methylated and non methylated CpG dinucleotide sequences within the at least one target sequence of each of TPEF and p16/INK4A comprises use of at least one nucleic acid molecule or peptide nucleic acid (PNA) molecule comprising, in each case, a contiguous sequence at least 9 nucleotides in length that is complementary to, or hybridizes under moderately stringent or stringent conditions to a sequence selected from the group consisting of SEQ ID NOS:9, 10, 17 and 18, and SEQ ID NOS:11,12, 19 and 20, and complements thereof, respectively.

7. A method for the detection of metastasis or the likelihood of metastasis of colon cell proliferative disorders, comprising:

obtaining, from a subject, a biological sample having subject genomic DNA;

extracting or otherwise isolating the genomic DNA;

treating the extracted or otherwise isolated genomic DNA, or a fragment thereof, with one or more reagents to convert cytosine bases that are unmethylated in the 5-position thereof to uracil or to another base that is detectably dissimilar to cytosine in terms of hybridization properties;

contacting the treated genomic DNA, or the treated fragment thereof, with an amplification enzyme and at least two pairs of primers, wherein one pair comprises, for each primer of the pair, at least one contiguous sequence of at least 9 nucleotides that is complementary to, or hybridizes under moderately stringent or stringent conditions to a sequence selected from the TPEF group consisting of SEQ ID NOS:3, 9, 10, 17 and SEQ ID NO:18, and complements thereof, and wherein a second pair of primers comprises, for each primer of the pair, at least one contiguous sequence of at least 9 nucleotides that is complementary to, or hybridizes under moderately stringent or stringent conditions to a sequence selected from the p16/INK4A group consisting of SEQ ID NOS:4, 11, 12, 19 and SEQ ID NO:20, and complements thereof, wherein the treated genomic DNA or the portion thereof is either amplified to produce at least one amplificate, or is not amplified; and determining, based on a presence or absence of, or on a property of said amplificate, the methylation state of at least one CpG dinucleotide sequence of SEQ ID NO:3 and of at least one CpG dinucleotide sequence of SEQ ID NO:4, or an average, or a value reflecting an average methylation state of a plurality of CpG dinucleotides of SEQ ID NO:3 and SEQ ID NO:4, wherein the detection of metasasis or the likelihood of metastasis of colon cell proliferative disorders is afforded.

8. The method of claim 7, wherein treating the genomic DNA, or the fragment thereof, comprises use of a reagent selected from the group consisting of bisulfite, hydrogen sulfite, disulfite, and combinations thereof.

9. The method of claim 7, wherein contacting or amplifying comprises use of at least one method selected from the group consisting of: use of a heat-resistant DNA polymerase as the amplification enzyme; use of a polymerase lacking 5'-3' exonuclease activity; use of a polymerase chain reaction (PCR); generation of a amplificate nucleic acid molecule carrying a detectable labels; and combinations thereof.

10. The method of claim 9, wherein said nucleic acid molecule or peptide nucleic acid molecule is in each case modified at the 5'-end thereof to preclude degradation by an enzyme having 5'-3' exo nuclease activity.

11. The method of claim 9, wherein said nucleic acid molecule or peptide nucleic acid molecule is in each case lacking a 3' hydroxyl group.

12. The method of claim 11, wherein the amplification enzyme is a polymerase lacking 5'-3' exo nuclease activity.

13. The method of claim 7, wherein determining comprises hybridization of at least one nucleic acid molecule or peptide nucleic acid molecule in each case comprising a contiguous sequence at least 9 nucleotides in length that is complementary to, or hybridizes under moderately stringent or stringent conditions to a sequence selected from the group consisting of SEQ ID NOS:9, 10, 17 and 18, and SEQ ID NOS:11,12, 19 and 20, and complements thereof, respectively.

14. The method of claim 13, further comprising extending at least one such hybridized nucleic acid molecule by at least one nucleotide base.

15. The method of claim 7, wherein determining comprises sequencing of the amplificate.

16. The method of claim 7, wherein contacting or amplifying, comprises use of methylation-specific primers.

* * * * *

SEQUENCE LISTING

<160> NUMBER OF SEQ ID NOS: 59

<210> SEQ ID NO 1
<211> LENGTH: 2470
<212> TYPE: DNA
<213> ORGANISM: Homo Sapiens

<400> SEQUENCE: 1

```
aaagatgatt aaaagtttaa ttgttcatct gaagagttga ttttttatt cctgtaataa      60
agggtacttt tagcagtctc tgctcatctt gcccatccgg ctcttttgt ggttgtgtaa    120
ggttataact tctgtgtctc agtaaacttg tgcatgccca ttttttctc tgttactacc   180
ttttctctta ttttgtttta ttattttgat gtaaaattac ctgttaattt tatttgaaat   240
gagaaatttt aaggttcaca ttattcaaat tctgtcagat ccctacctct gtcatatggt   300
ttataatgtg ctgggtattt tcagacctgc ttattaaaaa gatgtaaaac aaaataatga   360
tcactcctgt ggatttttcc tttattttg agatgtctcc tttggctgca ttacttcttc   420
acccttgcc cattgatcag aggaggggtc ttaactatgg gtgaacccta tatcttactg    480
aagaggttat gttacatgta tattttcata atataactta catttacata gtactttat    540
ttttagcata cctttttta ttaatcctaa taatatcact gtaagttatg ttgaagcaga    600
ttgtaagtgt tcatttacaa attgtgaaat gaattaaaat gaaagggcaa agattaaatc    660
atgaccaggc ctgaaattaa cacacaagac tcaattttt tcaaccaaag acttttgtag    720
gtgatccctg cctgcaggac tccccttcct cctcagatgt cattggattg taccaggttt    780
actgtagatt ctagccgttg tagaactaac tagatctaag atgagtcccc tgatttcctt    840
tggtagagtc ttccaattgc tgaactccaa tattgtcgtg actagccagt gttcaacct    900
gtctgcctta ttttgtgtaa tggatttcat attacagagg catttttta atgtcaagat    960
gtttaagtat tgcttaagtg caaactactt aatactttt agctattaag taattaagat   1020
aggcaggatt ttatttgttc caaaatgatt tgacctaaac taaaagaga atgtggatct   1080
cctgaatctt acttggttaa tcttaatata actcctagca ttctataatt cttcctaaag   1140
```

```
tcctcttacc tggctatctt ttgtatcttc tttgtctctc ctcttctttc ccagtcataa    1200
taactgccag actctgcttc atttctcttt gacagtctct actcctaagg tcatccattc    1260
tctttaggta tcttttggcc tcagtttgag cacagcagat cccaagacca catatgccat    1320
agcataggct attatagtca accttttgaa taaatgtgat tgaactttat gttagtaatt    1380
cttatttacc atcttcctat caaaaaggct taaagtcttc atttaatgct ctccttcatg    1440
tccattttgt taaatgattg cctttttaatg acatcttaga acttcagaac tatttcacca   1500
tggaggatgt gtaagattag cctttttatca aataaaaagt gtgaaatgga atatgtaatc   1560
tcattaatcc attctggctc taaaattctg tgactatcag ataaaattca gaaataaaat    1620
agtattacta atataaataa attttttatca taattatatt tcctaagttt tgcctgtaag   1680
aatgggtaaa atatctttaa aaccttgaag aaattattac ttgatagaaa gtttaatcca    1740
tctgtgagaa ggcaaatgta ttcagacaca actaaagttc tctcttctat tttaatttca    1800
tttatcttga actaagactc cactgtttca tcctcttaga tgctgctact tgaacaatat    1860
tgttttgaga ccaaaaacta gcatattaac acaattcttc ttaaacgtct taagagtttt    1920
gtttcccttta cccctttctt taaaaacaag cagccactaa attttttagt agtgaatttc   1980
aaaatccttt ttaaccttat aggtccaagg gtagccaagg atggctgcag cttcatatga    2040
tcagttgtta aagcaagttg aggcactgaa gatggagaac tcaaatcttc gacaagagct    2100
agaagataat tccaatcatc ttacaaaact ggaaactgag gcatctaata tgaaggtatc    2160
aagactgtga cttttaattg tagtttatcc atttttattc agtattccct cttgtaaact    2220
tgaggtaaga cactttactt aaaagtgtat tttaaattaa gcaataatat gtaaactctt    2280
tcttgcaaaa gttagcattt atattttaa ataagatata ttgaattcat tcagtgaatc     2340
atataaagaa aataagtgta aaactccaat ggctagttag ttcttagttc tttttaagat    2400
taaagagaag agaccaaata tagcatcact gtactgaggc aaggttttct gtgtagttca    2460
tagaaactag                                                           2470

<210> SEQ ID NO 2
<211> LENGTH: 2229
<212> TYPE: DNA
<213> ORGANISM: Homo Sapiens

<400> SEQUENCE: 2
tctttcctcg gcgctggctg gtgcgggttg gggtcaggtg gagaagccgc tctttgttaa      60
ggtgacagaa cgtgctgggg gtgggggccg gggccagggc cggtgcaact agggggccgc     120
tgccctttcc tggacacagt ggaagcttct tccgcatcac caaattttg tcatcctttc      180
tgagggacct gcttccaggc agcacgcaag ttgttgtccc gggtttactc cgcacccctc     240
tactgggtga ggaaggagca tcttgaatgg agatgggggt gtccccggtt tatacatctg     300
cagagaagag gtgtgccggg ctgcacctct ggaggccgcg gtaactgata ttagagaaga     360
ccccggttgc agctgggaag gctcactggc tggaagagg tgcctcctcc ttccagcaaa      420
gggccctgtt tggaagggct gcttctcacc tgtctagtgg caccacagga cggtcggctt     480
ccactcgaat tccccggac ggtatcatca catagccggg tcctcgcagt gttggtttcc      540
caatccgatg actgtcacct cggtgaggac ctgtgctgat ggccggagaa ccctgcgctg     600
cgggcgcaca tggccaggtg gcgcctggca ggcgacgtcc gggtgcagga cggcgctctt     660
accgccccac cccaaaccgt tgcctgggcc taggtccttc ggcttcctga acaggggttt     720
gggggggctaa ggacgctgag gctccggggg caggaagttc tctctggtta agcgttctct    780
```

-continued

| | |
|---|---|
| cttctctccg gcatacactc ccctacccac ccacctcgcc taccctcggg gcgagaggct | 840 |
| caccaaggca gggcgcgccc ccccatgaa tcatcccaag gcctctgagc cgcgggggct | 900 |
| ccgggcaact atcccctcc tctcctggcc tcaggcaccc cagtccaggg gtctgcagag | 960 |
| aagcccgaag cccggacaaa cgcgccgac gtcaacaacc tctcatccct ggcagcagca | 1020 |
| aaggccaata tatttccatt tcttatttca gtttgccacc aaaacaaagc tgcgcgcggc | 1080 |
| tgagggcagg aaggcgctga gaccgagaag aagggacgtc ccggagaaag tgcgcccagc | 1140 |
| tgatcttaga aaccagagtc ctccgggact tcgccgagat tttctgtagg gcgttttaat | 1200 |
| ctgttttcct actgcgtgcc ggcgtcgcag cgcgtgcggc tcagggcttg gtgactccgg | 1260 |
| cttagcccgg cggtcgcggc gaggttcctg gcgcagccgc ttggaacttc gcattagaat | 1320 |
| cgggaccgcg caaatgccct ggctgaagtg tcaccctatt caagaaacac tgctgtcagg | 1380 |
| aacaaaatgg ggtccccggt gctccgaagt atcttctgaa attttcttaa aacaacttac | 1440 |
| aaaaaatgtt tttgctttaa cgttttacaa cgtttaagga aacatgtaaa tggtctgttt | 1500 |
| ctttatcgag atggtcgtcc taactaacag tgtacacata cataacaatt cttccaactt | 1560 |
| tcctcctcag agctaagcac ttcactatat gtaaattata ataaagaaaa gattgtgcaa | 1620 |
| gatcatgcaa gtcgattgac ttaaaatatt gagttttaat ccaggccctc tgttttccta | 1680 |
| tttaacaact tttgtgtttg gaccagactg gtgaagcagg ctatggaaat taacaaagta | 1740 |
| aaaaattaaa agcatcttcc ttcgccatcc ctccctccaa aattaaacaa cagtcgcccc | 1800 |
| ttcctgagca ggcttcagtc ccaggctcga gttttcctgc gatcacccca cagtcaccca | 1860 |
| cagcagctgt tgctgcttct gtcgggtttt cgtttctgcc ttctttgggt cgtctcttgt | 1920 |
| atacaaaaca caccccagtt ctctaactaa attcaaatac gaccccggca gaatttacac | 1980 |
| atttcgtggt gcatggattg tgtcggtgca ggggaaataa ataccctctg gtatttaacc | 2040 |
| actgagtcta attcgaaaaa tcgggactgg gcccctaggc ggcaccccag gggctccaac | 2100 |
| ctggcccgcg cctccccaga ccttggcgct gagagcgctg cttttgcggg tgggtggacg | 2160 |
| gagaggtaac aatctgcttt caacaaaaac ctgtcgccac cgaatcgaaa gcgaaaggga | 2220 |
| agggagaag | 2229 |

<210> SEQ ID NO 3
<211> LENGTH: 7833
<212> TYPE: DNA
<213> ORGANISM: Homo Sapiens

<400> SEQUENCE: 3

| | |
|---|---|
| gtctttggtg agatatgtgt tttacaagtt ttaatggaga aaaatgtaag tattttacct | 60 |
| cctgaaactt ggctatttga gtaatgagaa aatagtcact ttccccagga cagtggttct | 120 |
| caatcatggc tatgtgtttc tccaggaaaa ctttaaaaat atatatatac caatgcttct | 180 |
| gtgtcacttc tagggattcc aagtctttga atacgaactc tgcatcagta ttctttaatt | 240 |
| atccaggtga ttgtgatgtg aaatcatgac tgagccccac tgctctaaga tgaaataaac | 300 |
| tttcctcagc actgaaatca caaacttaaa ctaccaaaat taattaaggg catgggaatc | 360 |
| aataaggcat agggaagctt ttacattata aaattatttc tttaaatcac agctcattgt | 420 |
| ttatatgtta tttgccattg tagaaaaggg tgaaaaaata gcaaatttaa ttactctcag | 480 |
| tttgaaaaat tatccagaaa tgaagatgac gactctgaaa cattgtcaat atcatttgac | 540 |
| ctataaaataa tgttctaata catttactac acactgatag atacttttc atatgaatat | 600 |
| tatacattaa aactaaggca ataatgcatt tagaacattc tatctatatc tatgtatctt | 660 |

```
aagtaggcta gaaattaaga tatgagttat taagtatgag atgttaaggt gtggggttag    720
aaattatact gtacttcatt atcaataatc aacatatact tcaatatcac atacatttaa    780
ctttaatttg tacatcttta actatttta attatgtgta taaatataag tacacacatc    840
tttatgtatt tatttattca tacctccatt cacttattta tatagggggat ccccccaaat   900
```

```
aagtaggcta gaaattaaga tatgagttat taagtatgag atgttaaggt gtggggttag    720
aaattatact gtacttcatt atcaataatc aacatatact tcaatatcac atacatttaa    780
ctttaatttg tacatcttta actatttta  attatgtgta taaatataag tacacacatc    840
tttatgtatt tatttattca tacctccatt cacttattta tatagggggat ccccccaaat   900
ccactaccat taaaccatac atttttattt taatctttag aacaagccca ggaggcaggt    960
attgttatta ctcacatttt acaaatgagg aaattgtcta cagtcacaaa gttactgtgt   1020
cagacatatt agaagcttaa tacatatttg gtgaacatat gcataaaaac agagagacag   1080
acatgtacaa cagctcatct ttacactgag taaaagcttt taacctgtct cagaaacctc   1140
tctgtgaaaa ctgagcaaaa atcgaggtat cctttcattt gtcatatagg tataggtggt   1200
accttacttc tccaacaagg atgaatattg aaatgtggat cccaaggccc aactccagat   1260
tttctgaatc cctgatagtg ggacttggaa tttgtctatt gtttcaaagt ttctcaagga   1320
attcatatga tcaaccaggt tcagaaatca ctggatctta ttgccgaagt ttgagaatta   1380
aagtttgggc cttactgcgg ctccacagaa agggcaaatg aagtatcatg gacagaactg   1440
atacgttccc agttagtttc ccctctcaga agctaacagg cagcaataca gcagaaatta   1500
gtgacttatg tcttgtgctc tgaagtcagg cagaatttca cagagtccca gcagtgtcac   1560
tgacgagatt tgtttcttgg ggcaagttgc ctgatgcttt caaagccata ttccttttat   1620
ataaaatgag ataatattct ttgtctcata ggggtgtttt aaagattaaa taaaaataac   1680
atgttctatc ctacatggca caatgcctga cacctaagaa gcaaggata  catcttacct   1740
ttattgaagc aatcagaaag tatgaaatca tgaaggagat aagagttctg attggcagtg   1800
tatcttattt tcccaggttc atttatttat cttaaactat tcttgttgga gaataactcc   1860
caagccccct acttaagctg tgagtaatct cacactttat aatgatgttc tttccatgag   1920
aaaaaaaaat gttcttaagt tttctggaga aaatatatct gcactatttc tactgaaaaa   1980
tctaacaact ggactctgct cctctgcatc aattctagag tgtatatgcc acaaataaag   2040
tgttctagct caagaagatt gaaagtaaat atggtatagt attttaaaat aagaattttg   2100
caaatacatg gtatgattgt gtcatattac tagcaatcat atgatacgca atgcaaagta   2160
cagttcatag acttaaattt aattctaata agtaaactga ttttgccttg ctggggaaaa   2220
gttaaagcac taatccaatt gctaatgcag tcttgtctac ttctttggta cctagtgaca   2280
agtctaaata atgtatatat ttttatttac atattcagta atacaattct ctgctcaatg   2340
agtgatgttc ttctgccact tggtggtgct tgccagtttc agaatttgtt tcttggtggc   2400
actataacac taagtacaga gtaagtgcaa caaaattgca gcattcccat tgaaaaggct   2460
ttgcttcaaa ctgtttaata atttaaagga cctctgtgga agcaaccgca tttgttaacc   2520
agttacaacc agtaattaac tcctttggag ttttaactta cttttggcaa aacgtcttag   2580
gaagagcata tattattaga aagtatgcca aaaattact  tagcagaaaa ttcaaaaaca   2640
gttttcctct gctaagaggt tctctaaaat tctacttaca tagccaaact ctgaaatcct   2700
agcaggtcct gtttcattat cataattact gcataaacac ttttaaggac tttgccttta   2760
gtttcaagca tgacttattt tcataagcct gattagttac caccagcc   ttgctatgga   2820
aaatgacatg ttctcattct ctgctgtaga gttgttaaat cttgatctat atttatgttg   2880
ccttctctgc tgaaagcctg tagcgaaaga aatttctaat tccttgtttt gcaatattag   2940
ttggcagctc tatctaatgg gtattctgtt tccttaaaga atttagctgc tctgtctaga   3000
agccgatttt ctgatgcctc caacgtctgg tctaattgat ctgtttaat  ggagtcttcg   3060
```

```
tcggtgagga gcgagatgcc accgactaga atgctgggat ctgctgctta attgccagga    3120
gtgagagaca ctgagattca gaaatctttg gaggtgggag gggagaggga cagtctcgga    3180
cggaggcgga gatgtaagat aaagggatgg atttcacaca ggaaaaaaaa aaagatttcg    3240
ttgaggcact gaggtgctgc acgatcacat ctctcaaagg agaagttaaa aagcaaggaa    3300
gtgggaggag gttggaggtt aaagtactta aaaggattac tcgggtacaa tttgtttttc    3360
tgctggtgtc tgcaaaggat agatagtccc gttttcaaag tatatgaatg cctcttttaa    3420
gtgattggga atggacacta attgcctgtt aaatgttatc aaatgctctc ctaaattcag    3480
gggacacaga aagaggggca caaaggagaa atttaaatag aaaaagggag gatccggagg    3540
cttttgaaag cgggggaga agaaggagga gggataacag agaggaatag agaaggagag    3600
cggagagaag ataaacaaaa acaaaaacag gaatcactga ataatcacac accaaaaaga    3660
aagctcttcc ctatggggca tccaaaacac tgagactgca atagtgaccc cggtcatgga    3720
agaaagatgt tcctctccac ccttgtcccc gaaagctctt ggtcccgtta ctggcgacta    3780
aaattccatt aggctaaaga gtgtgtctaa ctgcctgaag aatgcagcag acggaaggcg    3840
ggtcccgcta tgccgtttgc ccttcccgct ggagagaatg aaagaaacgc gcagagccag    3900
agactcctgc cgagttagac cttctctcgt cgccccaggt caccggccat ccggcaaaga    3960
cccgagtaag gaacgcaggg tcactgcctg ggccaacaaa tggagcccgc tctcccttc     4020
ccggacgccg ctgcccggcc gatgctcccg gcaacccacc cgcggcgtat gcagaggagc    4080
ctttctcttt ctctcagacc acttgtcccg accaatctga ccttccaaac acatctgacc    4140
gcacctccca ggtggacaca ctaataggct acgggctgga gaggagcggg tgatgaggag    4200
agggattcaa acctgcgaac gcttgggctg ggtcggagct gcgggggggcc tgggaggaga    4260
gaggggagaa gagagaagga aggagagcgc ctgccgggat ggctgagctg cctcggcgag    4320
cagccttggg gttgcacgct cttgtgggag atgctgctgt tgcttccagg tcggcaagag    4380
cggttctaac accatcgcct ctcaccctct ttcctgtaaa tccctagaga aacgtccctg    4440
gcctctccgc cgcgacattc ccagcctgca tccccctaca gcctaggcgg cgcgctcccg    4500
cacgctggag cgccggtcgc cagcaggacg ccctctcccg cgccgactcg cccctctctg    4560
ccctgctgct gctgctcctc tgacacctcc gcccccacca tctccagctc ggagagacgc    4620
cacccagccg cggcccgcac tcgcggcccg gggtcacgcg cggaagaggg gcgctagtcc    4680
ggaccccgcc ttcggtaggg ggcgtcctgg agcggagagt gaggcgaatg gtatatgagt    4740
gtgcgggtag cccaccctga agcccgagct tctcatttga gccatgcccc gcctagcccc    4800
actcgggcca gcgcctggcg agcgagccca tctgtggctt ccgcggccgc ctcctccttg    4860
catccttgca cctactcgtc gacccctccc tcccgggacc tgcatcctgc tccaccaatc    4920
agagcccgac tgcctcttcc cacgtgaccc cgggcgggct gaggacctgc tgcttcccaa    4980
acgccagagg gatgcgggcg gcagagctcg agaggcggct gccgggctgc ggggcgcctt    5040
gactctccct ccaccctgcc tcctcgggct ccactcgtct gccctggac tcccgtctcc    5100
tcctgtcctc cggcttccca gagctccctc cttatggcag cagcttcccg cgtctccggc    5160
gcagcttctc agcggacgac cctctcgctc cggggctgag cccagtccct ggatgttgct    5220
gaaactctcg agatcatgcg cgggtttggc tgctgcttcc ccgccgggtg ccactgccac    5280
cgccgccgcc tctgctgccg ccgtccgcgg gatgctcagt agcccgctgc ccggcccccg    5340
cgatcctgtg ttcctcggaa gccgtttgct gctgcagagt tgcacgaact agtcatggtg    5400
ctgtgggagt ccccgcggca gtgcagcagc tggacacttt gcgagggctt ttgctggctg    5460
```

```
ctgctgctgc ccgtcatgct actcatcgta gcccgcccgg tgaagctcgc tgctttccct      5520
acctccttaa gtgactgcca aacgcccacc ggctggaatt gctctggtaa gtccagaacc      5580
cccgtccccg acccctttaac tccgcagaag aacacgcgta tccagcacag accagcctac     5640
cctagcgcgc ctcctcagcc cctcacctcc tactgcccta gaccctaat accacccacc       5700
tctatccaga gaaacaaggg gaactgttgc aggcccgggg gtgaggggtg gttctgggat      5760
gggcagaaag tgcaggtgta gcaggaaacc tttgcatgct gcgcttaca ttggagctgc       5820
gaggattttg agaaatatta acgggatgg ttttctgggt tcactgtttt gaaagagcac       5880
caatcctagg ggaaacactg aaacagaagc tttgtcatca ttaaagaaaa aagtcttact      5940
aggatgagga agaaataact ttatgagaaa gaatgagcga gaaagcaata aatcaaatgg      6000
tgactgcagg ggaatcgctg attcctggca aaggtgccat gaggtcgcac tggtctcccg      6060
ttgaagacca ggtcacacag attctagagg agctgggttt caatagaatt tctctctctc     6120
tctctctctc tctctctctc tctctctctc tctctatc tatctatctc tctctctctc       6180
tcattccctt ctcctaggg cggcaaaaga cattggtttt gcagtccaga tatgcccctc      6240
tctttgcttc cctaagcttc aaggtagtac aggggagttg agaaaaagaa cactttgcgg     6300
gtctcccagg ccggagtggg catgactgag gctggtcagg ctccatgtag gcgagccgag     6360
ggcggaaccg acttcagtgg gcgctgactc ctccatttct ggacaggctt ctgtggagtg    6420
ggtcaggcac tcttcttgct cgctcgggtt ccttcagatt ctgacggcga acgcttggca    6480
ggcttcgctc tgctgaagct tcctaattaa atagggccag aggatgggag ttgctgcact    6540
cctagctggc atagcattcg gtttgacagc ctgtagtata gggtgtatgt aattttcat     6600
cttctgtgaa tataattttg ctgtagttaa atctggctct gaataaagtg tctttcaaag    6660
atgtatataa gctgaagtgt atgtaacttt agagaggagg gaatgaccaa ctgtaactca    6720
gggtgaaagc ctgtatagtt cctagttatt actgatgtaa atgccaaaag gaaaattatt    6780
atgcatcatt ctaatttatc ctttacaaag acaagttgag atatgcaacc ctattagatt    6840
tgggtcaata gattgttctc ttttttggca gtttctaaat ttggcatttt aataaaactc    6900
aacatgtttc tataacttct tgattcatgc gtacatgtgt gttgttttg aaagaataag     6960
tttcactttg ctattgccta atcactttt agatgcttta ttatggtaat aattatgagc    7020
ctgcaaaaac aattttttgga aatgttgatg gctttgtagt ccaacacaga ctggtttgct    7080
tcattcctag cccttgcatt gttttaggaa ataactaact taaatgtgaa gttgacattt    7140
gcaatcaaga aattacatat ttaccagata ttttaaaggg gactgcataa actaaagaga    7200
ataaactggt tttgcagata ggttgtcaag aacttggcac cccgcttcca cccctgttaa    7260
cttagaggtg atcaatcttc atttgagcca aacagaccat cacagaaaac actgtgcctg    7320
tttatcttta ttattgaggc tttgtttcct ctttgtctgg atacatttca ataagggt      7380
tgtttcagtc gttgaagcaa aagaacaatt aaagatgggg aaatggtaaa agggtattca    7440
gagatcatca ctagctcttt tccaaaatgt ggagttttgt ggtcataaat attgtccacc    7500
taatgagcaa aaaataaaaa taaaaaaaaa acaggaagca aatgttaagc tttcattcac    7560
cactgtcagt attaacgcaa gctttaaaaa atagcactat cagaaaagga tactaaagga    7620
gaattgacta gaaaagaatt gtggaaaatg gaaacgaata ttgatcactt aactagattt    7680
tgaggttatc agtagacagt gaccttgcag tacagctata gttgttggat ttaaaattta    7740
ggacaagtat tttaaagctt caagtagtg ctttttttg ttaaaaatct gtaagatgtt      7800
ttaatgactg gagtgttctc tttgaatttg agg                                  7833
```

```
<210> SEQ ID NO 4
<211> LENGTH: 5666
<212> TYPE: DNA
<213> ORGANISM: Homo Sapiens

<400> SEQUENCE: 4
aaaattagaa cttttacctc cttgcgcttg ttatactctt tagtgctgtt taacttttct        60
ttgtaagtga gggtggtgga gggtgcccat aatcttttca gggagtaagt tcttcttggt       120 cttctttct ttctttcttt ctttttttct tgagaccaag tttcgctctt gtctcccagg       180
ctggagtgca atggcgcgat ctcggctcac tgcaacctcc gccttctcct gggttcaagc       240
gattctccta catcagcctc cgagtagctg ggattacagg catgcgccac caagcccgc        300 taattttgta ttttttagta gagacagggt ttcgccatgt tggtcaggct tgtctcgaac       360
tcctggcctc aggtgatccg cctgtctcgg cctcccagaa tgctgggatt atagacgtga       420
gccaccgcat ccggactttc cttttatgta atagtgataa ttctatccaa agcattttt        480 ttttttttg agtcggagtc tcattctgtc acccaggctg gagggtggtg gcgcgatctc       540
ggcttactgc aacctctgcc tcccgggttc aagcgattct cctgcctcag cctcctgagt       600
agctggaatt acacacgtgc gccaccatgg ccagctaatt tttgtatttt tagtagagac       660
ggggtgtcac catttttggcc aagctggcct cgaactcctg acctcaggtg atctgcccgc       720
ctcggcttcc caaagtgctg ggattacagg tgtgagccac cgcgtcctgc tccaaagcat       780
tttctttcta tgcctcaaaa caagattgca agccagtcct caaagcggat aattcaagag       840
ctaacaggta ttagcttagg atgtgtggca ctgttcttaa ggcttatatg tattaataca       900
tcatttaaac tcacaacaac ccctataaag caggggcac tcatattccc ttcccccttt       960
ataattacga aaatgcaag gtattttcag taggaaagag aaatgtgaga agtgtgaagg      1020
agacaggaca gtatttgaag ctggtctttg gatcactgtg caactctgct tctagaacac      1080
tgagcacttt ttctggtcta ggaattatga ctttgagaat ggagtccgtc cttccaatga      1140
ctccctcccc attttcctat ctgcctacag gcagaattct ccccgtccg tattaaataa       1200 acctcatctt ttcagagtct gctcttatac caggcaatgt acacgtctga gaaacccttg      1260
ccccagacag ccgttttaca cgcaggaggg gaaggggagg ggaaggagag agcagtccga      1320
ctctccaaaa ggaatccttt gaactagggt ttctgactta gtgaaccccg cgctcctgaa      1380
aatcaagggt tgaggggta gggggacact ttctagtcgt acaggtgatt tcgattctcg       1440
gtggggctct cacaactagg aaagaatagt tttgcttttt cttatgatta aaagaagaag      1500
ccatactttc cctatgacac caaacacccc gattcaattt ggcagttagg aaggttgtat      1560
cgcggaggaa ggaaacgggg cggggcgga tttcttttta acagagtgaa cgcactcaaa       1620
cacgcctttg ctggcaggcg ggggagcgcg gctgggagca gggaggccgg agggcggtgt      1680 gggggcagg tggggaggag cccagtcctc cttccttgcc aacgctggct ctggcgaggg       1740
ctgcttccgg ctggtgcccc cggggagac ccaacctggg gcgacttcag gggtgccaca       1800
ttcgctaagt gctcggagtt aatagcacct cctccgagca ctcgctcacg gcgtcccctt      1860
gcctggaaag ataccgcggt ccctccagag gatttgaggg acagggtcgg aggggggctct      1920 tccgccagca ccggaggaag aaagaggagg ggctggctgg tcaccagagg gtggggcgga      1980
ccgcgtgcgc tcggcggctg cggagagggg gagagcagga agcgggcggc ggggagcagc      2040
atggagccgc cggcggggag cagcatggag ccttcggctg actggctggc cacggccgcg      2100
gcccggggtc gggtagagga ggtgcgggcg ctgctggagg cggggcgct gcccaacgca      2160 ccgaatagtt acggtcggag gccgatccag gtgggtagag ggtctgcagc gggagcaggg      2220
```

```
gatggcgggc gactctggag gacgaagttt gcagggggaat tggaatcagg tagcgcttcg    2280
attctccgga aaaaggggag gcttcctggg gagttttcag aaggggtttg taatcacaga    2340
cctcctcctg gcgacgccct gggggcttgg gaagccaagg aagaggaatg aggagccacg    2400
cgcgtacaga tctctcgaat gctgagaaga tctgaagggg ggaacatatt tgtattagat    2460
ggaagtatgc tctttatcag atacaaaatt tacgaacgtt tgggataaaa agggagtctt    2520
aaagaaatgt aagatgtgct gggactactt agcctccaat tcacagatac ctggatggag    2580
cttatctttc ttactaggag ggattatcag tggaaatctg tggtgtatgt tggaataaat    2640
atcgaatata aattttgatc gaaattattc agaagcggcc gggcgcggtg cctcacgcct    2700
tgtaatccct tcactttggg agatcaaggc ggggggaatc acctgaggtc gggagttcga    2760
gaccagcctg gccaacaggt gaaacctcgc ctctactaaa aatacaaaaa gtagccgggg    2820
gtggtggcag gcgcctgtaa tcccagctac tcgggaggtt gaggcaggag aatcgcttga    2880
acccggggag ctgaggttgt agtgaacagc gagatggagc cacttcactc cagcctgggt    2940
gacagagtga gactttgtcg aaagaaagaa agagagaaag agagagagaa aaattattca    3000
gaagcaacta catattgtgt ttattttttaa ctgagtaggg caaataaata tatgtttgct    3060
gtaggaactt aggaaataat gagccacatt catgtgatca ttccagaggt aatatgtagt    3120
taccattttg ggaatatctg ctaacatttt tgctctttta ctatctttag cttacttgat    3180
atagtttatt tgtgataaga gttttcaatt cctcattttt gaacagaggt gtttctcctc    3240
tccctactcc tgttttgtga gggagttagg ggaggattta aaagtaatta atacatgggt    3300
aacttagcat ctctaaaatt ttgccaacag cttgaacccg ggagtttggc tttgtagtcc    3360
tacaatatct tagaagagac cttatttgtt taaaaacaaa aaggaaaaag aaaagtggat    3420
agttttgaca attttttaatg gagaagggag aagaacatgt agaaagggg aaatgatgtt    3480
ggcttagaat cctaactaca ttggtgttta atataggaac atttatttat ataacatttt    3540
aaagtactaa attcatatta gtatattatc aaatggatat attatcaaat gggtttaagc    3600
atcctacaca ttttaattca attgattcat tttcttttttg ctttggattt ctatcatgat    3660
ttaaatattt acatatgggt tacttttttag atttttcata ctatgaaata taagaaaaac    3720
ctttaaggct agttttatga ccaagacgaa ggacttcatt gaatacacaa aacaataaat    3780
atactgcaac attttgtctt tcttttttgta gctgcaattt ggtttgctta cttttctct    3840
ttgtctcttt gaaaactgag tcagtttcac tttctcagga caggatttaa taaccataat    3900
ataatttagt ataattcctt gatttaggca aattatgcaa tttgtgttta gtatgaaatg    3960
tacctaaaaa taagtaactc ctcttttaaca ccaccatcct caaactaata taacaaataa    4020
cagttatcct aaaataaatt gtctacttcc accatgcagc actcaaattt taaggttgct    4080
atgactgcag acagtatttt aaaattcctc tctggaaatg gctttgtttc caagatgatt    4140
taggaaccaa agaggtgacc atctcttgtt taatgaactc tcaaatcata aacctgggaa    4200
gtgttttagt ttcctactgc tgctgttaca aattatcaca aatgtgttag ctaaaacaaa    4260
cacaaaatta ttattttaca gttctagaga tcagaagtca aaaatgggtc cacaaggttt    4320
cattcctttt ggaaactcta aggggcaatc tgtttccttg tcttttccag cttcagtga    4380
ccatcaaatt ccttggctca tggtctctgt atttttctctg tggcctgtgc ttccattctt    4440
gtatcttctc tctgactgtg accctctaat aaaaacactt ggggttatgt tgggcccacc    4500
ctgaaaattc tggataatct ccctcaagac cattaattaa atcacatctg caaagcctct    4560
tttgccacat aagttaatgt attaaaagtt tttgaggatt aggacataga cattgggggt    4620
```

-continued

| | |
|---|---|
| gggggggcat tattcagcct accacaggaa ggaattttag ggttaattaa actagccttc | 4680 |
| ttattttata cttgaagaaa ttgaagtttt ggaattggag agcattatgc taaatgaaat | 4740 |
| aagccaaaca cagaaagaca aatatcacat gttctcactt atctgtgaaa tataaaacaa | 4800 |
| ttacattctt agcagtaaag agtagaatgg tggttactag agctgggggg tgggaggaat | 4860 |
| ggggagatgg taatcaagat ataaagcctc agttaagatg ggaggaataa gtttgattgt | 4920 |
| ttttttgag atgtgtttca tagcatgatg aatatagcta aatagtaaat cccaaatgct | 4980 |
| ctcatttgac aaaaatgtca aatatttgag atgatggata ggttacttag cttgacttaa | 5040 |
| taattcccca ttgtgttcaa agatcataac ttcatattgt accacataaa tatatacaac | 5100 |
| tgtactatcc caatatataa ttttaaaact aatataatga aaagaaatt gaagttcaac | 5160 |
| attcccagaa gctaagtgta acttaaaagt tttgtgagaa tttgttttaa caaacaaaca | 5220 |
| agttttctct ttttaacaat taccacattc tgcgcttgga tatacagcag tgaacaaaaa | 5280 |
| aaaaaaaaaa aaaaaaaatc tccaggccta acataatttc aggaagaaat ttcagtagtt | 5340 |
| gtatctcagg ggaaatacag gaagttagcc tggagtaaaa gtcagtctgt ccctgcccct | 5400 |
| ttgctatttt gcccgtgcct cacagtgctc tctgcctgtg acgacagctc cgcagaagtt | 5460 |
| cggaggatat aatggaattc attgtgtact gaagaatgga tagagaactc aagaaggaaa | 5520 |
| ttggaaactg gaagcaaatg tagggggtaat tagacacctg gggcttgtgt ggggtctgc | 5580 |
| ttggcggtga gggggctcta cacaagcttc ctttccgtca tgccggcccc caccctggct | 5640 |
| ctgaccattc tgttctctct ggcagg | 5666 |

```
<210> SEQ ID NO 5
<211> LENGTH: 2470
<212> TYPE: DNA
<213> ORGANISM: Artificial Sequence
<220> FEATURE:
<223> OTHER INFORMATION: chemically treated genomic DNA (Homo sapiens)

<400> SEQUENCE: 5
```

| | |
|---|---|
| aaagatgatt aaaagtttaa ttgtttattt gaagagttga tttttttatt tttgtaataa | 60 |
| agggtatttt tagtagtttt tgtttatttt gtttattcgg ttttttttgt ggttgtgtaa | 120 |
| ggttataatt tttgtgtttt agtaaatttg tgtatgttta tttttttttt tgttattatt | 180 |
| ttttttttta ttttgtttta ttttttgat gtaaaattat ttgttaattt tatttgaaat | 240 |
| gagaaatttt aaggtttata ttatttaaat tttgttagat ttttattttt gttatatggt | 300 |
| ttataatgtg ttgggtattt ttagatttgt ttattaaaaa gatgtaaaat aaaataatga | 360 |
| ttattttgt ggatttttt tttattttg agatgttttt tttggttgta ttattttttt | 420 |
| atttttgtt tattgattag aggagggggtt taattatgg gtgaattta tattttattg | 480 |
| aagaggttat gttatatgta tatttttata atataattta tatttatata gtatttttat | 540 |
| ttttagtata ttttttttta ttaattttaa taatattatt gtaagttatg ttgaagtaga | 600 |
| ttgtaagtgt ttatttataa attgtgaaat gaattaaaat gaaagggtaa agattaaatt | 660 |
| atgattaggt ttgaaattaa tataagat ttaatttttt ttaattaaag attttgtag | 720 |
| gtgattttg tttgtaggat tttttttttt tttagatgt tattggattg tattaggttt | 780 |
| attgtagatt ttagtcgttg tagaattaat tagatttaag atgagttttt tgatttttt | 840 |
| tggtagagtt ttttaattgt tgaatttaa tattgtcgtg attagttagt gttataattt | 900 |
| gtttgtttta ttttgtgtaa tggatttat attatagagg tatttttta atgttaagat | 960 |
| gtttaagtat tgtttaagtg taaattattt aatattttt agttattaag taattaagat | 1020 |

| | | | | |
|---|---|---|---|---|
| aggtaggatt | ttatttgttt | taaaatgatt | tgatttaaat | taaaaagaga atgtggattt | 1080 |
| tttgaatttt | atttggttaa | ttttaatata | attttttagta | ttttataatt tttttttaaag | 1140 |
| ttttttatt | tggttatttt | ttgtatttt | tttgttttt | ttttttttt ttagttataa | 1200 |
| taattgttag | attttgtttt | atttttttt | gatagtttt | attttaagg ttatttattt | 1260 |
| tttttaggta | ttttttggtt | ttagtttgag | tatagtagat | tttaagatta tatatgttat | 1320 |
| agtataggtt | attatagtta | atttttttgaa | taaatgtgat | tgaattttat gttagtaatt | 1380 |
| tttatttatt | atttttttat | taaaaaggtt | taaagttttt | atttaatgtt ttttttatg | 1440 |
| tttatttgt | taaatgattg | tttttaatg | atattttaga | attttagaat tattttatta | 1500 |
| tggaggatgt | gtaagattag | ttttttatta | aataaaaagt | gtgaaatgga atatgtaatt | 1560 |
| ttattaattt | attttggttt | taaaattttg | tgattattag | ataaaattta gaataaaaat | 1620 |
| agtattatta | atataaataa | attttttatta | taattatatt | ttttaagttt tgtttgtaag | 1680 |
| aatgggtaaa | atattttaa | aatttgtaag | aaattattat | ttgatagaaa gtttaattta | 1740 |
| tttgtgagaa | ggtaaatgta | tttagatata | attaaagttt | tttttttat tttaatttta | 1800 |
| tttattttga | attaagattt | tattgttta | tttttttaga | tgttgttatt tgaataaat | 1860 |
| tgttttgaga | ttaaaaatta | gtatattaat | ataatttttt | ttaaacgttt taagagtttt | 1920 |
| gttttttta | ttttttttt | taaaaataag | tagttattaa | attttttagt agtgaatttt | 1980 |
| aaaattttt | ttaatttat | aggtttaagg | gtagttaagg | atggttgtag ttttatatga | 2040 |
| ttagttgtta | aagtaagttg | aggtattgaa | gatggagaat | ttaaattttc gataagagtt | 2100 |
| agaagataat | tttaattatt | ttataaaatt | ggaaattgag | gtatttaata tgaaggtatt | 2160 |
| aagattgtga | tttttaattg | tagttattt | attttttattt | agtatttttt tttgtaaatt | 2220 |
| tgaggtaaga | tatttattt | aaaagtgtat | tttaaattaa | gtaataatat gtaaattttt | 2280 |
| ttttgtaaaa | gttagtattt | atattttaa | ataagatata | ttgaatttat ttagtgaatt | 2340 |
| atataaagaa | aataagtgta | aaatttttaat | ggttagttag | ttttagtttt tttttaagat | 2400 |
| taaagagaag | agattaaata | tagtattatt | gtattgaggt | aaggttttt gtgtagttta | 2460 |
| tagaaattag | | | | | 2470 |

<210> SEQ ID NO 6
<211> LENGTH: 2470
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6

| | | | | |
|---|---|---|---|---|
| ttagttttta | tgaattatat | agaaaatttt | gttttagtat | agtgatgtta tatttggttt | 60 |
| tttttttta | atttaaaaa | gaattaagaa | ttaattagtt | attggagttt tatatttatt | 120 |
| tttttatat | gatttattga | atgaatttaa | tatattttat | ttaaaatat aaatgttaat | 180 |
| ttttgtaaga | aagagtttat | atattattgt | ttaatttaaa | atatatttt aagtaaagtg | 240 |
| ttttatttta | agtttataag | agggaatatt | gaataaaaat | ggataaatta taattaaaag | 300 |
| ttatagtttt | gatatttta | tattagatgt | tttagtttt | agttttgtaa gatgattgga | 360 |
| attatttttt | agttttgtc | gaagatttga | gtttttatt | tttagtgttt taatttgttt | 420 |
| taataattga | ttatatgaag | ttgtagttat | ttttggttat | ttttggatt ataaggttaa | 480 |
| aaaggatttt | gaaattatt | attaaaaaat | ttagtggttg | tttgttttta aagaaagggg | 540 |
| taaaggaaat | aaaatttta | agacgtttaa | gaagaattgt | gttaatatgt tagttttgg | 600 |

```
ttttaaaata atattgttta agtagtagta tttaagagga tgaaatagtg gagttttagt    660
ttaagataaa tgaaattaaa atagaagaga gaattttagt tgtgtttgaa tatatttgtt    720
tttttataga tggattaaat tttttattaa gtaataattt tttaaggtt ttaaagatat     780 tttatttatt tttataggta aaatttagga aatataatta tgataaaaat ttatttatat    840
tagtaatatt attttatttt tgaatttat ttgatagtta tagaatttta gagttagaat    900
ggattaatga gattatatat tttatttat attttttatt tgataaaagg ttaatttat    960 atatttttta tggtgaaata gttttgaagt tttaagatgt tattaaaagg taattattta    1020
ataaaatgga tatgaaggag agtattaaat gaagatttta agttttttg ataggaagat    1080 ggtaaataag aattattaat ataaagttta attatattta tttaaaaggt tgattataat    1140
agtttatgtt atggtatatg tggttttggg atttgttgtg tttaaattga ggttaaaaga    1200
tatttaaaga gaatggatga ttttaggagt agagattgtt aaagagaaat gaagtagagt    1260
ttggtagtta ttatgattgg gaaagaagag gagagataaa gaagatataa aagatagtta    1320
ggtaagagga ttttaggaag aattatagaa tgttaggagt tatattaaga ttaattaagt    1380
aagatttagg agatttatat tttttttta gttaggttaa aattattttg gaataaataa    1440
aattttgttt attttaatta tttaatagtt aaaaagtatt aagtagttg tatttaagta    1500 atatttaaat attttgatat taaaaaaatg ttttgtaat atgaaattta ttatataaaa    1560
taaggtagat aggttgtaat attggttagt tacgataata ttggagttta gtaattggaa    1620
gattttatta aaggaaatta ggggattat tttagattta gttagtttta taacggttag    1680
aatttatagt aaatttggta taattaatg atatttgagg aggaaggga gttttgtagg    1740 tagggattat ttataaaagt ttttggttga aaaaaattga gttttgtgtg ttaattttag    1800
gtttggttat gattaatttt ttgtttttt attttaattt attttataat ttgtaaatga    1860
atatttataa tttgttttaa tataattat agtgatatta ttaggattaa taaaaaagg    1920 tatgttaaaa ataaaagtat tatgtaaatg taagttatat tatgaaaata tatatgtaat    1980 ataattttt tagtaagata tagggtttat ttatagttaa gatttttttt ttgattaatg    2040 ggtaagggt gaagaagtaa tgtagttaaa ggagatattt taaaaataaa ggaaaaattt    2100
ataggagtga ttattattt gttttatatt tttttaataa gtaggtttga aaatatttag    2160
tatattataa attatatgat agaggtaggg atttgataga atttgaataa tgtgaatttt    2220 aaaattttt attttaaata aaattaatag gtaatttat attaaaataa taaaataaaa    2280
taagagaaaa ggtagtaata gagaaaaaaa tgggtatgta taagtttatt gagatataga    2340
agttataatt ttatataatt ataaaagag tcggatgggt aagatgagta gagattgtta    2400
aaagtatttt ttattatagg aataaaaaaa ttaattttt agatgaataa ttaaattttt    2460
aattattttt                                                           2470

<210> SEQ ID NO 7
<211> LENGTH: 2229
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7
ttttttttcg gcgttggttg gtgcgggttg gggttaggtg gagaagtcgt tttttgttaa     60
ggtgatagaa cgtgttgggg gtgggggtcg gggtagggt cggtgtaatt aggggggtcgt    120 tgttttttt tggatatagt ggaagttttt ttcgtattat taaatttttg ttatttttt     180
```

```
tgagggattt gttttaggt agtacgtaag ttgttgtttc gggtttattt cgtatttttt      240
tattgggtga ggaaggagta ttttgaatgg agatgggggt gttttcggtt tatatatttg      300
tagagaagag gtgtgtcggg ttgtattttt ggaggtcgcg gtaattgata ttagagaaga      360
tttcggttgt agttgggaag gtttattggt tggaaagagg tgtttttttt ttttagtaaa      420
gggttttgtt tggaagggtt gttttttatt tgtttagtgg tattatagga cggtcggttt      480
ttattcgaat ttttcggac ggtattatta tatagtcggg ttttcgtagt gttggttttt      540
taattcgatg attgttattt cggtgaggat ttgtgttgat ggtcggagaa ttttgcgttg      600
cgggcgtata tggttaggtg gcgtttggta ggcgacgttc gggtgtagga cggcgttttt      660
atcgttttat tttaaatcgt tgtttgggtt taggttttc ggttttttga ataggggttt      720 gggggggttaa ggacgttgag gtttcggggg taggaagttt tttttggtta agcgtttttt      780
ttttttttcg gtatatattt tttattttat ttatttcgtt tattttcggg gcgagaggtt      840
tattaaggta gggcgcgttt tttttatgaa ttatttttaag gtttttgagt cgcggggggtt    900 tcgggtaatt atttttttttt tttttttggtt ttaggtattt tagtttaggg gtttgtagag    960
aagttcgaag ttcggataaa cgcgtcggac gttaataatt tttatttttt ggtagtagta     1020
aaggttaata tatttttatt ttttattttta gtttgttatt aaaataaagt tgcgcgcggt    1080
tgagggtagg aaggcgttga gatcgagaag aagggacgtt tcggagaaag tgcgtttagt    1140
tgattttaga aattagagtt tttcgggatt tcgtcgagat tttttgtagg gcgttttaat    1200 ttgtttttttt attgcgtgtc ggcgtcgtag cgcgtgcggt ttagggtttg gtgatttcgg    1260
tttagttcgg cggtcgcggc gaggttttttg gcgtagtcgt ttggaatttc gtattagaat    1320
cgggatcgcg taaatgtttt ggttgaagtg ttatttttatt taagaaatat tgttgttagg    1380
aataaaatgg ggttttcggt gtttcgaagt attttttgaa attttttttaa aataatttat    1440 aaaaaatgtt tttgttttaa cgttttataa cgtttaagga aatatgtaaa tggtttgttt    1500
ttttatcgag atggtcgttt taattaatag tgtatatata tataataatt ttttaatttt    1560 tttttttttag agttaagtat tttattatat gtaaattata ataagaaaaa gattgtgtaa    1620
gattatgtaa gtcgattgat ttaaaatatt gagtttttaat ttaggttttt tgttttttta    1680
tttaataatt tttgtgtttg gattagattg gtgaagtagg ttatggaaat taataaaagta    1740 aaaaattaaa agtattttttt ttcgttattt ttttttttaa aattaaataa tagtcgtttt    1800
tttttgagta ggttttagtt ttaggttcga gtttttttgc gattattttta tagttatttta    1860 tagtagttgt tgttgttttt gtcgggtttt cgttttttgtt ttttttgggt cgttttttgt    1920
atataaaata tattttagtt ttttaattaa atttaaatac gatttcggta gaatttatat    1980
atttcgtggt gtatggattg tgtcggtgta ggggaaataa atattttttg gtatttaatt    2040
attgagttta attcgaaaaa tcgggattgg gttttttaggc ggtattttag gggttttaat    2100
ttggttcgcg ttttttttaga ttttggcgtt gagagcgttg ttttttgcggg tgggtggacg    2160 gagaggtaat aatttgtttt taataaaaat ttgtcgttat cgaatcgaaa gcgaagggga    2220
agggagaag                                                            2229
```

<210> SEQ ID NO 8
<211> LENGTH: 2229
<212> TYPE: DNA
<213> ORGANISM: Artificial Sequence
<220> FEATURE:
<223> OTHER INFORMATION: chemically treated genomic DNA (Homo sapiens)

<400> SEQUENCE: 8

```
tttttttttt ttttttcgtt ttcgattcgg tggcgatagg ttttttgttga aagtagattg      60
ttattttttc gtttatttat tcgtaaaagt agcgttttta gcgttaaggt ttggggaggc     120
gcgggttagg ttggagtttt tggggtgtcg tttaggggtt tagtttcgat ttttcgaatt     180
agatttagtg gttaaatatt agagggtatt tattttttttt gtatcgatat aatttatgta     240
ttacgaaatg tgtaaatttt gtcggggtcg tatttgaatt tagttagaga attggggtgt     300
gttttgtata aagagacga tttaaagaag gtagaaacga aaattcgata gaagtagtaa     360
tagttgttgt gggtgattgt ggggtgatcg taggaaaatt cgagtttggg attgaagttt     420
gtttaggaag gggcgattgt tgtttaattt tggagggagg gatggcgaag gaagatgttt     480
ttaatttttt attttgttaa ttttttatagt ttgttttatt agtttggttt aaatataaaa     540
gttgttaaat agaaaaatag agggtttgga ttaaaattta atattttaag ttaatcgatt     600
tgtatgattt tgtataattt tttttttatt ataatttata tatagtgaag tgtttagttt     660
tgaggaggaa agttggaaga attgttatgt atgtgtatat tgttagttag gacgattatt     720
tcgataaaga aatagattat ttatatgtttt ttttaaacgt tgtaaaacgt taaagtaaaa     780
atattttttg taagttgttt taagaaaatt ttagaagata tttcggagta tcggggattt     840
tattttgttt ttgatagtag tgtttttga atagggtgat atttttagtta gggtatttgc     900
gcggttttcga ttttaatgcg aagtttttaag cggttgcgtt aggaatttcg tcgcgatcgt     960
cgggttaagt cggagttatt aagttttgag tcgtacgcgt tgcgacgtcg gtacgtagta    1020
ggaaaataga ttaaaacgtt ttatagaaaa tttcggcgaa gtttcggagg attttggttt    1080
ttaagattag ttgggcgtat ttttttcggg acgtttttttt ttttcggtttt tagcgttttt    1140
ttgtttttag tcgcgcgtag ttttttgttttg gtggtaaatt gaaataagaa atggaaatat    1200
attggttttt gttgttgtta gggatgagag gttgttgacg ttcggcgcgt ttgttcgggt    1260
ttcgggtttt tttgtagatt tttggattgg ggtgtttgag gttaggagag gaggggata    1320
gttgttcgga gttttcgcgg tttagaggtt ttgggatgat ttatgggggg ggcgcgtttt    1380
gtttttggtga gttttcgtt tcgagggtag gcgaggtggg tgggtagggg agtgtatgtc    1440
ggagagaaga gagaacgttt aattagagag aattttttgt tttcggagtt ttagcgtttt    1500
tagttttta aatttttgtt taggaagtcg aaggatttag gttaggtaa cggtttgggg    1560
tgggcggta agagcgtcgt tttgtattcg gacgtcgttt gttaggcgtt atttggttat    1620
gtgcgttcgt agcgtagggt ttttcggtta ttagtatagg tttttatcga ggtgatagtt    1680
atcggattgg gaaattaata ttgcgaggat tcggttatgt gatgatatcg ttcgggggaa    1740
ttcgagtgga agtcgatcgt tttgtggtgt tattagatag gtgagaagta gttttttttaa    1800
atagggtttt ttgttggaag gaggaggtat ttttttttag ttagtgagtt ttttttagttg    1860
taatcggggt ttttttttaat attagttatc gcggttttta gaggtgtagt tcggtatatt    1920
ttttttttgt agatgtataa atcggggata tttttattttt tatttaagat gttttttttt    1980
tatttagtag aggggtgcgg agtaaaattcg ggataataat ttgcgtgttg tttggaagta    2040
ggttttttag aaaggatgat aaaaatttgg tgatgcggaa gaagtttttta ttgtgtttag    2100
gaaagggtag cggtttttta gttgtatcgg ttttggtttc ggttttttatt tttagtacgt    2160
tttgttattt taataaagag cggtttttttt atttgatttt aattcgtatt agttagcgtc    2220
gaggaaaga                                                           2229
```

<210> SEQ ID NO 9
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9

| | | | | | |
|---|---|---|---|---|---|
| gtttttggtg | agatatgtgt | tttataagtt | ttaatggaga | aaaatgtaag | tattttatt      60 |
| tttgaaattt | ggttatttga | gtaatgagaa | aatagttatt | tttttagga | tagtggtttt    120 |
| taattatggt | tatgtgtttt | tttaggaaaa | ttttaaaaat | atatatatat | taatgttttt    180 |
| gtgttatttt | tagggatttt | aagttttga | atacgaattt | tgtattagta | tttttaatt     240 |
| atttaggtga | ttgtgatgtg | aaattatgat | tgagttttat | tgttttaaga | tgaaataaat    300 |
| tttttttagt | attgaaatta | taaatttaaa | ttattaaaat | taattaaggg | tatgggaatt    360 |
| aataaggtat | agggaagttt | ttatattata | aaattatttt | tttaaattat | agttattgt     420 |
| ttatatgtta | tttgttattg | tagaaaaggg | tgaaaaaata | gtaaatttaa | ttattttag    480 |
| tttgaaaaat | tatttagaaa | tgaagatgac | gattttgaaa | tattgttaat | attatttgat   540 |
| ttataaataa | tgttttaata | tatttattat | atattgatag | atattttttt | atatgaatat   600 |
| tatatattaa | aattaaggta | ataatgtatt | tagaatatt | tatttatatt | tatgtatttt   660 |
| aagtaggtta | gaaattaaga | tatgagttat | taagtatgag | atgttaaggt | gtggggttag   720 |
| aaattatatt | gtattttatt | attaataatt | aatatatatt | ttaatattat | atatatttaa   780 |
| ttttaatttg | tatatttta | attatttta | attatgtgta | taaatataag | tatatatatt   840 |
| tttatgtatt | tatttattta | tatttttatt | tatttattta | tatagggat | ttttttaaat    900 |
| ttattattat | taaattatat | atttttattt | taatttttag | aataagtta | ggaggtaggt    960 |
| attgttatta | tttatatttt | ataaatgagg | aaattgttta | tagttataaa | gttattgtgt   1020 |
| tagatatatt | agaagtttaa | tatatatttg | gtgaatatat | gtataaaaat | agagagatag   1080 |
| atatgtataa | tagtttatt | ttatattgag | taaaagtttt | taatttgttt | tagaaatttt   1140 |
| tttgtgaaaa | ttgagtaaaa | atcgaggtat | tttttattt | gttatatagg | tataggtggt   1200 |
| atttattt | ttaataagg | atgaatattg | aaatgtggat | tttaaggttt | aattttagat   1260 |
| tttttgaatt | tttgatagtg | ggatttggaa | tttgtttatt | gttttaaagt | tttttaagga    1320 |
| atttatatga | ttaattaggt | ttagaaatta | ttggatttta | ttgtcgaagt | ttgagaatta   1380 |
| aagtttgggt | tttattgcgg | tttttatagaa | agggtaaatg | aagtattatg | gatagaattg   1440 |
| atacgttttt | agttagtttt | ttttttaga | agttaatagg | tagtaatata | gtagaaatta    1500 |
| gtgattatg | ttttgtgttt | tgaagttagg | tagaattta | tagagtttta | gtagtgttat    1560 |
| tgacgagatt | tgttttttgg | ggtaagttgt | ttgatgtttt | taaagttata | tttttttat   1620 |
| ataaatgag | ataatatttt | ttgttttata | ggggtgtttt | aaagattaaa | taaaaataat   1680 |
| atgttttatt | ttatatggta | taatgtttga | tatttaagaa | gtaaaggata | tatttttattt  1740 |
| ttattgaagt | aattagaaag | tatgaaatta | tgaaggagat | aagagttttg | attggtagtg    1800 |
| tattttattt | ttttaggttt | attattttat | tttaaattat | ttttgttgga | gaataatttt   1860 |
| taagttttt | atttaagttg | tgagtaattt | tatattttat | aatgatgttt | tttttatgag   1920 |
| aaaaaaaat | gttttaagt | tttttggaga | aaatatattt | gtattatttt | tattgaaaaa   1980 |
| tttaataatt | ggattttgtt | ttttgtatt | aatttagag | tgtatatgtt | ataaataaag   2040 |
| tgttttagtt | taagaagatt | gaaagtaaat | atggtatagt | attttaaaat | aagaattttg   2100 |
| taaatatatg | gtatgattgt | gttatattat | tagtaattat | atgatacgta | atgtaaagta   2160 |

```
tagtttatag atttaaattt aattttaata agtaaattga ttttgttttg ttggggaaaa    2220
gttaaagtat taatttaatt gttaatgtag ttttgtttat ttttttggta tttagtgata    2280
agtttaaata atgtatatat ttttatttat atatttagta ataatttt ttgtttaatg     2340 agtgatgttt ttttgttatt tggtggtgtt tgttagtttt agaatttgtt ttttggtggt    2400
attataatat taagtataga gtaagtgtaa taaaattgta gtattttat tgaaaaggtt    2460 ttgttttaaa ttgtttaata atttaaagga ttttgtgga agtaatcgta tttgttaatt    2520
agttataatt agtaattaat ttttttggag ttttaattta tttttggtaa aacgttttag   2580
gaagagtata tattattaga aagtatgtta aaaattatt tagtagaaaa tttaaaaata    2640
gttttttttt gttaagaggt ttttaaaat tttatttata tagttaaatt ttgaaatttt    2700
agtaggtttt gttttattat tataattatt gtataaatat tttaaggat tttgttttta   2760 gttttaagta tgatttattt ttataagttt gattagttat tatattagtt ttgttatgga   2820
aaatgatatg ttttttatttt ttgttgtaga gttgttaaat tttgatttat atttatgttg   2880
ttttttttgt tgaaagtttg tagcgaaaga aattttaat ttttgtttt gtaatattag    2940 ttggtagttt tatttaatgg gtattttgtt tttttaaaga atttagttgt tttgtttaga   3000
agtcgatttt ttgatgtttt taacgtttgg tttaattgat ttgttttaat ggagttttcg   3060
tcggtgagga gcgagatgtt atcgattaga atgttgggat ttgttgttta attgttagga   3120
gtgagagata ttgagattta gaaattttg gaggtgggag gggagaggga tagtttcgga    3180
cggaggcgga gatgtaagat aaagggatgg atttatata ggaaaaaaaa aaagatttcg   3240
ttgaggtatt gaggtgttgt acgattatat ttttaaagg agaagttaaa aagtaaggaa    3300
gtgggaggag gttggaggtt aaagtattta aaaggattat tcgggtataa tttgtttttt    3360
tgttggtgtt tgtaaaggat agatagtttc gttttaaag tatatgaatg ttttttttaa    3420
gtgattggga atggatatta attgtttgtt aaatgttatt aaatgttttt ttaaatttag    3480
gggatataga aagagggta taaaaggaga atttaaatag aaaaagggag gattcggagg    3540
tttttgaaag cgggggaga agaaggagga gggataatag agaggaatag agaaggagag    3600
cggagagaag ataaataaaa ataaaatag gaattattga ataattatat attaaaaaga    3660 aagtttttt ttatggggta tttaaaatat tgagattgta atagtgattt cggttatgga    3720
agaaagatgt ttttttttat ttttgttttc gaaagttttt ggtttcgtta ttggcgatta    3780
aaattttatt aggttaaaga gtgtgtttaa ttgtttgaag aatgtagtag acggaaggcg    3840
ggtttcgtta tgtcgtttgt tttttcgtt ggagagaatg aaagaaacgc gtagagttag    3900 agattttgt cgagttagat tttttttcgt cgttttaggt tatcggttat tcggtaaaga   3960
ttcgagtaag gaacgtaggg ttattgtttg ggttaataaa tggagttcgt ttttttttt    4020 tcggacgtcg ttgttcggtc gatgtttcg gtaatttatt cgcggcgtat gtagaggagt   4080
tttttttttt tttttagatt atttgtttcg attaatttga ttttttaaat atatttgatc    4140
gtatttttta ggtggatata ttaataggtt acgggttgga gaggagcggg tgatgaggag    4200
agggatttaa atttgcgaac gtttgggttg ggtcggagtt gcgggggtt tgggaggaga    4260 gagggagaa gagagaagga aggagagcgt ttgtcgggat ggttgagttg tttcggcgag    4320 tagtttggg gttgtacgtt tttgtgggag atgttgttgt tgttttagg tcggtaagag    4380 cggttttaat attatcgttt tttattttt ttttgtaaa ttttagaga aacgttttg    4440 gttttttcgt cgcgatattt ttagtttgta ttttttata gttaggcgg gcgtttcg    4500 tacgttggag cgtcggtcgt tagtaggacg tttttttcg cgtcgattcg tttttttttg    4560
```

```
ttttgttgtt gttgttttttt tgatattttc gtttttatta tttttagttc ggagagacgt   4620
tatttagtcg cggttcgtat tcgcggttcg gggttacgcg cggaagaggg gcgttagttc   4680
ggatttcgtt ttcggtaggg ggcgttttgg agcggagagt gaggcgaatg gtatatgagt   4740
gtgcgggtag tttattttga agttcgagtt ttttatttga gttatgtttc gtttagtttt   4800
attcgggtta gcgtttggcg agcgagttta tttgtggttt tcgcggtcgt tttttttttg   4860
tattttgta tttattcgtc gatttttttt tttcgggatt tgtattttgt tttattaatt   4920
agagttcgat tgtttttttt tacgtgattt cgggcgggtt gaggatttgt tgttttttaa   4980
acgttagagg gatgcgggcg gtagagttcg agaggcggtt gtcgggttgc ggggcgtttt   5040
gattttttt ttattttgtt ttttcgggtt ttattcgttt gttttttggat tttcgttttt   5100
ttttgttttt cggttttta gagtttttt tttatggtag tagttttttcg cgttttcggc   5160
gtagtttttt agcggacgat ttttttcgttt cggggttgag tttagttttt ggatgttgtt   5220
gaaattttcg agattatgcg cgggtttggt tgttgttttt tcgtcgggtg ttattgttat   5280
cgtcgtcgtt tttgttgtcg tcgttcgcgg gatgtttagt agttcgttgt tcggttttcg   5340
cgattttgtg tttttcggaa gtcgtttgtt gttgtagagt tgtacgaatt agttatggtg   5400
ttgtgggagt tttcgcggta gtgtagtagt tggatattt gcgagggttt ttgttggttg   5460
ttgttgttgt tcgttatgtt atttatcgta gttcgttcgg tgaagttcgt tgttttttt   5520
atttttttaa gtgattgtta aacgtttatc ggttggaatt gttttggtaa gtttagaatt   5580
ttcgttttcg atttttaat ttcgtagaag aatacgcgta tttagtatag attagtttat   5640
tttagcgcgt tttttagtt ttttattttt tattgtttta gatttttaat attatttatt   5700
tttatttaga gaaataaggg gaattgttgt aggttcgggg gtgaggggtg gttttgggat   5760
gggtagaaag tgtaggtgta gtaggaaatt tttgtatgtt tgcgtttata ttggagttgc   5820
gaggattttg agaaatatta aacgggatgg tttttttgggt ttattgtttt gaaagagtat   5880
taatttagg ggaaatattg aaatagaagt tttgttatta ttaaagaaaa aagttttatt   5940
aggatgagga agaaataatt ttatgagaaa gaatgagcga gaaagtaata aattaaatgg   6000
tgattgtagg ggaatcgttg attttttggta aaggtgttat gaggtcgtat tggttttcg   6060
ttgaagatta ggttatatag attttagagg agttgggttt taatagaatt tttttttttt   6120
tttttttttt tttttttttt tttttttttt tttttttatt tatttatttt tttttttttt   6180
ttatttttt tttttttagg cggtaaaaga tattggtttt gtagtttaga tatgtttttt   6240
ttttttgtttt tttaagtttt aaggtagtat aggggagttg agaaaaagaa tattttgcgg   6300
gttttttagg tcggagtggg tatgattgag gttggttagg ttttatgtag gcgagtcgag   6360
ggcggaatcg attttagtgg gcgttgattt tttattttt ggataggttt ttgtggagtg   6420
ggttaggtat tttttttgtt cgttcgggtt ttttagatt ttgacggcga acgtttggta   6480
ggtttcgttt tgttgaagtt ttttaattaa atagggttag aggatgggag ttgttgtatt   6540
tttagttggt atagtattcg gtttgatagt ttgtagtata gggtgtatgt aattttttat   6600
ttttttgtgaa tataattttg ttgtagttaa atttggtttt gaataaagtg ttttttaaag   6660
atgtatataa gttgaagtgt atgtaatttt agagaggagg gaatgattaa ttgtaatta   6720
gggtgaaagt ttgtatagtt tttagttatt attgatgtaa atgttaaaag gaaaattatt   6780
atgtattatt ttaatttatt ttttataaag ataagttgag atatgtaatt ttattagatt   6840
tgggttaata gattgttttt tttttggta gttttaaaat ttggtatttt aataaaattt   6900
aatatgtttt tataattttt tgatttatgc gtatatgtgt gttgtttttg aaagaataag   6960
```

-continued

```
ttttattttg ttattgttta attatttttt agatgtttta ttatggtaat aattatgagt    7020
ttgtaaaaat aattttttgga aatgttgatg gttttgtagt ttaatataga ttggtttgtt    7080
ttatttttag ttttttgtatt gttttaggaa ataattaatt taaatgtgaa gttgatattt    7140
gtaattaaga aattatatat ttattagata ttttaagggg gattgtataa attaaagaga    7200
ataaattggt tttgtagata ggttgttaag aatttggtat ttcgttttta tttttgttaa    7260
tttagaggtg attaattttt atttgagtta aatagattat tatagaaaat attgtgtttg    7320
tttattttta ttattgaggt tttgttttt tttgtttgg atatattttta aataaggggt    7380 tgttttagtc gttgaagtaa aagaataatt aaagatgggg aaatggtaaa agggtattta    7440
gagattatta ttagtttttt tttaaaatgt ggagttttgt ggttataaat attgtttatt    7500
taatgagtaa aaaataaaaa taaaaaaaaa ataggaagta aatgttaagt ttttattttat    7560 tattgttagt attaacgtaa gttttaaaaa atagtattat tagaaaagga tattaaagga    7620
gaattgatta gaaaagaatt gtggaaaatg gaaacgaata ttgattattt aattagattt    7680
tgaggttatt agtagatagt gattttgtag tatagttata gttgttggat ttaaaattta    7740
ggataagtat tttaaagttt taaagtagtg ttttttttttg ttaaaaattt gtaagatgtt    7800
ttaatgattg gagtgttttt tttgaatttg agg                                 7833

<210> SEQ ID NO 10
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10
ttttaaattt aaagagaata ttttagttat taaaatatt tatagatttt taataaaaaa       60
aagtattatt ttgaagtttt aaaatatttg ttttaaattt taaatttaat aattatagtt      120
gtattgtaag gttattgttt attgataatt ttaaaattta gttaagtgat taatattcgt      180
ttttattttt tataattttt ttttagttaa tttttttttta gtattttttt ttgatagtgt      240
tattttttaa agtttgcgtt aatattgata gtggtgaatg aaagtttaat atttgttttt      300
tgtttttttt ttattttttat ttttttgttta ttaggtggat aatatttatg attataaaat      360
tttatatttt ggaaaagagt tagtgatgat ttttgaatat ttttttatta tttttttatt      420
tttaattgtt tttttgtttt aacgattgaa ataattttt atttgaaatg tatttagata      480
aagaggaaat aaagttttaa taataaagat aaataggtat agtgtttttt gtgatggttt      540
gtttggttta aatgaagatt gattatttt aagttaatag gggtggaagc ggggtgttaa      600 gttttttgata atttatttgt aaaattagtt tatttttttt agtttatgta gttttttta      660 aaatatttgg taaatatgta atttttttgat tgtaaatgtt aatttatat ttaagttagt      720 tattttttaa aataatgtaa gggttaggaa tgaagtaaat tagtttgtgt tggattataa      780
agttattaat attttttaaaa attgttttg taggtttata attattatta taataaagta      840
tttaaaaagt gattaggtaa tagtaaagtg aaatttattt ttttaaaaat aatatatatg      900
tacgtatgaa ttaagaagtt atagaaatat gttgagtttt attaaaatgt taaatttaga      960
aattgttaaa aaagagaata attttattgat ttaaatttaa tagggttgta tattttaatt    1020 tgttttttgta aaggataaat tagaatgatg tataataatt tttttttttgg tatttatatt    1080 agtaataatt aggaattata taggtttttta ttttgagtta tagttggtta ttttttttttt    1140 tttaaagtta tatatatttt agtttatata tattttttgaa agatattta tttagagtta    1200
```

```
gatttaatta tagtaaaatt atatttatag aagatgaaaa attatatata ttttatatta    1260
taggttgtta aatcgaatgt tatgttagtt aggagtgtag taattttat tttttggttt     1320 tatttaatta ggaagtttta gtagagcgaa gtttgttaag cgttcgtcgt tagaatttga    1380
aggaattcga gcgagtaaga agagtgtttg atttatttta tagaagtttg tttagaaatg    1440
gaggagttag cgtttattga agtcggtttc gttttcggtt cgtttatatg gagtttgatt    1500
agttttagtt atgtttattt cggtttggga gattcgtaaa gtgttttttt ttttaatttt    1560
tttgtattat tttgaagttt agggaagtaa agagaggggt atatttggat tgtaaaatta    1620
atgttttttg tcgtttagga gagaagggaa tgagagagag agagagatag atagatagag    1680
agagagagag agagagagag agagagagag agagagagag agaaatttta ttgaaattta    1740 gttttttttag aatttgtgtg atttggtttt taacgggaga ttagtgcgat tttatggtat   1800
ttttgttagg aattagcgat ttttttgtag ttattatttg atttattgtt ttttcgttta    1860
ttttttttta taaagttatt tttttttat tttagtaaga ttttttttt taatgatgat      1920 aaagttttg tttagtgtt ttttttagga ttggtgtttt tttaaaatag tgaatttaga      1980
aaattatttc gttaatatt ttttaaaatt tcgtagtttt taatgtaagc gtaagtatgt     2040
aaaggttttt tgttatattt gtattttttg tttattttag aattattttt tattttcggg   2100
tttgtaatag tttttttttgt tttttggat agaggtgggt ggtattaggg gtttagggta    2160
gtaggaggtg agggggttgag gaggcgcgtt agggtaggtt ggtttgtgtt ggatacgcgt   2220 gttttttttgc ggagttaaag ggtcgggggac ggggtttg gatttattag agtaattttta  2280 gtcggtgggc gtttggtagt tatttaagga ggtagggaaa gtagcgagtt ttatcgggcg   2340
ggttacgatg agtagtatga cgggtagtag tagtagttag taaaagtttt cgtaaagtgt   2400
ttagttgttg tattgtcgcg gggatttttta tagtattatg attagttcgt gtaattttgt  2460
agtagtaaac ggttttcgag gaatatagga tcgcggggt cgggtagcgg gttattgagt   2520
atttcgcgga cggcggtagt agaggcggcg gcggtggtag tggtattcgg cggggaagta   2580
gtagttaaat tcgcgtatga tttcgagagt tttagtaata tttagggatt gggtttagtt   2640
tcggagcgag agggtcgttc gttgagaagt tgcgtcggag acgcgggaag ttgttgttat   2700
aaggagggag ttttgggaag tcggaggata ggaggagacg ggagtttagg ggtagacgag   2760
tggagttcga ggaggtaggg tggagggaga gttaaggcgt ttcgtagttc ggtagtcgtt   2820
tttcgagttt tgtcgttcgt attttttttgg cgtttgggaa gtagtaggtt tttagttcgt  2880
tcggggttac gtgggaagag gtagtcgggt tttgattggt ggagtaggat gtaggtttcg   2940
ggagggaggg gtcgacgagt aggtgtaagg atgtaaggag gaggcggtcg cggaagttat   3000
agatgggttc gttcgttagg cgttggttcg agtggggtta ggcggggtat ggtttaaatg    3060
agaagttcgg gttttagggt gggttattcg tatatttata tattattcgt tttattttttc   3120 gttttaggac gttttttatc gaaggcgggg ttcggattag cgttttttttt tcgcgcgtga   3180 tttcgggtcg cgagtgcggg tcgcggttgg gtggcgtttt ttcgagttgg agatggtggg   3240
ggcggaggtg ttagaggagt agtagtagta gggtagagag gggcgagtcg gcgcgggaga   3300
gggcgttttt ttggcgatcg gcgttttagc gtgcgggagc gcgtcgttta ggttgtaggg   3360
ggatgtaggt tgggaatgtc gcggcggaga ggttagggac gttttttag ggatttatag    3420 gaaagagggt gagaggcgat ggtgttagaa tcgttttttgt cgatttggaa gtaatagtag   3480
tattttttat aagagcgtgt aatttaagg ttgttcgtcg aggtagttta gttatttcgg    3540
taggcgtttt tttttttttt tttttttttt tttttttttt ttaggttttt cgtagtttcg    3600
```

```
atttagttta agcgttcgta ggtttgaatt ttttttttta ttattcgttt ttttttagtt      3660
cgtagtttat tagtgtgttt atttgggagg tgcggttaga tgtgtttgga aggttagatt      3720
ggtcgggata agtggtttga gagaaagaga aaggttttt tgtatacgtc gcgggtgggt       3780
tgtcgggagt atcggtcggg tagcggcgtt cgggaagggg agagcgggtt ttatttgttg      3840
gtttaggtag tgattttgcg ttttttattc gggttttgt cggatggtcg gtgatttggg       3900
gcgacgagag aaggtttaat tcggtaggag ttttggttt tgcgcgtttt ttttattttt       3960
tttagcggga agggtaaacg gtatagcggg attcgttttt cgtttgttgt atttttagg       4020 tagttagata tatttttag tttaatggaa tttagtcgt tagtaacggg attaagagtt        4080
ttcggggata agggtggaga ggaatatttt tttttatga tcggggttat tattgtagtt       4140
ttagtgtttt ggatgtttta tagggaagag tttttttttt ggtgtgtgat tatttagtga      4200
tttttgtttt tgtttttgtt tattttttttt tcgttttttt ttttattttt tttttgttat     4260
tttttttttt tttttttttt tcgttttaa aagtttcgg atttttttt tttttattta         4320 aatttttttt ttgtgttttt tttttgtgt ttttgaatt taggagagta tttgataata        4380
tttaataggt aattagtgtt tattttaat tatttaaaag aggtatttat atattttgaa       4440
aacgggatta tttatttttt gtagatatta gtagaaaaat aaattgtatt cgagtaattt      4500
ttttaagtat tttaattttt aattttttt tattttttg ttttttaatt tttttttga         4560 gagatgtgat cgtgtagtat tttagtgttt taacgaaatt tttttttttt ttttgtgtga     4620
aatttatttt tttattttat attttcgttt tcgttcgaga ttgtttttt ttttttttat       4680 ttttaaagat ttttgaattt tagtgttttt tatttttggt aattaagtag tagattttag     4740 tatttagtc ggtggtattt cgtttttat cgacgaagat tttattaaaa tagattaatt        4800
agattagacg ttggaggtat tagaaaatcg gttttagat agagtagtta aattttttaa       4860
ggaaatagaa tatttattag atagagttgt taattaatat tgtaaaataa ggaattagaa      4920 attttttcg ttataggttt ttagtagaga aggtaatata aatatagatt aagatttaat       4980
aattttatag tagagaatga gaatatgtta tttttatag taaggttggt gtggtaatta       5040
attaggttta tgaaaataag ttatgtttga aattaaaggt aaagttttta aaagtgttta      5100
tgtagtaatt atgataatga aataggattt gttaggattt tagagtttgg ttatgtaagt     5160 agaatttag agaattttt agtagaggaa aattgttttt gaattttttg ttaagtaaat        5220
ttttggtata ttttttaata atatatgttt ttttaagac gttttgttaa aagtaagtta      5280
aaattttaaa ggagttaatt attggttgta attggttaat aaatgcggtt gttttttatag    5340 aggttttta aattattaaa tagtttgaag taaagtttt ttaatgggaa tgttgtaatt       5400
ttgttgtatt tattttgtat ttagtgttat agtgttatta agaaataaat tttgaaattg     5460
gtaagtatta ttaagtggta gaagaatatt atttattgag tagagaattg tattattgaa     5520
tatgtaaata aaaatatata tattatttag atttgttatt aggtattaaa gaagtagata     5580
agattgtatt agtaattgga ttagtgtttt aattttttt tagtaaggta aaattagttt      5640
atttattaga attaaattta agtttatgaa ttgtattttg tattgcgtat tatatgattg     5700
ttagtaatat gatataatta tattatgtat ttgtaaaatt tttattttaa aatattatat     5760
tatatttatt tttaattttt ttgagttaga atattttatt tgtggtatat atattttaga     5820
attgatgtag aggagtagag tttagttgtt agatttttta gtagaaatag tgtagatata     5880
ttttttttag aaaatttaag aatattttt tttttatgg aaagaatatt attataaagt       5940
gtgagattat ttatagttta agtagggggt ttgggagtta tttttttaata agaatagttt    6000
```

-continued

```
aagataaaata aatgaatttg ggaaaataag atatattgtt aattagaatt tttatttttt    6060
ttatgatttt atatttttg attgttttaa taaaggtaag atgtattttt tgttttttag     6120
gtgttaggta ttgtgttatg taggatagaa tatgttattt ttatttaatt tttaaaatat    6180
ttttatgaga taaagaatat tattttattt tatataaaag gaatatggtt ttgaaagtat    6240
taggtaattt gttttaagaa ataaatttcg ttagtgatat tgttgggatt ttgtgaaatt    6300
ttgtttgatt ttagagtata agatataagt tattaatttt tgttgtattg ttgtttgtta    6360 gttttgaga ggggaaatta attgggaacg tattagtttt gtttatgata ttttatttgt     6420 ttttttgtg gagtcgtagt aaggtttaaa ttttaatttt taaatttcgg taataagatt     6480
tagtgatttt tgaatttggt tgattatatg aatttttga gaaatttga aataatagat       6540 aaatttaag ttttattatt agggatttag aaaatttgga gttgggtttt gggatttata      6600
ttttaatatt tattttgtt ggagaagtaa ggtattattt atatttatat gataaatgaa      6660
aggatatttc gattttgtt tagtttttat agagaggttt tgagatagg ttaaaagttt       6720 ttatttagtg taaagatgag ttgttgtata tgtttgtttt tttgttttta tgtatatgtt     6780
tattaaatat gtattaagtt tttaatatgt ttgatatagt aattttgtga ttgtagataa     6840
tttttttatt tgtaaaatgt gagtaataat aatatttgtt ttttgggttt gttttaaaga   6900
ttaaaataaa aatgtatggt ttaatggtag tggatttggg gggatttttt atataaataa    6960
gtgaatggag gtatgaataa ataaatatat aaagatgtgt gtatttatat ttatatatat    7020
aattaaaaat agttaaagat gtataaatta aagttaaatg tatgtgatat tgaagtatat    7080
gttgattatt gataatgaag tatagtataa ttttaatttt tatattttaa tatttatat    7140 ttaataattt atattttaat ttttagttta tttaagatat atagatatag atagaatgtt   7200
ttaaatgtat tattgtttta gttttaatgt ataatatta tatgaaaaag tattattag     7260 tgtgtagtaa atgtattaga atattattta taggttaaat gatattgata atgttttaga   7320
gtcgttattt ttatttttgg ataatttttt aaattgagag taattaaatt tgttattttt   7380
ttattttttt ttataatggt aaataatata taaataatga gttgtgattt aaagaaataa    7440
ttttataatg taaagttttt tttatgtttt attgattttt atgttttaa ttaattttgg     7500 tagtttaagt ttgtgatttt agtgttgagg aaagtttatt ttattttaga gtagtggggt    7560
ttagttatga ttttatatta taattatttg gataattaaa gaatattgat gtagagttcg    7620
tatttaaaga tttggaattt ttagaagtga tatagaagta ttggtatata tatttttta    7680 aagtttttt ggagaaatat atagttatga ttgagaatta ttgttttggg gaaagtgatt     7740
atttttttat tatttaaata gttaagtttt aggaggtaaa atatttatat tttttttat     7800 taaaatttgt aaaatatata ttttattaaa gat                                  7833
```

<210> SEQ ID NO 11
<211> LENGTH: 5666
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11

```
aaaattagaa ttttttatttt tttgcgtttg ttatattttt tagtgttgtt taatttttt      60 ttgtaagtga gggtggtgga gggtgtttat aattttttta gggagtaagt ttttttggt      120 tttttttttt tttttttttt tttttttttt tgagattaag tttcgttttt gtttttagg      180 ttggagtgta atggcgcgat ttcggtttat tgtaattttc gttttttttt gggtttaagc     240
```

```
gattttttta tattagtttt cgagtagttg ggattatagg tatgcgttat taagtttcgt      300
taattttgta ttttttagta gagatagggt ttcgttatgt tggttaggtt tgtttcgaat      360
ttttggtttt aggtgattcg tttgtttcgg ttttttagaa tgttgggatt atagacgtga      420
gttatcgtat tcggattttt tttttatgta atagtgataa ttttatttaa agtatttttt      480
tttttttttg agtcggagtt ttattttgtt atttaggttg gagggtggtg gcgcgatttc      540
ggtttattgt aattttgttt tttcgggttt aagcgatttt tttgttttag tttttttgagt     600 agttggaatt atacgtgc gttattatgg ttagttaatt tttgtatttt tagtagagac        660
ggggtgttat tattttggtt aagttggttt cgaattttg attttaggtg atttgttcgt       720
ttcggttttt taaagtgttg ggattatagg tgtgagttat cgcgttttgt tttaaagtat      780 tttttttta tgttttaaaa taagattgta agttagtttt taaagcggat aatttaagag       840
ttaataggta ttagtttagg atgtgtggta ttgtttttaa ggtttatatg tattaatata      900
ttatttaaat ttataataat ttttataaag taggggtat ttatattttt tttttttttt      960
ataattacga aaatgtaag gtattttag taggaaagag aaatgtgaga agtgtgaagg       1020
agataggata gtatttgaag ttggttttttg gattattgtg taattttgtt tttagaatat    1080
tgagtatttt ttttggttta ggaattatga ttttgagaat ggagttcgtt tttttaatga    1140
tttttttttt attttttat ttgtttatag gtagaatttt tttcgttcg tattaaataa       1200 attttatttt tttagagttt gttttatat taggtaatgt atacgtttga gaattttttg      1260
ttttagatag tcgttttata cgtaggaggg aagggagg ggaaggagag agtagttcga       1320 tttttttaaaa ggaattttttt gaattagggt ttttgattta gtgaatttcg cgttttgaa    1380 aattaagggt tgagggggta gggggatatt ttttagtcgt ataggtgatt tcgattttcg     1440
gtggggtttt tataattagg aaagaatagt tttgtttttt tttatgatta aagaagaag     1500 ttatatttt ttttatgatat taaatatttc gatttaattt ggtagttagg aaggttgtat    1560
cgcggaggaa ggaaacgggg cggggcgga tttttttta atagagtgaa cgtatttaaa      1620 tacgttttg ttggtaggcg ggggagcgcg gttgggagta gggaggtcgg agggcggtgt     1680 gggggtagg tggggaggag tttagttttt tttttttgtt aacgttggtt ttggcgaggg    1740
ttgttttcgg ttggtgtttt cggggagat ttaatttggg gcgattttag gggtgttata     1800
ttcgttaagt gttcggagtt aatagtattt tttttcgagta ttcgtttacg gcgttttttt   1860
gtttggaaag atatcgcggt ttttttagag gatttgaggg ataggtcgg aggggttttt    1920 ttcgttagta tcggaggaag aaagaggagg ggttggttgg ttattagagg gtggggcgga   1980
tcgcgtgcgt tcggcggttg cggagaggg gagagtaggt agcgggcggc ggggagtagt    2040
atggagtcgg cggcggggag tagtatggag ttttcggttg attggttggt tacggtcgcg    2100
gttcggggtc gggtagagga ggtgcgggcg ttgttggagg cggggcgtt gtttaacgta     2160 tcgaatagtt acggtcggag gtcgatttag gtgggtagag ggtttgtagc gggagtaggg    2220
gatggcgggc gattttggag gacgaagttt gtagggaat tggaattagg tagcgtttcg    2280
atttttcgga aaaggggag gtttttgg gagtttttag aaggggttg taattataga       2340 tttttttttg gcgacgtttt ggggtttgg gaagttaagg aagaggaatg aggagttacg     2400
cgcgtataga ttttcgaat gttgagaaga tttgaagggg ggaatatatt tgtattagat    2460
ggaagtatgt ttttattag atataaaatt tacgaacgtt tgggataaaa agggagtttt     2520
aaagaaatgt aagatgtgtt gggattatt agttttaat ttatagatat ttggatggag    2580 tttattttt ttattaggag ggattattag tggaaatttg tggtgtatgt tggaataaat    2640
```

```
atcgaatata aattttgatc gaaattattt agaagcggtc gggcgcggtg ttttacgttt    2700
tgtaattttt ttattttggg agattaaggc gggggggaatt atttgaggtc gggagttcga    2760
gattagtttg gttaataggt gaaatttcgt ttttattaaa aatataaaaa gtagtcgggg    2820
gtggtggtag gcgtttgtaa ttttagttat tcgggaggtt gaggtaggag aatcgtttga    2880
attcgggagg ttgaggttgt agtgaatagc gagatggagt tattttatttt tagtttgggt    2940 gatagagtga gattttgtcg aaagaaagaa agagagaaag agagagagaa aaattattta    3000
gaagtaatta tatattgtgt ttatttttaa ttgagtaggg taaataaata tatgtttgtt    3060
gtaggaattt aggaaataat gagttatatt tatgtgatta ttttagaggt aatatgtagt    3120
tattattttg ggaatatttg ttaatatttt tgttttttta ttattttag tttatttgat     3180 atagtttatt tgtgataaga gttttaatt ttttatttt gaatagaggt gttttttttt      3240
tttttatttt tgttttgtga gggagttagg ggaggattta aaagtaatta atatatgggt    3300
aatttagtat ttttaaaatt ttgttaatag tttgaattcg ggagtttggt tttgtagttt    3360
tataatattt tagaagagat ttttatttgtt taaaaataaa aaggaaaaag aaaagtggat   3420
agttttgata atttttaatg gagaagggag aagaatatgt agaaaagggg aaatgatgtt    3480
ggtttagaat tttaattata ttggtgttta ataggaat atttatttat ataatattt       3540 aaagtattaa atttatatta gtatattatt aaatggatat attattaaat gggtttaagt    3600
attttatata ttttaattta attgatttat tttttttttg ttttggattt ttattatgat    3660
ttaaatattt atatatgggt tatttttttag attttttata ttatgaaata taagaaaaat   3720
ttttaaggtt agttttatga ttaagacgaa ggatttatt gaatatataa aataataaat     3780
atattgtaat attttgtttt tttttttgta gttgtaattt ggtttgttta tattttttt     3840 ttgttttttt gaaaattgag ttagttttat ttttttagga taggatttaa taattataat    3900
ataatttagt ataattttt gatttaggta aattatgtaa tttgtgttta gtatgaaatg     3960
tatttaaaaa taagtaattt tttttttaata ttattttt taaattaata taataaataa     4020 tagttattt aaaataaatt gtttatttt attatgtagt attttaaaattt taaggttgtt   4080 atgattgtag atagtatttt aaaattttt tttggaaatg gttttgtttt taagatgatt    4140
taggaattaa agaggtgatt atttttttgtt taatgaattt ttaaattata aatttgggaa  4200
gtgttttagt tttttattgt tgttgttata aattattata aatgtgttag ttaaaataaa   4260
tataaaatta ttatttttata gttttagaga ttagaagtta aaaatgggtt tataaggttt   4320 tattttttt ggaaattta aggggtaatt tgttttttttg ttttttttag ttttttagtga   4380 ttattaaatt ttttggttta tggtttttgt atttttttttg tggtttgtgt tttttatttt    4440 gtatttttt tttgattgtg atttttttaat aaaaatattt ggggtatgt tgggtttatt    4500 ttgaaaattt tggataattt tttttaagat tattaattaa attatatttg taaagttttt   4560
tttgttatat aagttaatgt attaaaagtt tttgaggatt aggatataga tattgggggt   4620 ggggggtat tatttagttt attataggaa ggaatttag ggttaattaa attagttttt    4680
ttattttata tttgaagaaa ttgaagttt ggaattggag agtattatgt taaatgaaat    4740
aagttaaata tagaaagata aatattata gtttttatt atttgtgaaaa tataaaataa    4800 ttatattttt agtagtaaag agtagaatgg tggttattag agttggggg tgggaggaat    4860 ggggagatgg taattaagat ataaagtttt agttaagatg ggaggaataa gtttgattgt   4920 ttttttttgag atgtgtttta tagtatgatg aatatagtta aatagtaaat tttaaatgtt   4980
tttatttgat aaaaatgtta aatatttgag atgatggata ggttatttag tttgatttaa   5040
```

```
taatttttta ttgtgtttaa agattataat tttatattgt attatataaa tatatataat    5100
tgtattattt taatatataa ttttaaaatt aatatatga aaaagaaatt gaagtttaat    5160
atttttagaa gttaagtgta atttaaaagt tttgtgagaa tttgttttaa taaataaata    5220
agtttttttt ttttaataat tattatattt tgcgtttgga tatatagtag tgaataaaaa    5280
aaaaaaaaaa aaaaaaaatt tttaggttta atataatttt aggaagaaat tttagtagtt    5340
gtattttagg ggaaatatag gaagttagtt tggagtaaaa gttagtttgt ttttgttttt    5400
ttgttatttt gttcgtgttt tatagtgttt tttgtttgtg acgatagttt cgtagaagtt    5460
cggaggatat aatggaattt attgtgtatt gaagaatgga tagagaattt aagaaggaaa    5520
ttggaaattg gaagtaaatg taggggtaat tagatatttg gggtttgtgt ggggggtttgt   5580 ttggcggtga gggggttta tataagtttt ttttcgtta tgtcggtttt tatttggtt    5640 ttgattattt tgttttttttt ggtagg                                       5666
```

<210> SEQ ID NO 12
<211> LENGTH: 5666
<212> TYPE: DNA
<213> ORGANISM: Artificial Sequence
<220> FEATURE:
<223> OTHER INFORMATION: chemically treated genomic DNA (Homo sapiens)

<400> SEQUENCE: 12

```
tttgttagag agaatagaat ggttagagtt agggtggggg tcggtatgac ggaaaggaag      60
tttgtgtaga gttttttat cgttaagtag attttatat aagttttagg tgtttaatta       120
tttttatatt tgttttagt tttaattttt tttttgagt ttttttatta tttttagta        180 tataatgaat tttattatat ttttcgaatt tttgcggagt tgtcgttata ggtagagagt     240
attgtgaggt acgggtaaaa tagtaaaggg gtagggatag attgattttt attttaggtt     300
aattttttgt attttttttg agatataatt attgaaattt tttttgaaa ttatgttagg     360 tttggagatt ttttttttt ttttttttt tgtttattgt tgtatattta agcgtagaat       420
gtggtaattg ttaaaagag aaatttgtt tgtttgttaa aataaattt tataaaattt        480 ttaagttata tttagttttt gggaatgttg aattttaatt ttttttat tatattagtt       540 ttaaaattat atattgggat agtatagttg tatatattta tgtggtataa tatgaagtta    600 tgattttga atataatggg gaattattaa gttaagttaa gtaatttatt tattatttta     660
aatatttgat attttgtta aatgagagta tttgggattt attatttagt tatatttatt    720
atgttatgaa atatatttta aaaaaataa ttaaatttat ttttttttat ttaattgagg     780
ttttatattt tgattattat ttttttattt tttttatttt ttagtttag taattattat     840 tttattttt attgttaaga atgtaattgt tttatatttt atagataagt gagaaatatgt    900 gatatttgtt tttttgtgtt tggtttattt tatttagtat aatgtttttt aatttttaaaa  960 ttttaatttt tttaagtata aaataagaag gttagtttaa ttaattttaa aattttttttt  1020 tgtggtaggt tgaataatgt tttttatttt ttaatgttta tgttttaatt tttaaaaatt  1080
tttaatatat taatttatgt ggtaaaagag gttttgtaga tgtgatttaa ttaatggttt   1140
tgagggagat tatttagaat ttttagggtg ggtttaatat aatttttaagt gttttttatta 1200 gagggttata gttagagaga agatataaga atggaagtat aggttataga gaaaatatag   1260
agattatgag ttaaggaatt tgatggttat tagaagttgg aaaagataag gaaatagatt   1320 gtttttttaga gttttttaaaa ggaatgaaat tttgtggatt tattttttgat ttttgattttt 1380 tagaattgta aaataataat tttgtgtttg ttttagttaa tatatttgtg ataatttgta   1440
```

```
atagtagtag taggaaatta aaatattttt taggtttatg atttgagagt ttattaaata   1500
agagatggtt attttttttgg tttttaaatt attttggaaa taaagttatt tttagagagg   1560
aattttaaaa tattgtttgt agttatagta attttaaaat ttgagtgttg tatggtggaa   1620
gtagataatt tattttagga taattgttat ttgttatatt agtttgagga tggtggtgtt   1680
aaagaggagt tatttatttt taggtatatt ttatattaaa tataaattgt ataatttgtt   1740
taaattaagg aattatatta aattatatta tggttattaa attttgtttt gagaaagtga   1800
aattgattta gttttttaaag agataaagag aaagtataag taaattaaat tgtagttata   1860
aaaagaaaga taaaatgttg tagtatattt attgttttgt gtatttaatg aagtttttcg   1920
ttttggttat aaaattagtt ttaaaggttt tttttatatt ttatagtatg aaaaatttaa   1980
aaagtaattt atatgtaaat atttaaatta tgatagaaat ttaaagtaaa aagaaaatga   2040
attaattgaa ttaaaatgtg taggatgttt aaatttattt gataatatat ttatttgata   2100
atatattaat atgaatttag tattttaaaa tgttatataa ataaatgttt ttatattaaa   2160
tattaatgta gttaggattt taagttaata ttattttttt tttttttatat gttttttttt   2220 ttttttttatt aaaaattgtt aaaattattt attttttttt tttttttttg tttttaaata   2280
aataaggttt tttttaagat attgtaggat tataaagtta aattttcggg tttaagttgt   2340
tggtaaaatt ttagagatgt taagttattt atgtattaat tattttttaaa ttttttttta   2400 attttttttat aaaataggag tagggagagg agaaatattt ttgtttaaaa atgaggaatt   2460 gaaaatttttt attataaata aattatatta agtaagttaa agatagtaaa agagtaaaaa   2520
tgttagtaga tattttttaaa atggtaatta tatattattt ttggaatgat tatatgaatg   2580
tggtttatta tttttttaagt tttttatagta aatatatatt tatttgtttt atttagttaa   2640
aaataaatat aatatgtagt tgttttttgaa taattttttt tttttttttt tttttttttt   2700 tttttttcgat aaagttttat tttgttattt aggttggagt gaagtggttt tatttcgttg   2760
tttattataa tttagttttt tcgggtttaa gcgatttttt tgttttaatt tttcgagtag   2820
ttgggattat aggcgtttgt tattattttc ggttatttttt tgtattttta gtagaggcga   2880
ggttttattt gttggttagg ttggtttcga attttcgatt ttaggtgatt tttttcgttt   2940 tgattttttta aagtgaaggg attataaggc gtgaggtatc gcgttcggtc gttttttgaat   3000 aatttcgatt aaaatttata ttcgatattt attttaatat atattataga ttttttattga   3060 taatttttttt tagtaagaaa gataagtttt atttaggtat tgtgaattg gaggttaagt   3120 agttttagta tattttatat tttttttaaga tttttttttt attttaaacg ttcgtaaatt   3180
ttgtatttga taaagagtat attttttattt aatataaata tgttttttttt tttagatttt   3240 tttagtattc gagagatttg tacgcgcgtg gttttttatt ttttttttttt ggttttttaa   3300 gttttttaggg cgtcgttagg aggaggtttg tgattataaa ttttttttga aaattttttta   3360 ggaagttttt tttttttttcg gagaatcgaa gcgttatttg attttaattt ttttgtaaat   3420
ttcgtttttt agagtcgttc gttatttttt gttttcgttg tagatttttt atttatttgg   3480
atcggttttc gatcgtaatt attcggtgcg ttgggtagcg ttttcgtttt tagtagcgtt   3540 cgtattttttt ttattcgatt tcgggtcgcg gtcgtggtta gttagttagt cgaaggtttt   3600
atgttgtttt tcgtcgtcgg ttttatgttg tttttcgtcg ttcgttgttt gtttttttttt   3660 ttttcgtagt cgtcgagcgt acgcggttcg ttttattttt tggtgattag ttagtttttt   3720
tttttttttt tttcggtgtt ggcggaagag tttttttcga ttttgttttt taaatttttt   3780
ggagggatcg cggtattttt ttaggtaagg ggacgtcgtg agcgagtgtt cggaggaggt   3840
```

```
gttattaatt tcgagtattt agcgaatgtg gtattttga agtcgtttta ggttgggttt      3900
ttttcggggg tattagtcgg aagtagtttt cgttagagtt agcgttggta aggaaggagg     3960
attgggtttt ttttatttg tttttatat cgttttcgg ttttttgtt tttagtcgcg        4020 tttttcgtt tgttagtaaa ggcgtgtttg agtgcgttta ttttgttaaa aagaaattcg     4080
ttttcgtttc gttttttttt ttcgcgatat aatttttta attgttaaat tgaatcgggg     4140
tgtttggtgt tatagggaaa gtatggtttt tttttttaat tataagaaaa agtaaaatta    4200 tttttttta gttgtgagag tttatcgag aatcgaaatt atttgtacga ttagaaagtg     4260 ttttttatt tttaattt ttgattttta ggagcgcggg gtttattaag ttagaaattt       4320
tagtttaaag gatttttttt ggagagtcgg attgtttttt tttttttttt tttttttt    4380 tttgcgtgta aaacggttgt ttggggtaag ggtttttag acgtatat tgtttggtat     4440 aagagtagat tttgaaaaga tgaggtttat ttaatacgga cggggagaa ttttgtttgt    4500 aggtagatag gaaatgggg agggagttat tggaaggacg gatttttttt ttaaagttat    4560
aatttttaga ttagaaaaag tgtttagtgt tttagaagta gagttgtata gtgatttaaa   4620
gattagtttt aaatattgtt ttgttttttt tatattttt atattttttt tttttattga    4680
aaatattttg tatttttcgt aattataaag ggggaaggga atatgagtgt tttttgtttt   4740 atagggggttg ttgtgagttt aaatgatgta ttaatatata taagttttaa gaatagtgtt  4800 atatattta agtaatatt tgttagtttt tgaattattc gttttgagga ttggtttgta    4860
attttgtttt gaggtataga aagaaaatgt tttggagtag gacgcggtgg tttatatttg   4920
taattttagt attttgggaa gtcgaggcgg gtagattatt tgaggttagg agttcgaggt   4980
tagtttggtt aaaatggtga tatttcgttt ttattaaaaa tataaaaatt agttggttat   5040
ggtggcgtac gtgtgtaatt ttagttattt aggaggttga ggtaggagaa tcgtttgaat   5100
tcgggaggta gaggttgtag taagtcgaga tcgcgttatt attttttagt ttgggtgata   5160
gaatgagatt tcgatttaaa aaaaaaaaaa aatgttttgg atagaattat tattattata   5220
taaaaggaaa gttcggatgc ggtggtttac gtttataatt ttagtatttt gggaggtcga   5280
gataggcgga ttatttgagg ttaggagttc gagataagtt tgattaatat ggcgaaattt   5340 tgttttatt aaaaaatata aaattagcgg ggtttggtgg cgtatgtttg taattttagt    5400
tattcggagg ttgatgtagg agaatcgttt gaatttagga gaaggcggag gttgtagtga   5460
gtcgagatcg cgttattgta ttttagtttg ggagataaga gcgaaatttg gttttaagaa   5520
aaaaagaaag aaagaaagaa agaaagatta agaagaattt attttttgaa aagattatgg   5580 gtattttta ttatttttat ttataaagaa aagttaaata gtattaaaga gtataataag    5640
cgtaaggagg taaaagtttt aatttt                                        5666
```

<210> SEQ ID NO 13
<211> LENGTH: 2470
<212> TYPE: DNA
<213> ORGANISM: Artificial Sequence
<220> FEATURE:
<223> OTHER INFORMATION: chemically treated genomic DNA (Homo sapiens)

<400> SEQUENCE: 13

```
aaagatgatt aaaagtttaa ttgtttattt gaagagttga ttttttttatt tttgtaataa       60 agggtatttt tagtagtttt tgtttatttt gtttatttgg ttttttttgt ggttgtgtaa     120
ggttataatt tttgtgtttt agtaaatttg tgtatgttta ttttttttt tgttattatt      180
```

```
tttttttttta ttttgtttta ttattttgat gtaaaattat ttgttaattt tatttgaaat        240
gagaaatttt aaggtttata ttatttaaat tttgttagat ttttatttt gttatatggt         300 ttataatgtg ttgggtattt ttagatttgt ttattaaaaa gatgtaaaat aaaataatga        360
ttatttttgt ggattttttt tttatttttg agatgttttt tttggttgta ttattttttt        420
attttttgtt tattgattag aggaggggtt ttaattatgg gtgaatttta tatttttattg       480 aagaggttat gttatatgta tattttttata atataattta tatttatata gtattttttat     540 ttttagtata ttttttttta ttaattttaa taatattatt gtaagttatg ttgaagtaga       600
ttgtaagtgt ttatttataa attgtgaaat gaattaaaat gaaagggtaa agattaaatt       660
atgattaggt ttgaaattaa tatataagat ttaatttttt ttaattaaag attttttgtag     720 gtgattttg tttgtaggat ttttttttt tttagatgt tattggattg tattaggttt         780
attgtagatt ttagttgttg tagaattaat tagatttaag atgagttttt tgattttttt       840
tggtagagtt ttttaattgt tgaattttaa tattgttgtg attagttagt gttataatt        900 gtttgtttta ttttgtgtaa tggatttat attatagagg tatttttta atgttaagat         960 gtttaagtat tgtttaagtg taaattattt aatattttt agttattaag taattaagat        1020
aggtaggatt ttatttgttt taaaatgatt tgatttaaat taaaagagaga atgtggattt      1080 tttgaattt atttggttaa ttttaatata attttagta ttatataatt ttttttaaag        1140
ttttttttat tggttatttt ttgtattttt tttgttttt tttttttt ttagttataa          1200 taattgttag attttgtttt attttttttt gatagtttt attttttaagg ttatttattt       1260 ttttaggta tttttggtt ttagtttgag tatagtagat tttaagatta tatatgttat        1320
agtataggtt attatagtta attttttgaa taaatgtgat tgaattttat gttagtaatt      1380
tttatttatt attttttttat taaaaaggtt taaagttttt atttaatgtt ttttttttatg   1440 tttattttgt taaatgattg tttttttaatg atatttaga attttagaat tattttatta     1500
tggaggatgt gtaagattag tttttttatta aataaaagt gtgaaatgga atatgtaatt     1560
ttattaattt attttggttt taaaattttg tgattattag ataaaatta gaaataaaat      1620 agtattatta atataaataa atttttatta taattatatt ttttaagttt tgtttgtaag      1680
aatgggtaaa atatttttaa aattttgaag aaattattat ttgatagaaa gtttaattta      1740
tttgtgagaa ggtaaatgta tttagatata attaaagttt tttttttttat tttaatttta    1800 tttattttga attaagatt tattgtttta tttttttaga tgttgttatt tgaataatat      1860
tgttttgaga ttaaaaatta gtatattaat ataatttttt ttaaatgttt taagagtttt     1920 gttttttta tttttttt taaaaataag tagttattaa atttttagt agtgaatttt         1980 aaaatttttt ttaattttat aggtttaagg gtagttaagg atggttgtag ttttatatga     2040
ttagttgtta aagtaagttg aggtattgaa gatggagaat ttaaatttt gataagagtt      2100 agaagataat tttaattatt ttataaaatt ggaaattgag gtatttaata tgaaggtatt     2160
aagattgtga ttttaattg tagtttattt attttttattt agtatttttt tttgtaaatt    2220
tgaggtaaga tatttatttt aaaagtgtat tttaaattaa gtaataatat gtaaattttt     2280
ttttgtaaaa gttagtattt atattttaa ataagatata ttgaatttat ttagtgaatt     2340
atataaagaa aataagtgta aaatttttaat ggttagttag tttttagttt ttttttaagat   2400 taaagagaag agattaaata tagtattatt gtattgaggt aaggttttt gtgtagtta       2460 tagaaattag                                                             2470
```

```
<210> SEQ ID NO 14
<211> LENGTH: 2470
<212> TYPE: DNA
<213> ORGANISM: Artificial Sequence
<220> FEATURE:
<223> OTHER INFORMATION: chemically treated genomic DNA (Homo sapiens)

<400> SEQUENCE: 14
ttagttttta tgaattatat agaaaatttt gttttagtat agtgatgtta tatttggttt      60 tttttttta attttaaaaa gaattaagaa ttaattagtt attggagttt tatatttatt     120 tttttatat gatttattga atgaatttaa tatattttat ttaaaaatat aaatgttaat     180
ttttgtaaga aagagtttat atattattgt ttaatttaaa atatattttt aagtaaagtg     240
ttttatttta agtttataag agggaatatt gaataaaaat ggataaatta taattaaaag     300 ttatagttttt gatattttta tattagatgt tttagttttt agttttgtaa gatgattgga     360 attattttttt agttttgtt gaagatttga gtttttatt tttagtgttt taatttgttt     420
taataattga ttatatgaag ttgtagttat ttttggttat ttttggattt ataaggttaa     480 aaaggattttt gaaatttatt attaaaaaat ttagtggttg tttgttttta aagaaagggg     540
taaaggaaat aaaattttta agatgtttaa gaagaattgt gttaatatgt tagttttttgg     600 ttttaaaata atattgttta agtagtagta tttaagagga tgaaatagtg gagttttagt     660
ttaagataaa tgaaattaaa atagaagaga gaattttagt tgtgtttgaa tatatttgtt     720
tttttataga tggattaaat tttttattaa gtaataattt ttttaaggtt ttaaagatat     780
tttatttatt tttataggta aaatttagga aatataatta tgataaaaat ttatttatat     840
tagtaatatt attttattttt tgaattttat ttgatagtta tagaattttta gagttagaat     900 ggattaatga gattatatat tttattttat attttttatt tgataaaagg ttaattttat     960 atattttta tggtgaaata gttttgaagt tttaagatgt tattaaaagg taattatttta    1020 ataaaatgga tatgaaggag agtattaaat gaagatttta agttttttttg ataggaagat    1080 ggtaaataag aattattaat ataaagttta attatattta tttaaaaggt tgattataat    1140
agtttatgtt atggtatatg tggttttggg atttgttgtg tttaaattga ggttaaaaga    1200
tatttaaaga gaatggatga ttttaggagt agagattgtt aaagagaaat gaagtagagt    1260
ttggtagtta ttatgattgg gaaagaagag gagagataaa gaagatataa aagatagtta    1320
ggtaagagga ttttaggaag aattatagaa tgttaggagt tatattaaga ttaattaagt    1380
aagatttagg agatttatat ttttttttta gtttaggtta aattattttg gaataaataa    1440
aattttgttt attttaatta tttaatagtt aaaaagtatt aagtagtttg tatttaagta    1500
atatttaaat attttgatat taaaaaaatg tttttgtaat atgaaattta ttatataaaa    1560
taaggtagat aggttgtaat attggttagt tatgataata ttggagttta gtaattggaa    1620
gattttatta aaggaaatta ggggattat tttagattta gttagtttta taatggttag    1680 aattatatagt aaatttggta taattaatg atatttgagg aggaagggga gttttgtagg    1740
tagggattat ttataaaagt ttttggttga aaaaaattga gttttgtgtg ttaatttag    1800 gtttggttat gatttaattt ttgtttttttt atttaattt atttttataat ttgtaaatga    1860 atatttataa tttgttttaa tataattat agtgatatta ttaggattaa taaaaaaagg    1920
tatgttaaaa ataaaagtat tatgtaaatg taagttatat tatgaaaata tatatgtaat    1980 ataattttttt tagtaagata tagggttttat ttatagttaa gatttttttt ttgattaatg    2040 ggtaagggt gaagaagtaa tgtagttaaa ggagatattt taaaaataaa ggaaaaattt    2100
ataggagtga ttattattttt gttttatatt tttttaataa gtaggtttga aaatatttag    2160
```

```
tatattataa attatatgat agaggtaggg atttgataga atttgaataa tgtgaatttt     2220 aaaattttt attttaaata aaattaatag gtaattttat attaaaataa taaaataaaa     2280
taagagaaaa ggtagtaata gagaaaaaaa tgggtatgta taagtttatt gagatataga     2340
agttataatt ttatataatt ataaaagag ttggatgggt aagatgagta gagattgtta     2400 aaagtattt ttattatagg aataaaaaaa ttaattttt agatgaataa ttaaattttt     2460
aattattttt                                                          2470

<210> SEQ ID NO 15
<211> LENGTH: 2229
<212> TYPE: DNA
<213> ORGANISM: Artificial Sequence
<220> FEATURE:
<223> OTHER INFORMATION: chemically treated genomic DNA (Homo sapiens)

<400> SEQUENCE: 15
tttttttttg gtgttggttg gtgtgggttg gggttaggtg gagaagttgt tttttgttaa       60
ggtgatagaa tgtgttgggg gtgggggttg gggttagggt tggtgtaatt aggggggttgt     120 tgtttttttt tggatatagt ggaagttttt tttgtattat taaattttg ttattttttt      180 tgagggattt gttttaggt agtatgtaag ttgttgtttt gggtttattt tgtattttt        240 tattgggtga ggaaggagta ttttgaatgg agatgggggg gttttggtt tatatatttg       300 tagagaagag gtgtgttggg ttgtattttt ggaggttgtg gtaattgata ttagagaaga      360
ttttggttgt agtgggaag gtttattggt tggaagagg tgttttttt ttttagtaaa        420 gggttttgtt tggaagggtt gttttttatt tgtttagtgg tattatagga tggttggttt      480
ttatttgaat tttttggat ggtattatta tatagttggg ttttgtagt gttggttttt       540 taatttgatg attgttattt tggtgaggat ttgtgttgat ggttggagaa ttttgtgttg     600
tgggtgtata tggttaggtg gtgtttggta ggtgatgttt gggtgtagga tggtgttttt     660
attgttttat tttaaattgt tgtttgggtt taggtttttt ggttttttga ataggggttt    720 gggggttaa ggatgttgag gttttggggg taggaagttt ttttttggtta agtgttttt     780 ttttttttg gtatatattt ttttatttat ttattttgtt tattttggg gtgagaggtt       840 tattaaggta gggtgtgttt ttttatgaa ttatttaag gtttttgagt tgtggggtt         900 ttgggtaatt attttttttt tttttggtt ttaggtattt tagtttaggg gtttgtagag     960
aagtttgaag tttggataaa tgtgttggat gttaataatt ttttatttt ggtagtagta    1020 aaggttaata tattttatt ttttatttta gtttgttatt aaaataaagt tgtgtgtggt     1080
tgagggtagg aaggtgttga gattgagaag aagggatgtt ttggagaaag tgtgtttagt    1140
tgattttaga aattagagtt ttttgggatt tgttgagat ttttttgtagg gtgttttaat    1200 ttgtttttt attgtgtgtt ggtgttgtag tgtgtgtggt ttagggtttg gtgattttgg    1260
tttagtttgg tggttgtggt gaggtttttg gtgtagttgt ttggaatttt gtattagaat    1320
tgggattgtg taaatgtttt ggttgaagtg ttattttatt taagaaatat tgttgttagg    1380
aataaaatgg ggttttttgg gttttttgaagt attttttgaa atttttttaa aataatttat   1440
aaaaaatgtt tttgttttaa tgtttttataa tgtttaagga aatatgtaaa tggtttgttt   1500
ttttattgag atggttgttt taattaatag tgtatatata tataataatt ttttaatttt    1560
ttttttttag agttaagtat tttattatat gtaaattata ataagaaaa gattgtgtaa     1620 gattatgtaa gttgattgat ttaaaatatt gagtttaat ttaggttttt tgtttttta      1680 tttaataatt tttgtgtttg gattagattg gtgaagtagg ttatggaaat taataaagta    1740
```

-continued

```
aaaaattaaa agtatttttt tttgttattt tttttttttaa aattaaataa tagttgtttt      1800
tttttgagta ggttttagtt ttaggtttga gttttttttgt gattattttta tagttatttta    1860 tagtagttgt tgttgttttt gttgggtttt tgtttttgtt tttttttgggt tgtttttttgt     1920 atataaaata tattttagtt ttttaattaa atttaaatat gattttggta gaatttatat       1980
attttgtggt gtatggattg tgttggtgta ggggaaataa atatttttttg gtatttaatt      2040 attgagttta atttgaaaaa ttgggattgg gttttttaggt ggtatttttag gggttttaat    2100 ttggtttgtg ttttttttaga ttttggtgtt gagagtgttg tttttgtggg tgggtggatg      2160
gagaggtaat aatttgtttt taataaaaat ttgttgttat tgaattgaaa gtgaaaggga       2220
agggagaag                                                               2229

<210> SEQ ID NO 16
<211> LENGTH: 2229
<212> TYPE: DNA
<213> ORGANISM: Artificial Sequence
<220> FEATURE:
<223> OTHER INFORMATION: chemically treated genomic DNA (Homo sapiens)

<400> SEQUENCE: 16
tttttttttt tttttttgtt tttgatttgg tggtgatagg ttttttgttga aagtagattg        60 ttatttttttt gtttatttat ttgtaaaagt agtgtttttta gtgttaaggt ttggggaggt      120
gtgggttagg ttggagtttt tggggtgttg tttagggggtt tagttttgat tttttgaatt      180
agatttagtg gttaaatatt agagggtatt tatttttttt gtattgatat aatttatgta       240
ttatgaaatg tgtaaatttt gttggggttg tatttgaatt tagttagaga attggggtgt       300
gttttgtata taagagatga tttaaagaag gtagaaatga aaatttgata gaagtagtaa       360
tagttgttgt gggtgattgt ggggtgattg taggaaaaatt tgagtttggg attgaagttt      420
gtttaggaag gggtgattgt tgtttaatttt tggagggagg gatggtgaag gaagatgtttt    480 ttaattttttt attttgttaa tttttatagt ttgttttatt agtttggttt aaatataaaa      540
gttgttaaat agaaaaatag agggtttgga ttaaaattta atattttaag ttaattgatt       600
tgtatgattt tgtataatttt tttttttatt ataatttata tatagtgaag tgtttagttt      660
tgaggaggaa agttggaaga attgttatgt atgtgtatat tgttagttag gatgattatt      720
ttgataaaga aatagattat ttatatgttt ttttaaatgt tgtaaaatgt taaagtaaaa       780 atatttttttg taagttgttt taagaaaatt ttagaagata ttttggagta ttggggatttt    840 tatttttgttt ttgatagtag tgttttttttga ataggggtgat atttttagtta gggtatttgt 900 gtggttttga ttttaatgtg aagttttaag tggttgtgtt aggaattttg ttgtgattgt      960
tgggttaagt tggagttatt aagttttgag ttgtatgtgt tgtgatgttg gtatgtagta      1020
ggaaaataga ttaaaatgtt ttatagaaaa ttttggtgaa gttttggagg attttggttt      1080
ttaagattag ttgggtgtat ttttttttggg atgtttttttt tttttggttt tagtgttttt    1140 ttgttttttag ttgtgtgtag ttttgttttg gtggtaaatt gaaataagaa atggaaatat    1200
attggttttt gttgttgtta gggatgagag gttgttgatg ttttggtgtgt tgtttgggt     1260 tttgggtttt tttgtagatt tttggattgg ggtgtttgag gttaggagag gaggggggata   1320 gttgtttgga gttttttgtgg tttagaggtt ttgggatgat ttatgggggg ggtgtgttttt  1380 gttttggtga gttttttgtt ttgagggtag gtgaggtggg tgggtagggg agtgtatgtt    1440
ggagagaaga gagaatgttt aattagagag aattttttgt ttttgagtt ttagtgttttt      1500 tagttttttta aattttttgtt taggaagttg aaggattttag gtttaggtaa tggtttgggg 1560
```

```
tggggtggta agagtgttgt tttgtatttg gatgttgttt gttaggtgtt atttggttat    1620
gtgtgtttgt agtgtagggt tttttggtta ttagtatagg tttttattga ggtgatagtt    1680
attggattgg gaaattaata ttgtgaggat ttggttatgt gatgatattg tttggggaa     1740 tttgagtgga agttgattgt tttgtggtgt tattagatag gtgagaagta gttttttaa     1800 atagggtttt ttgttggaag gaggaggtat ttttttttag ttagtgagtt tttttagttg    1860
taattggggt tttttttaat attagttatt gtggttttta gaggtgtagt ttggtatatt    1920
ttttttttgt agatgtataa attggggata tttttatttt tatttaagat gttttttttt    1980
tatttagtag aggggtgtgg agtaaatttg ggataataat ttgtgtgttg tttggaagta    2040 ggtttttag aaaggatgat aaaaatttgg tgatgtggaa gaagttttta ttgtgtttag     2100
gaaagggtag tggttttta gttgtattgg ttttggtttt ggtttttatt tttagtatgt     2160
tttgttattt taataaagag tggtttttt atttgatttt aatttgtatt agttagtgtt    2220
gaggaaaga                                                             2229

<210> SEQ ID NO 17
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 17 gttttggtg agatatgtgt tttataagtt ttaatggaga aaaatgtaag tattttattt      60
tttgaaattt ggttatttga gtaatgagaa aatagttatt tttttagga tagtggtttt     120 taattatggt tatgtgtttt tttaggaaaa ttttaaaaat atatatatat taatgttttt    180
gtgttatttt tagggatttt aagttttga atatgaattt tgtattagta ttttttaatt    240
atttaggtga ttgtgatgtg aaattatgat tgagttttat tgttttaaga tgaaataaat    300 ttttttagt attgaaatta taaatttaaa ttattaaaat taattaaggg tatgggaatt     360
aataaggtat agggaagttt ttatattata aaattttttt ttaaattat agtttattgt    420 ttatatgtta tttgttattg tagaaaaggg tgaaaaaata gtaaatttaa ttattttag    480 tttgaaaaat tatttagaaa tgaagatgat gattttgaaa tattgttaat attatttgat    540
ttataaataa tgttttaata tatttattat atattgatag atatttttt atatgaatat    600 tatatattaa aattaaggta ataatgtatt tagaatattt tatttatatt tatgtatttt    660
aagtaggtta gaaattaaga tatgagttat taagtatgag atgttaaggt gtggggttag    720
aaattatatt gtattttatt attaataatt aatatatatt ttaatattat atatatttaa    780
ttttaatttg tatattttta attattttta attatgtgta taaatataag tatatatatt    840
tttatgtatt tatttattta tattttatt tatttattta tatagggat tttttttaaat    900 ttattattat taaattatat attttatttt taatttttag aataagttta ggaggtaggt    960
attgttatta tttatatttt ataaatgagg aaattgttta tagttataaa gttattgtgt    1020
tagatatatt agaagtttaa tatatatttg gtgaatatat gtataaaaat agagagatag    1080
atatgtataa tagtttattt ttatattgag taaaagtttt taatttgttt tagaaatttt    1140
tttgtgaaaa ttgagtaaaa attgaggtat tttttatttt gttatatagg tataggtggt    1200
atttattttt tttaataagg atgaatattg aaatgtggat tttaaggttt aattttagat    1260
tttttgaatt tttgatagtg ggatttggaa tttgttattt gttttaaagt tttttaagga    1320
atttatatga ttaattaggt ttagaaatta ttggatttta ttgttgaagt ttgagaatta    1380
```

```
aagtttgggt tttattgtgg ttttatagaa agggtaaatg aagtattatg gatagaattg    1440
atatgttttt agttagtttt tttttttaga agttaatagg tagtaatata gtagaaatta    1500
gtgatttatg ttttgtgttt tgaagttagg tagaaatttta tagagttttta gtagtgttat  1560 tgatgagatt tgttttttgg ggtaagttgt ttgatgtttt taaagttata tttttttttat   1620 ataaaatgag ataatatttt tgtttttata ggggtgtttt aaagattaaa taaaaataat    1680 atgtttatt ttatatggta taatgtttga tatttaagaa gtaaaggata tattttattt     1740
ttattgaagt aattagaaag tatgaaatta tgaaggagat aagagttttg attggtagtg    1800
tatttatttt ttttaggttt atttatttat tttaaattat ttttgttgga gaataatttt    1860 taagttttttt atttaagttg tgagtaattt tatattttat aatgatgttt tttttatgag   1920
aaaaaaaaat gttttaaagt ttttttggaga aaatatattt gtattatttt tattgaaaaa   1980
tttaataatt ggattttgtt tttttgtatt aatttttagag tgtatatgtt ataaataaag   2040
tgttttagtt taagaagatt gaaagtaaat atggtatagt atttttaaaat aagaatttttg  2100 taaatatatg gtatgattgt gttatattat tagtaattat atgatatgta atgtaaagta    2160
tagtttatag atttaaattt aatttttaata agtaaattga ttttgttttg ttggggaaaa   2220
gttaaagtat taatttaatt gttaatgtag ttttgtttat tttttttggta tttagtgata   2280 agtttaaata atgtatatat ttttatttat atatttagta atataatttt tgtttaatg     2340 agtgatgttt ttttgttatt tggtggtgtt tgttagtttt agaatttgtt ttttggtggt    2400
attataatat taagtataga gtaagtgtaa taaaattgta gtattttat tgaaaaggtt     2460 ttgttttaaa ttgtttaata atttaaagga ttttttgtgga agtaattgta tttgttaatt   2520
agttataatt agtaattaat tttttggag ttttaatttta ttttttggtaa aatgttttag   2580 gaagagtata tattattaga aagtatgtta aaaatttatt tagtagaaaa tttaaaaata    2640 gtttttttt gttaagaggt tttttaaaat tttatttata tagttaaatt tgaaattttt     2700
agtaggtttt gttttattat tataattatt gtataaatat ttttaaggat tttgttttta    2760
gttttaagta tgatttatttt ttataagttt gattagttat tatattagtt ttgttatgga   2820
aaatgatatg ttttttatttt ttgttgtaga gttgttaaat tttgatttat atttatgttg   2880 tttttttttgt tgaaagtttg tagtgaaaga aattttttaat ttttttgtttt gtaatattag 2940 ttggtagttt tatttaatgg gtattttgtt tttttaaaga atttagttgt tttgtttaga    3000
agttgatttt ttgatgtttt taatgtttgg tttaattgat ttgttttaat ggagttttg     3060 ttggtgagga gtgagatgtt attgattaga atgttgggat ttgttgttta attgttagga    3120
gtgagagata ttgagattta gaaattttttg gaggtgggag gggagaggga tagttttgga   3180
tggaggtgga gatgtaagat aaagggatgg atttatata ggaaaaaaaa aaagatttttg    3240 ttgaggtatt gaggtgttgt atgattatat tttttaaagg agaagttaaa aagtaaggaa    3300
gtgggaggag gttggaggtt aaagtattta aaaggattat ttgggtataa tttgttttttt   3360 tgttggtgtt tgtaaaggat agatagttttt gttttttaaag tatatgaatg ttttttttaa  3420
gtgattggga atggatatta attgtttgtt aaatgttatt aaatgttttt ttaaatttag    3480
gggatataga aagagggta taaaaggaga atttaaatag aaaaagggag gatttggagg     3540
tttttgaaag tgggggggaga agaaggagga gggataatag agaggaatag agaaggagag   3600
tggagagaag ataaataaaa ataaaaatag gaattattga ataattatat attaaaagga    3660
aagttttttt ttatggggta tttaaaatat tgagattgta atagtgattt tggttatgga    3720
agaaagatgt tttttttttat ttttgttttt gaaagttttt ggtttttgtta ttggtgatta  3780
```

```
aaatttttatt aggttaaaga gtgtgtttaa ttgtttgaag aatgtagtag atggaaggtg    3840
ggttttgtta tgttgtttgt ttttttttgtt ggagagaatg aaagaaatgt gtagagttag   3900 agattttttgt tgagttagat tttttttttgt tgttttaggt tattggttat ttggtaaaga  3960
tttgagtaag gaatgtaggg ttattgtttg ggttaataaa tggagtttgt ttttttttttt  4020 ttggatgttg ttgtttggtt gatgttttttg gtaatttatt tgtggtgtat gtagaggagt  4080
tttttttttt tttttagatt attttgtttg attaatttga tttttttaaat atatttgatt  4140 gtatttttta ggtggatata ttaataggtt atgggttgga gaggagtggg tgatgaggag    4200
agggatttaa atttgtgaat gtttgggttg ggttggagtt gtgggggtt tgggaggaga    4260 gaggggagaa gagagaagga aggagagtgt ttgttgggat ggttgagttg ttttggtgag    4320
tagttttggg gttgtatgtt tttgtgggag atgttgttgt tgttttttagg ttggtaagag  4380 tggttttaat attattgttt tttatttttt tttttgtaaa tttttagaga aatgttttttg   4440 gttttttttgt tgtgatattt ttagtttgta ttttttttata gttaggtgg tgtgtttttg   4500 tatgttggag tgttggttgt tagtaggatg tttttttttg tgttgatttg ttttttttttg  4560 ttttgttgtt gttgtttttt tgatattttt gttttttatta ttttttagttt ggagagatgt  4620 tatttagttg tggtttgtat ttgtggtttg gggttatgtg tggaagaggg gtgttagttt    4680
ggattttgtt tttggtaggg ggtgttttgg agtggagagt gaggtgaatg gtatatgagt    4740
gtgtgggtag tttattttga agtttgagtt ttttatttga gttatgtttt gtttagttttt   4800 atttgggtta gtgtttggtg agtgagttta tttgtggttt ttgtggttgt ttttttttttg   4860 tatttttgta tttatttgtt gatttttttt ttttgggatt tgtattttgt tttattaatt    4920
agagtttgat tgtttttttt tatgtgattt tgggtgggtt gaggatttgt tgttttttaa    4980
atgttagagg gatgtgggtg gtagagtttg agaggtggtt gttgggttgt ggggtgtttt    5040
gatttttttt ttatttttgtt tttttggggtt ttatttgttt gttttttggat ttttgttttt  5100 ttttgttttt tggtttttta gagttttttt tttatggtag tagttttttg tgttttttggt   5160 gtagttttttt agtggatgat ttttttttgttt tggggttgag tttagttttt ggatgttgtt  5220 gaaattttttg agattatgtg tgggtttggt tgttgttttt ttgttgggtg ttattgttat    5280
tgttgttgtt tttgttgttg ttgtttgtgg gatgtttagt agtttgttgt ttggttttttg   5340 tgattttgtg ttttttggaa gttgtttgtt gttgtagagt tgtatgaatt agttatggtg    5400
ttgtgggagt ttttgtggta gtgtagtagt tggatatttt gtgagggttt ttgttggttg    5460
ttgttgttgt ttgttatgtt atttattgta gtttgtttgg tgaagtttgt tgtttttttt    5520 attttttttaa gtgattgtta aatgtttatt ggttggaatt gttttggtaa gtttagaatt   5580 tttgttttttg atttttttaat tttgtagaag aatatgtgta tttagtatag attagtttat  5640
tttagtgtgt tttttttagtt ttttatttttt tattgttttta gattttttaat attatttatt 5700 tttatttaga gaaataaggg gaattgttgt aggtttgggg gtgagggggtg gttttgggat   5760 gggtagaaag tgtaggtgta gtaggaaatt tttgtatgtt tgtgtttata ttggagttgt    5820
gaggattttg agaaatatta aatgggatgg tttttttgggt ttattgtttt gaaagagtat   5880 taatttttagg ggaaatattg aaatagaagt tttgttatta ttaaagaaaa aagttttatt   5940
aggatgagga agaaataatt ttatgagaaa gaatgagtga gaaagtaata aattaaatgg    6000
tgattgtagg ggaattgttg attttttggta aaggtgttat gaggttgtat tggttttttg   6060
ttgaagatta ggttatatag attttagagg agtttgggtttt taatagaatt tttttttttt  6120
tttttttttt tttttttttt tttttttttt tttttttatt tatttatttt tttttttttt    6180
```

```
ttatttttt  ttttttagg    tggtaaaaga  tattggtttt  gtagtttaga  tatgttttt    6240 tttttgtttt  tttaagtttt  aaggtagtat  aggggagttg  agaaaaagaa  tattttgtgg   6300 gtttttagg   ttggagtggg  tatgattgag  gttggttagg  ttttatgtag  gtgagttgag   6360
ggtggaattg  attttagtgg  gtgttgattt  ttttattttt  ggataggttt  ttgtggagtg   6420
ggttaggtat  tttttttgtt  tgtttgggtt  ttttagatt   ttgatggtga  atgtttggta   6480
ggttttgttt  tgttgaagtt  ttttaattaa  atagggttag  aggatgggag  ttgttgtatt   6540
tttagttggt  atagtatttg  gtttgatagt  ttgtagtata  gggtgtatgt  aattttttat   6600
tttttgtgaa  tataatttg   ttgtagttaa  atttggtttt  gaataaagtg  ttttttaaag   6660
atgtatataa  gttgaagtgt  atgtaattt   agagaggagg  gaatgattaa  ttgtaattta   6720
gggtgaaagt  ttgtatagtt  tttagttatt  attgatgtaa  atgttaaaag  gaaaattatt   6780
atgtattatt  ttaatttatt  ttttataaag  ataagttgag  atatgtaatt  ttattagatt   6840
tgggttaata  gattgttttt  tttttggta   gttttaaat   ttggtattt   aataaaattt   6900 aatatgtttt  tataatttt   tgatttatgt  gtatatgtgt  gttgttttg   aaagaataag   6960 ttttatttg   ttattgttta  attatttttt  agatgtttta  ttatggtaat  aattatgagt   7020
ttgtaaaaat  aattttgga   aatgttgatg  gttttgtagt  ttaatataga  ttggtttgtt   7080 ttattttag   ttttgtatt   gttttaggaa  ataattaatt  taaatgtgaa  gttgatattt   7140
gtaattaaga  aattatatat  ttattagata  ttttaaaggg  gattgtataa  attaaagaga   7200
ataaattggt  tttgtagata  ggttgttaag  aatttggtat  tttgtttta   ttttgttaa   7260 tttagaggtg  attaatttt   atttgagtta  aatagattat  tatagaaaat  attgtgtttg   7320
tttattttta  ttattgaggt  tttgtttttt  ttttgtttgg  atatattta   aataagggt    7380 tgttttagtt  gttgaagtaa  aagaataatt  aaagatgggg  aaatggtaaa  agggtattta   7440
gagattatta  ttagttttttt tttaaaatgt  ggagttttgt  ggttataaat  attgtttatt   7500
taatgagtaa  aaaataaaaa  taaaaaaaaa  ataggaagta  aatgttaagt  ttttatttat   7560
tattgttagt  attaatgtaa  gttttaaaaa  atagtattat  tagaaaagga  tattaaagga   7620
gaattgatta  gaaaagaatt  gtggaaaatg  gaaatgaata  ttgattattt  aattagattt   7680
tgaggttatt  agtagatagt  gattttgtag  tatagttata  gttgttggat  ttaaaattta   7740
ggataagtat  tttaaagttt  taaagtagtg  tttttttttg  ttaaaatttt  gtaagatgtt   7800
ttaatgattg  gagtgttttt  tttgaatttg  agg                                  7833
```

<210> SEQ ID NO 18
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 18

```
ttttaaattt  aaagagaata  ttttagttat  taaaatattt  tatagatttt  taataaaaaa    60
aagtattatt  ttgaagtttt  aaaatatttg  ttttaaattt  taaatttaat  aattatagtt   120
gtattgtaag  gttattgttt  attgataatt  ttaaaattta  gttaagtgat  taatatttgt   180
ttttattttt  tataatttt   ttttagttaa  tttttttta   gtattttttt  ttgatagtgt   240 tatttttaa   agtttgtgtt  aatattgata  gtggtgaatg  aaagtttaat  atttgttttt   300
tgtttttttt  ttatttttat  tttttgttta  ttaggtggaa  aatatttatg  attataaaat   360
tttatatttt  ggaaaagagt  tagtgatgat  ttttgaatat  ttttttatta  ttttttatt    420
```

```
tttaattgtt tttttgtttt aatgattgaa ataatttttt atttgaaatg tatttagata      480
aagaggaaat aaagttttaa taataaagat aaataggtat agtgtttttt gtgatggttt      540
gtttggttta aatgaagatt gattatttt aagttaatag gggtggaagt ggggtgttaa       600 gttttgata  atttatttgt aaaattagtt tattttttt  agtttatgta gtttttttta      660
aaatatttgg taaatatgta attttttgat tgtaaatgtt aatttatat  ttaagttagt      720 tatttttaa  aataatgtaa gggttaggaa tgaagtaaat tagtttgtgt tggattataa      780
agttattaat attttaaaa  attgttttg  taggtttata attattatta  taataaagta      840
tttaaaaagt gattaggtaa tagtaaagtg aaatttattt ttttaaaaat aatatatatg      900
tatgtatgaa ttaagaagtt atagaaatat gttgagtttt attaaaatgt taaatttaga      960
aattgttaaa aaagagaata atttattgat ttaaatttaa tagggttgta tattttaatt     1020 tgttttgta  aaggataaat tagaatgatg tataataatt ttttttttgg tatttatatt     1080
agtaataatt aggaattata taggtttta  ttttgagtta tagttggtta ttttttttt      1140 tttaaagtta tatatatttt agtttatata tattttgaa  agatatttta tttagagtta     1200
gatttaatta tagtaaaatt atatttatag aagatgaaaa attatatata ttttatatta     1260
taggttgtta aattgaatgt tatgttagtt aggagtgtag taattttat  ttttggttt      1320 tatttaatta ggaagtttta gtagagtgaa gtttgttaag tgtttgttgt tagaatttga     1380
aggaatttga gtgagtaaga agagtgtttg atttatttta tagaagtttg tttagaaatg     1440
gaggagttag tgtttattga agttggtttt gttttggtt  tgtttatatg gagtttgatt     1500
agttttagtt atgtttattt tggtttggga gatttgtaaa gtgttttttt ttttaatttt     1560
tttgtattat tttgaagttt agggaagtaa agagaggggt atatttggat tgtaaaatta     1620
atgttttttg ttgtttagga gagaagggaa tgagagagag agagagatag atagatagag     1680
agagagagag agagagagag agagagagag agagagagag agaaatttta ttgaaattta     1740
gtttttttag aatttgtgtg atttggtttt taatgggaga ttagtgtgat tttatggtat     1800
ttttgttagg aattagtgat tttttgtag  ttattatttg atttattgtt tttttgttta     1860 tttttttta  taaagttatt ttttttttat tttagtaaga ttttttttt  taatgatgat     1920 aaagttttg  ttttagtgtt tttttagga ttggtgtttt tttaaaatag tgaatttaga      1980
aaattatttt gtttaatatt tttaaaatt tttgtagttt taatgtaagt gtaagtatgt      2040
aaaggttttt tgttatattt gtattttttg tttattttag aattatttt tatttttggg      2100 tttgtaatag ttttttttgt tttttggat  agaggtgggt ggtattaggg gtttagggta     2160
gtaggaggtg aggggttgag gaggtgtgtt agggtaggtt ggtttgtgtt ggatatgtgt     2220 gttttttgt  ggagttaaag ggttgggat  ggggtttg   gatttattag agtaatttta     2280
gttggtgggt gtttggtagt tatttaagga ggtagggaaa gtagtgagtt ttattgggtg     2340
ggttatgatg agtagtatga tgggtagtag tagtagttag taaaagttttt tgtaaagtgt     2400 ttagttgttg tattgttgtg gggatttta  tagtattatg attagtttgt gtaatttgt      2460 agtagtaaat ggttttgag  gaatataggg ttgtgggggt tgggtagtgg gttattgagt     2520
attttgtgga tggtggtagt agaggtggtg gtggtgtag  tggtatttgg tggggaagta     2580
gtagttaaat ttgtgtatga ttttgagagt tttagtaata tttagggatt gggtttagtt     2640
ttggagtgag agggttgttt gttgagaagt tgtgttggag atgtgggaag ttgttgttat     2700
aaggagggag ttttgggaag ttggaggata ggagagatg  ggagtttagg ggtagatgag     2760
tggagtttga ggaggtaggg tggagggaga gttaaggtgt tttgtagttt ggtagttgtt     2820
```

```
ttttgagttt tgttgtttgt attttttttgg tgtttgggaa gtagtaggtt tttagtttgt    2880
ttggggttat gtgggaagag gtagttgggt tttgattggt ggagtaggat gtaggttttg    2940
ggagggaggg gttgatgagt aggtgtaagg atgtaaggag gaggtggttg tggaagttat    3000
agatgggttt gtttgttagg tgttggtttg agtggggtta ggtggggtat ggtttaaatg    3060
agaagtttgg gttttagggt gggttatttg tatatttata tattatttgt tttattttt     3120 gttttaggat gtttttttatt gaaggtgggg tttggattag tgtttttttt ttgtgtgtga   3180 ttttggggttg tgagtgtggg ttgtggttgg gtggtgtttt tttgagttgg agatggtggg   3240
ggtggaggtg ttagaggagt agtagtagta gggtagagag gggtgagttg gtgtgggaga   3300
gggtgttttg ttggtgattg gtgttttagt gtgtgggagt gtgttgttta ggttgtaggg   3360
ggatgtaggt tgggaatgtt gtggtggaga ggttagggat gttttttttag ggatttatag  3420 gaaagagggt gagaggtgat ggtgttagaa ttgttttttgt tgatttggaa gtaatagtag  3480
tattttttat aagagtgtgt aattttaagg ttgtttgttg aggtagttta gttatttttgg  3540 taggtgtttt tttttttttt tttttttttt tttttttttt ttaggttttt tgtagttttg   3600
atttagttta agtgtttgta ggtttgaatt ttttttttta ttatttgttt tttttttagtt  3660 tgtagtttat tagtgtgttt atttgggagg tgtggttaga tgtgtttgga aggttagatt  3720
ggttgggata agtggtttga gagaaagaga aaggttttttt tgtatatgtt gtgggtgggt 3780
tgttgggagt attggttggg tagtggtgtt tgggaagggg agagtgggtt ttatttgttg  3840
gtttaggtag tgattttgtg ttttttattt gggttttgt tggatggttg gtgatttggg  3900
gtgatgagag aaggtttaat ttggtaggag ttttttggttt tgtgtgtttt tttttattttt 3960 tttagtggga agggtaaatg gtatagtggg atttgttttt tgtttgttgt attttttagg  4020
tagttagata tatttttttag tttaatggaa ttttagttgt tagtaatggg attaagagtt  4080
tttggggata agggtggaga ggaatatttt tttttttatga ttggggttat tattgtagtt  4140
ttagtgtttt ggatgtttta tagggaagag tttttttttt ggtgtgtgat tatttagtga  4200 tttttgttttt tgttttttgtt tatttttttt ttgtttttttt tttttatttt tttttgttat 4260
tttttttttt tttttttttt ttgttttttaa aagtttttgg atttttttttt tttttatttta 4320 aattttttttt ttgtgtttttt ttttttgtgt ttttttgaatt taggagagta tttgataata   4380
tttaataggt aattagtgtt tattttttaat tatttaaaag aggtatttat atatttttgaa    4440 aatgggatta tttattttttt gtagatatta gtagaaaaat aaattgtatt tgagtaattt     4500
ttttaagtat tttaattttt aattttttttt tattttttttg tttttttaatt tttttttttga  4560 gagatgtgat tgtgtagtat tttagtgttt taatgaaatt tttttttttt ttttgtgtga    4620
aatttatttt ttttatttttat attttttgttt ttgtttgaga ttgttttttt ttttttttat  4680
ttttaaagat ttttgaattt tagtgtttttt tatttttggt aattaagtag tagatttttag  4740 tatttttagtt ggtggtattt tgttttttat tgatgaagat tttattaaaa tagattaatt   4800
agattagatg ttggaggtat tagaaaattg gttttttgat agagtagtta aatttttttaa   4860 ggaaatagaa tatttattag atagagttgt taattaatat tgtaaaataa ggaattagaa    4920
attttttttg ttataggttt ttagtagaga aggtaatata aatatagatt aagatttaat    4980
aattttatag tagagaatga gaatatgtta ttttttatag taaggttggt gtggtaatta    5040
attaggttta tgaaaataag ttatgtttga aattaaaggt aaagttttta aaagtgttta    5100
tgtagtaatt atgataatga aataggattt gttaggattt tagagtttgg ttatgtaagt    5160
agaattttag agaattttttt agtagaggaa aattgttttttt gaattttttg ttaagtaaat  5220
```

```
ttttggtata ttttttaata atatatgttt tttttaagat gttttgttaa aagtaagtta    5280
aaattttaaa ggagttaatt attggttgta attggttaat aaatgtggtt gtttttatag    5340
aggtttttta aattattaaa tagtttgaag taaagttttt ttaatgggaa tgttgtaatt    5400
ttgttgtatt tattttgtat ttagtgttat agtgttatta agaaataaat tttgaaattg    5460
gtaagtatta ttaagtggta gaagaatatt atttattgag tagagaattg tattattgaa    5520
tatgtaaata aaaatatata tattatttag atttgttatt aggtattaaa gaagtagata    5580
agattgtatt agtaattgga ttagtgtttt aattttttt tagtaaggta aaattagttt    5640
atttattaga attaaattta agtttatgaa ttgtattttg tattgtgtat tatatgattg    5700
ttagtaatat gatataatta tattatgtat ttgtaaaatt tttattttaa aatattatat    5760
tatatttatt tttaattttt ttgagttaga atatttatt tgtggtatat atattttaga    5820
attgatgtag aggagtagag tttagttgtt agattttta gtagaaatag tgtagatata    5880
ttttttttag aaaatttaag aatatttttt tttttatgg aaagaatatt attataaagt    5940
gtgagattat ttatagttta agtagggggt ttgggagtta ttttttaata agaatagttt    6000
aagataaata aatgaatttg ggaaaataag atatattgtt aattagaatt tttattttt     6060 ttatgatttt atatttttg attgtttaa taaaggtaag atgtattttt tgtttttag      6120 gtgttaggta ttgtgttatg taggatagaa tatgttattt ttatttaatt tttaaaatat    6180
ttttatgaga taaagaatat tattttattt tatataaaag gaatatggtt ttgaaagtat    6240 taggtaatttt gttttaagaa ataaattttg ttagtgatat tgttgggatt ttgtgaaatt    6300
ttgtttgatt ttagagtata agatataagt tattaattttt tgttgtattg ttgtttgtta    6360
gtttttgaga ggggaaatta attgggaatg tattagtttt gtttatgata ttttatttgt    6420 ttttttgtg gagttgtagt aaggtttaaa ttttaatttt taaattttgg taataagatt     6480
tagtgatttt tgaatttggt tgattatatg aattttttga gaaattttga ataatagat     6540 aaattttaag ttttattatt agggattag aaaattgga gttgggtttt gggatttata      6600
ttttaatatt tattttgtt ggagaagtaa ggtattattt atatttatat gataaatgaa     6660
aggatatttt gattttgtt tagttttat agagaggttt ttgagatagg ttaaaagttt      6720
ttatttagtg taaagatgag ttgttgtata tgtttgttttt tttgttttta tgtatatgtt    6780
tattaaatat gtattaagtt tttaatatgt ttgatatagt aatttttgtga ttgtagataa    6840 tttttttatt tgtaaaatgt gagtaataat aatatttgtt ttttgggttt gttttaaaga    6900
ttaaaataaa aatgtatggt ttaatggtag tggatttggg gggattttt atataaataa     6960 gtgaatggag gtatgaataa ataaatatat aaagatgtgt gtatttatat ttatatatat    7020
aattaaaaat agttaaagat gtataaatta aagttaaatg tatgtgatat tgaagtatat    7080
gttgattatt gataatgaag tatagtataa ttttaatttt tatattttaa tatttttatat   7140 ttaataatttt atattttaat ttttagttta tttaagatat atagatatag atagaatgtt   7200
ttaaatgtat tattgttta gttttaatgt ataatattta tatgaaaaag tatttattag    7260
tgtgtagtaa atgtattaga atattattta taggttaaat gatattgata atgttttaga    7320
gttgttattt ttattttgg ataattttt aaattgagag taattaaatt tgttatttt       7380 ttattttttt ttataatggt aaataatata taaataatga gttgtgattt aaagaaataa    7440
ttttataatg taaaagtttt tttatgtttt attgattttt atgttttaa ttaatttgg      7500 tagtttaagt ttgtgatttt agtgttgagg aaagtttatt ttattttaga gtagtggggt    7560
ttagttatga ttttatatta taattatttg gataattaaa gaatattgat gtagagtttg    7620
```

-continued

| | |
|---|---|
| tatttaaaga tttggaattt ttagaagtga tatagaagta ttggtatata tatatttta | 7680 |
| aagtttttt ggagaaatat atagttatga ttgagaatta ttgttttggg gaaagtgatt | 7740 |
| attttttat tatttaaata gttaagtttt aggaggtaaa atatttatat ttttttttat | 7800 |
| taaaattgt aaaatatata tttattaaa gat | 7833 |

<210> SEQ ID NO 19
<211> LENGTH: 5666
<212> TYPE: DNA
<213> ORGANISM: Artificial Sequence
<220> FEATURE:
<223> OTHER INFORMATION: chemically treated genomic DNA (Homo sapiens)

<400> SEQUENCE: 19

| | |
|---|---|
| aaaattagaa tttttatttt tttgtgtttg ttatattttt tagtgttgtt taattttttt | 60 |
| ttgtaagtga gggtggtgga gggtgtttat aatttttta gggagtaagt ttttttggt | 120 |
| ttttttttt tttttttttt ttttttttt tgagattaag ttttgttttt gttttttagg | 180 |
| ttggagtgta atggtgtgat tttggtttat tgtaattttt gttttttttt gggtttaagt | 240 |
| gatttttta tattagtttt tgagtagttg ggattatagg tatgtgttat taagtttgt | 300 |
| taatttgta ttttagta gagatagggt tttgttatgt tggttaggtt tgttttgaat | 360 |
| ttttggtttt aggtgatttg tttgttttgg tttttagaa tgttgggatt atagatgtga | 420 |
| gttattgtat ttggattttt ttttatgta atagtgataa tttatttaa agtatttttt | 480 |
| ttttttttg agtggagtt ttatttttgtt atttaggttg gagggtggtg gtgtgatttt | 540 |
| ggtttattgt aatttttgtt ttttgggttt aagtgatttt tttgttttag ttttttgagt | 600 |
| agttggaatt atatatgtgt gttattatgg ttagttaatt tttgtattt tagtagagat | 660 |
| ggggtgttat tattttggtt aagttggttt tgaattttg atttaggtg atttgtttgt | 720 |
| tttggttttt taaagtgttg ggattatagg tgtgagttat tgtgttttgt tttaaagtat | 780 |
| tttttttta tgtttaaaa taagattgta agttagtttt taaagtggat aatttaagag | 840 |
| ttaataggta ttagtttagg atgtgtggta ttgttttaa ggtttatatg tattaatata | 900 |
| ttatttaaat ttataataat ttttataaag taggggtat ttattttt tttttttttt | 960 |
| ataattatga aaatgtaag gtattttag taggaaagag aaatgtgaga agtgtgaagg | 1020 |
| agataggata gtatttgaag ttggttttg gattattgtg taattttgtt tttagaatat | 1080 |
| tgagtatttt ttttggttta ggaattatga ttttgagaat ggagtttgtt tttttaatga | 1140 |
| tttttttttt atttttttat ttgttatag gtagaatttt tttttgtttg tattaaataa | 1200 |
| atttatttt tttagagttt gtttttatat taggtaatgt atatgtttga gaaattttg | 1260 |
| ttttagatag ttgttttata tgtaggaggg gaaggggagg ggaaggagag agtagtttga | 1320 |
| ttttttaaaa ggaattttt gaattagggt ttttgattta gtgaattttg tgttttgaa | 1380 |
| aattaagggt tgaggggta gggggatatt tttagttgt ataggtgatt ttgattttg | 1440 |
| gtggggtttt tataattagg aaagaatagt tttgttttt tttatgatta aaagaagaag | 1500 |
| ttatatttt tttatgatat taaatatttt gatttaattt ggtagttagg aaggttgtat | 1560 |
| tgtggaggaa ggaaatgggg tggggtgga tttttttta atagagtgaa tgtatttaaa | 1620 |
| tatgtttttg ttggtaggtg ggggagtgtg gttgggagta gggaggttgg agggtggtgt | 1680 |
| gggggtagg tgggaggag tttagttttt ttttttgtt aatgttggtt ttggtgaggg | 1740 |
| ttgttttgg ttggtgtttt tggggagat ttaatttggg gtgattttag gggtgttata | 1800 |
| tttgttaagt gtttggagtt aatagtattt tttttgagta tttgtttatg gtgttttttt | 1860 |

```
gtttggaaag atattgtggt ttttttagag gatttgaggg ataggggttgg aggggggtttt  1920 tttgttagta ttggaggaag aaagaggagg ggttggttgg ttattagagg gtggggtgga   1980
ttgtgtgtgt ttggtggttg tggagagggg gagagtaggt agtgggtggt ggggagtagt   2040
atggagttgg tggtggggag tagtatggag ttttggttg attggttggt tatggttgtg    2100
gtttggggtt gggtagagga ggtgtgggtg ttgttggagg tgggggtgtt gtttaatgta   2160
ttgaatagtt atggttggag gttgatttag gtgggtagag ggtttgtagt gggagtaggg   2220
gatggtgggt gattttggag gatgaagttt gtagggggaat tggaattagg tagtgttttg  2280
attttttgga aaaaggggag gttttttggg gagtttttag aagggggtttg taattataga  2340 ttttttttg gtgatgtttt ggggggtttgg gaagttaagg aagaggaatg aggagttatg  2400
tgtgtataga tttttttgaat gttgagaaga tttgaagggg ggaatatatt tgtattagat  2460
ggaagtatgt tttttattag atataaaatt tatgaatgtt tgggataaaa agggagtttt   2520
aaagaaatgt aagatgtgtt gggattattt agttttttaat ttatagatat ttggatggag  2580
ttattttttt ttattaggag ggattattag tggaaatttg tggtgtatgt tggaataaat   2640
attgaatata aattttgatt gaaattattt agaagtggtt gggtgtggtg ttttatgttt   2700
tgtaattttt ttatttttggg agattaaggt ggggggaatt atttgaggtt gggagtttga   2760
gattagtttg gttaataggt gaaattttgt ttttattaaa aatataaaaa gtagttgggg   2820
gtggtggtag gtgtttgtaa ttttagttat ttgggaggtt gaggtaggag aattgtttga   2880
atttgggagg ttgaggttgt agtgaatagt gagatggagt tattttattt agttttgggt   2940
gatagagtga gattttgttg aaagaaagaa agagagaaag agagagagaa aaattattta   3000
gaagtaatta tatattgtgt ttattttttaa ttgagtaggg taaataaaata tatgtttgtt  3060 gtaggaattt aggaaataat gagttatatt tatgtgatta tttttagaggt aatatgtagt  3120 tattattttg ggaatatttg ttaatatttt tgtttttttta ttattttttag tttatttgat  3180 atagtttatt tgtgataaga gtttttaatt ttttattttt gaatagaggt gttttttttt    3240
tttttatttt tgttttgtga gggagttagg ggaggattta aaagtaatta atatatgggt   3300
aatttagtat ttttaaaatt ttgttaatag tttgaatttg ggagtttggt tttgtagttt   3360
tataatattt tagaagagat tttatttgtt taaaaataaa aaggaaaaag aaaagtggat   3420
agttttgata atttttaatg gagaagggag aagaatatgt agaaagggg aaatgatgtt    3480 ggtttagaat tttaattata ttggtgtttta atataggaat atttatttat ataatatttt   3540
aaagtattaa atttatatta gtatattatt aaatggatat attattaaat gggtttaagt   3600
attttatata ttttaatttta attgatttat ttttttttg ttttggattt ttattatgat   3660
ttaaatattt atatatgggt tattttttag attttttata ttatgaaata taagaaaaat   3720
ttttaaggtt agttttatga ttaagatgaa ggattttatt gaatatataa aataataaat   3780
atattgtaat attttgtttt tttttttgta gttgtaattt ggtttgttta tattttttttt  3840 ttgtttttttt gaaaattgag ttagttttat tttttttagga taggatttaa taattataat  3900
ataatttagt ataattttt gatttaggta aattatgtaa tttgtgttta gtatgaaatg     3960
tatttaaaaa taagtaattt tttttttaata ttattatttt taaattaata taataaataa   4020
tagttatttt aaaataaatt gtttattttt attatgtagt atttaaattt taaggttgtt   4080
atgattgtag atagtatttt aaattttttt tttggaaatg gttttgtttt taagatgatt   4140
taggaattaa agaggtgatt attttttgtt taatgaattt ttaaattata aatttgggaa   4200
gtgttttagt ttttttattgt tgttgttata aattattata aatgtgttag ttaaaataaa  4260
```

-continued

```
tataaaatta ttattttata gttttagaga ttagaagtta aaaatgggtt tataaggttt    4320 tattttttt ggaaatttta aggggtaatt tgttttttg ttttttttag tttttagtga    4380
ttattaaatt ttttggttta tggttttgt attttttg tggtttgtgt ttttattttt    4440 gtatttttt tttgattgtg atttttaat aaaaatattt ggggtatgt tgggtttatt    4500 ttgaaattt tggataattt tttttaagat tattaattaa attatatttg taaagttttt    4560
tttgttatat aagttaatgt attaaaagtt tttgaggatt aggatataga tattgggggt    4620 ggggggtat tatttagttt attataggaa ggaattttag ggttaattaa attagttttt    4680
ttattttata tttgaagaaa ttgaagtttt ggaattggag agtattatgt taaatgaaat    4740
aagttaaata tagaaagata aatattatat gttttattt atttgtgaaa tataaaataa    4800
ttatattttt agtagtaaag agtagaatgg tggttattag agttgggggg tgggaggaat    4860
ggggagatgg taattaagat ataaagtttt agttaagatg ggaggaataa gtttgattgt    4920 ttttttgag atgtgtttta tagtatgatg aatatagtta aatagtaaat tttaaatgtt    4980
tttatttgat aaaaatgtta aatatttgag atgatggata ggttatttag tttgatttaa    5040
taatttttta ttgtgtttaa agattataat tttatattgt attatataaa tatatataat    5100
tgtattattt taatatataa ttttaaaatt aatataatga aaagaaatt gaagtttaat    5160 attttagaa gttaagtgta atttaaaagt tttgtgagaa tttgttttaa taaataaata    5220
agtttttttt ttttaataat tattatattt tgtgtttgga tatatagtag tgaataaaaa    5280 aaaaaaaaa aaaaaaatt tttaggttta atataatttt aggaagaaat tttagtagtt    5340
gtattttagg ggaaatatag gaagttagtt tggagtaaaa gttagtttgt ttttgttttt    5400
ttgttatttt gtttgtgttt tatagtgttt tttgtttgtg atgatagttt tgtagaagtt    5460
tggaggatat aatggaattt attgtgtatt gaagaatgga tagagaattt aagaaggaaa    5520
ttggaaattg gaagtaaatg tagggtaat tagatatttg gggtttgtgt ggggtttgt    5580 ttggtggtga ggggttttta tataagttttt tttttgtta tgttggtttt tattttggtt    5640
ttgattattt tgttttttt ggtagg                                        5666
```

<210> SEQ ID NO 20
<211> LENGTH: 5666
<212> TYPE: DNA
<213> ORGANISM: Artificial Sequence
<220> FEATURE:
<223> OTHER INFORMATION: chemically treated genomic DNA (Homo sapiens)

<400> SEQUENCE: 20

```
tttgttagag agaatagaat ggttagagtt agggtggggg ttggtatgat ggaaaggaag      60
tttgtgtaga gttttttat tgttaagtag attttatat aagttttagg tgtttaatta     120
tttttatatt tgttttagt ttttaatttt tttttgagt tttttattta tttttagta     180 tataatgaat tttattatat tttttgaatt tttgtggagt tgttgttata ggtagagagt     240
attgtgaggt atgggtaaaa tagtaaaggg gtagggatag attgatttt attttaggtt     300 aattttttgt atttttttg agatataatt attgaaattt tttttgaaa ttatgttagg     360 tttggagatt tttttttt tttttttt tgttattgt tgtatattta agtgtagaat     420
gtggtaattg ttaaaagag aaaatttgtt tgtttgttaa ataaattt tataaaattt     480 ttaagttata tttagttttt gggaatgttg aattttaatt tttttttat tatattagtt     540 ttaaaattat atattgggat agtatagttg tatatattta tgtggataa tatgaagtta     600 tgatttttga atataatggg gaattattaa gttaagttaa gtaatttatt tattattta     660
```

```
aatatttgat attttgtta aatgagagta tttgggattt attatttagt tatatttatt    720
atgttatgaa atatatttta aaaaaaataa ttaaatttat ttttttttatt ttaattgagg   780 ttttatattt tgattattat ttttttattt tttttatttt ttagttttag taattattat    840
tttatttttt attgttaaga atgtaattgt tttatttttt atagataagt gagaatatgt    900
gatatttgtt tttttgtgtt tggtttattt tatttagtat aatgtttttt aatttaaaa     960 ttttaatttt tttaagtata aataagaag gttagtttaa ttaattttaa aattttttt     1020 tgtggtaggt tgaataatgt ttttttattt ttaatgttta tgttttaatt tttaaaaatt   1080
tttaatatat taatttatgt ggtaaaagag ggttttgtaga tgtgatttaa ttaatggttt  1140
tgagggagat tatttagaat tttttagggtg ggtttaatat aattttaagt gttttttatta 1200 gagggttata gttagagaga agatataaga atgaagtat aggttataga gaaaatatag   1260
agattatgag ttaaggaatt tgatggttat tagaagttgg aaaagataag gaaatagatt   1320 gtttttttaga gttttttaaaa ggaatgaaat tttgtggatt tattttttgat ttttgattt   1380 tagaattgta aataataat tttgtgtttg ttttagttaa tatatttgtg ataatttgta    1440
atagtagtag taggaaaatta aaatattttt taggtttatg atttgagagt ttattaaata  1500
agagatggtt atttttttgg tttttaaaatt atttttggaaa taagttatt tttagagagg   1560 aattttaaaa tattgtttgt agttatagta atttaaaaat ttgagtgttg tatgggtggaa 1620 gtagataatt tattttaagga taattgttat ttgttatatt agtttggagga tggtggtgtt 1680 aaagaggagt tatttattt taggtatatt ttatattaaa ataaattgt ataatttgtt    1740 taaattaagg aattatatta aattatatta tggttattaa attttgtttt gagaaagtga  1800
aattgattta gttttttaaag agataaagag aaagtataag taaattaaat tgtagttata 1860
aaaagaaaga taaatgttg tagtatattt attgttttgt gtatttaatg aagttttttg   1920
ttttggttat aaaattagtt ttaaaggttt tttttatatt ttatagtatg aaaaatttaa   1980
aaagtaattt atatgtaaat atttaaatta tgatagaaat ttaaagtaaa aagaaaatga  2040
attaattgaa ttaaaatgtg taggatgttt aaattttattt gataatatat ttatttgata  2100
atatattaat atgaatttag tattttttaaaa tgttatataaa ataaatgttt ttatattaaa 2160
tattaatgta gttaggattt taagttaata ttattttttt tttttttatat gttttttttt    2220 ttttttttatt aaaaattgtt aaaattattt attttttttt ttttttttgg ttttttaaata 2280 aataaggttt ttttttaagat attgtaggat tataaagtta aattttttggg tttaagttgt 2340 tggtaaaatt ttagagatgt taagttattt atgtattaat tattttttaaa ttttttttta  2400 attttttttat aaaataggag tagggagagg agaaatattt ttgtttaaaa atgaggaatt 2460
gaaaattttt attataaata aattatatta agtaagttaa agatagtaaa agagtaaaaa  2520
tgttagtaga tattttttaaa atggtaatta tatattattt ttggaatgat tatatgaatg  2580
tggtttatta tttttttaagt tttttatagta aatatatatt tatttgtttt atttagttaa 2640
aaataaatat aatatgtagt tgttttttgaa taattttttt tttttttttt ttttttttttt 2700 ttttttttgat aaagttttat tttgttattt aggttggagt gaagtggttt tattttgttg  2760
tttattataa ttttagttttt ttgggtttaa gtgattttttt tgttttaatt ttttgagtag 2820
ttgggattat aggtgtttgt tattattttt ggttattttt tgtattttta gtagaggtga   2880
ggttttattt gttggttagg ttggttttga atttttgatt ttaggtgatt tttttttgttt   2940 tgatttttta aagtgaaggg attataaggt gtgaggtatt gtgtttggtt gttttgaat   3000 aattttgatt aaaattttata tttgatatttt attttaatat atattataga ttttttattga 3060
```

```
taatttttt   tagtaagaaa   gataagtttt   atttaggtat   ttgtgaattg   gaggttaagt    3120
agttttagta   tattttatat   ttttttaaga   ttttttttt   attttaaatg   tttgtaaatt    3180
ttgtatttga   taaagagtat   attttattt   aatataaata   tgttttttt   tttagatttt    3240 tttagtattt   gagagatttg   tatgtgtgtg   gttttttatt   tttttttttt   ggttttttaa    3300
gtttttaggg   tgttgttagg   aggaggtttg   tgattataaa   ttttttttga   aaattttta    3360 ggaagttttt   ttttttttg   gagaattgaa   gtgttatttg   attttaattt   ttttgtaaat    3420
tttgtttttt   agagttgttt   gttattttt   gttttgttg   tagattttt   atttattttg    3480 attggttttt   gattgtaatt   atttggtgtg   ttgggtagtg   tttttgtttt   tagtagtgtt    3540
tgtatttttt   ttatttgatt   ttgggttgtg   gttgtggtta   gttagttagt   tgaaggtttt    3600
atgttgtttt   ttgttgttgg   ttttatgttg   tttttgttg   tttgttgttt   gttttttttt    3660
tttttgtagt   tgttgagtgt   atgtggtttg   tttatttt   tggtgattag   ttagttttt   3720 ttttttttt   ttttggtgtt   ggtggaagag   tttttttga   ttttgtttt   taaattttt    3780 ggagggattg   tggtatttt   ttaggtaagg   ggatgttgtg   agtgagtgtt   tggaggaggt    3840
gttattaatt   ttgagtatt   agtgaatgtg   tatttttga   agttgtttta   ggttgggttt    3900
tttttggggg   tattagttgg   aagtagtttt   tgttagagtt   agtgttggta   aggaaggagg    3960
attgggtttt   tttttattg   ttttttatat   tgttttttgg   ttttttgtt   tttagttgtg    4020 tttttttgtt   tgttagtaaa   ggtgtgtttg   agtgtgttta   ttttgttaaa   aagaaatttg    4080
tttttgtttt   gttttttttt   tttgtgatat   aattttttta   attgttaaat   tgaattgggg    4140
tgtttggtgt   tatagggaaa   gtatggttt   ttttttaat   tataagaaaa   agtaaaatta    4200 ttttttta   gttgtgagag   ttttattgag   aattgaaatt   atttgtatga   ttagaaagtg    4260 ttttttatt   tttttaattt   ttgattttta   ggagtgtggg   gttattaag   ttagaaattt    4320 tagtttaaag   gattttttt   ggagagttgg   attgtttttt   tttttttttt   tttttttttt    4380
tttgtgtgta   aaatggttgt   ttggggtaag   ggttttttag   atgtgtatat   tgtttggtat    4440
aagagtagat   tttgaaaaga   tgaggtttat   ttaatatgga   tggggagaa   ttttgtttgt    4500 aggtagatag   gaaaatgggg   agggagttat   tggaaggatg   gatttatttt   ttaaagttat    4560 aattttaga   ttagaaaaag   tgtttagtgt   tttagaagta   gagttgtata   gtgatttaaa    4620
gattagtttt   aaatattgtt   ttgtttttt   tatattttt   atatttttt   tttttattga    4680 aaatatttg   tattttgt   aattataaag   ggggaaggga   atatgagtgt   tttttgtttt    4740
ataggggttg   ttgtgagttt   aaatgatgta   ttaatatata   taagttttaa   gaatagtgtt    4800
atatatttta   agttaatatt   tgttagtttt   tgaattattt   gttttgagga   ttggtttgta    4860
attttgtttt   gaggtataga   aagaaaatgt   tttggagtag   gatgtggtgg   tttatatttg    4920
taattttagt   attttgggaa   gttgaggtgg   gtagattatt   tgaggttagg   agtttgaggt    4980
tagtttggtt   aaaatggtga   tattttgttt   ttattaaaaa   tataaaaatt   agttggttat    5040
ggtggtgtat   gtgtgtaatt   ttagttattt   aggaggttga   ggtaggagaa   ttgtttgaat    5100
ttgggaggta   gaggttgtag   taagttgaga   ttgtgttatt   atttttagt   ttgggtgata    5160 gaatgagatt   ttgatttaaa   aaaaaaaaa   aatgttttgg   atagaattat   tattattata    5220
taaaaggaaa   gtttggatgt   ggtggtttat   gtttataatt   ttagtatttt   gggaggttga    5280
gataggtgga   ttatttgagg   ttaggagttt   gagataagtt   tgattaatat   ggtgaaattt    5340 tgttttatt   aaaaaatata   aaattagtgg   ggtttggtgg   tgtatgtttg   taattttagt    5400
tatttggagg   ttgatgtagg   agaattgttt   gaatttagga   gaaggtggag   gttgtagtga    5460
```

```
gttgagattg tgttattgta ttttagtttg ggagataaga gtgaaatttg gttttaagaa    5520
aaaaagaaag aaagaaagaa agaaagatta agaagaattt attttttgaa aagattatgg    5580
gtatttttta ttattttat ttataaagaa aagttaaata gtattaaaga gtataataag     5640
tgtaaggagg taaaagtttt aatttt                                          5666
```

<210> SEQ ID NO 21
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 21

```
cgcggtttcg attttaatgc                                                 20
```

<210> SEQ ID NO 22
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 22

```
actccgactt aacccgacga t                                               21
```

<210> SEQ ID NO 23
<211> LENGTH: 28
<212> TYPE: DNA
<213> ORGANISM: Artificial Sequence
<220> FEATURE:
<223> OTHER INFORMATION: chemically treated genomic DNA (Homo sapiens)

<400> SEQUENCE: 23

```
cgacgaaatt cctaacgcaa ccgcttaa                                        28
```

<210> SEQ ID NO 24
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 24

```
tttcggatgg gaacggtgta                                                 20
```

<210> SEQ ID NO 25
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 25

```
ctcccaccgc cgttacc                                                    17
```

<210> SEQ ID NO 26
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 26

```
cccgtcctaa ccgtccgccc t                                               21
```

```
<210> SEQ ID NO 27
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 27
tcgtcgtcgt ttcggttagt t                                                 21

<210> SEQ ID NO 28
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 28
ccctccgaaa cgctatcga                                                    19

<210> SEQ ID NO 29
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 29
cgaccataaa cgccaacgcc g                                                 21

<210> SEQ ID NO 30
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 30 ttttttttc ggacgtcgtt g                                                  21

<210> SEQ ID NO 31
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 31
cctctacata cgccgcgaat                                                   20

<210> SEQ ID NO 32
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 32
aattaccgaa aacatcgacc ga                                                22

<210> SEQ ID NO 33
<211> LENGTH: 22
<212> TYPE: DNA
<213> ORGANISM: Artificial Sequence
<220> FEATURE:
<223> OTHER INFORMATION: chemically treated genomic DNA (Homo sapiens)
```

```
<400> SEQUENCE: 33 tggaatttc ggttgattgg tt                                          22

<210> SEQ ID NO 34
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 34
aacaacgtcc gcacctcct                                             19

<210> SEQ ID NO 35
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 35
acccgacccc gaaccgcg                                              18

<210> SEQ ID NO 36
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 36
gaaccaaaac gctccccat                                             19

<210> SEQ ID NO 37
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 37
ttatatgtcg gttacgtgcg tttatat                                    27

<210> SEQ ID NO 38
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 38
cccgtcgaaa acccgccgat ta                                         22

<210> SEQ ID NO 39
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 39
gcgtcggagg ttaaggttgt t                                          21
```

-continued

<210> SEQ ID NO 40
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 40
ctctccaaaa ttaccgtacg cg                                        22

<210> SEQ ID NO 41
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 41
aactcgctcg cccgccgaa                                            19

<210> SEQ ID NO 42
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 42
tttcggatgg gaacggtgta                                           20

<210> SEQ ID NO 43
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 43
ctcccaccgc cgttacc                                              17

<210> SEQ ID NO 44
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 44
cccgtcctaa ccgtccgccc t                                         21

<210> SEQ ID NO 45
<211> LENGTH: 2501
<212> TYPE: DNA
<213> ORGANISM: Homo Sapiens

<400> SEQUENCE: 45
cttggactct aatgtgtatt ttacacttac agcacaatta atttgggact agctacattt    60
cagctcaaca atagccaata gcatatggga tagcgcaaat aaactctgcg tctctgttgc   120
ttctttgggt ctcggagacc tcaacccttt cttcagattg caaaccttct tgccttcaag   180
cctcggctcc aacaccagtc cggcagagga acccagtcta atgaggtacg ctcccttcct   240
gccattctct attccattaa cctgtttcgt ggtaaacgta ggactgatcc tccaaaatta   300
ccttattaat tagcttacat atttattatc tatctgtccc accagaatgc aggtttccgg   360

-continued

| | |
|---|---|
| aaggcaggga tttaaaaaaa tctgttttgt tctatgtgat tttcccatac caagcaccgt | 420 |
| gcccggcaca agctgggatc ccagtacaca tctcggacg gaagaaccgt gtttccctag | 480 |
| aacccagtca gagggcagct tagcaatgtg tcacaggtgg ggcgcccgcg ttccgggcgg | 540 |
| acgcactggc tccccggccg gcgtgggtgt ggggcgagtg ggtgtgtgcg gggtgtgcgc | 600 |
| ggtagagcgc gccagcgagc ccggagcgcg gagctgggag gagcagcgag cgccgcgcag | 660 |
| aacccgcagc gccggcctgg cagggcagct cggaggtggg tgggccgcgc cgccagcccg | 720 |
| cttgcagggt ccccattggc cgcctgccgg ccgccctccg cccaaaaggc ggcaaggagc | 780 |
| cgagaggctg cttcggagtg tgaggaggac agccggaccg agccaacgcc ggggactttg | 840 |
| ttccctccgc ggaggggact cggcaactcg cagcggcagg gtctgggcc ggcgcctggg | 900 |
| agggatctgc gccccccact cactccctag ctgtgttccc gccgccgccc cggctagtct | 960 |
| ccggcgctgg cgcctatggt cggcctccga cagcgctccg gagggaccgg gggagctccc | 1020 |
| aggcgcccgg gtgagtagcc aggcgcggct ccccggtccc cccgaccccc ggcgccagct | 1080 |
| tttgctttcc cagccagggc gcggtggggt ttgtccgggc agtgcctcga gcaactggga | 1140 |
| aggccaaggc ggagggaaac ttggcttcgg ggagaagtgc gatcgcagcc gggaggcttc | 1200 |
| cccagccccg cgggccgggt gagaacaggt ggcgccggcc cgaccaggcg ctttgtgtcg | 1260 |
| gggcgcgagg atctggagcg aactgctgcg cctcggtggg ccgctcccctt ccctcccttg | 1320 |
| ctcccccggg cggccgcacg ccgggtcggc cgggtaacgg agagggagtc gccaggaatg | 1380 |
| tggctctggg gactgcctcg ctcggggaag gggagagggt ggccacggtg ttaggagagg | 1440 |
| cgcgggagcc gagaggtggc gcggggggtgc caccgttgcc gcaggctgga gagagattgc | 1500 |
| tcccagtgag gcgcgtaccg tctgggcgag ggcttcattc ttccgcggcg tccctggagg | 1560 |
| tgggaaagct gggtgggcat gtgtgcagag aaagggagg cggggaggcc agtcacttcc | 1620 |
| ggagccggtt ctgatcccaa cagaccgccc agcgtttggg gacgccgacc tcggggtgcc | 1680 |
| gtggtgcccg gccccacgcg cgcgcggggc tgaggggtcg ggggcgtccc tggccgccca | 1740 |
| gctttaacaa agggtgctcc tctccacccc gcgaggaggg gcagctccgg agacccggtc | 1800 |
| ttcagcgagc ggggtcttag cgccggggag gtctacttcc ttttgggggtt gccattttac | 1860 |
| tattattatt gccttttttt tttcttcaaa aggactggag actgatgcat gaggggcta | 1920 |
| cggaggcgca ggagcggtgg tgatggtctg ggaagcggag ctgaagtgcc ctgggctttg | 1980 |
| gtgaggcgtg acagtttatc atgaccgtgt tcaggcagga aaacgtggat gattactacg | 2040 |
| acaccggcga ggaacttggc aggtaaaggg ggtaccagaa gcgtaccctc ctggattgtg | 2100 |
| gaaatgcata acgatgggc cattgggtgg taaacaaatg cagtttgaat caggcgtctc | 2160 |
| cctcgccctt tctggagatg cgcaaatcat agagaaaaga gttactaacc cagcggtaaa | 2220 |
| ccgcctgatc caagggcctg ggggtggagg agaggcagca gttcagggct agattatgat | 2280 |
| gcacagtata ttgatccagt ccctggaca aaatcagatt taattgtccg tgctaactct | 2340 |
| tgtcagccct gcccttctg tgacaacagg acaaacacta agattataat tgcaattgga | 2400 |
| gttagctttt atgtgtgatt taaacggagg gtacaaacta attaataggt tttaaaaatc | 2460 |
| ttagtacttt accctctatc taaattttca gtgtaatttg a | 2501 |

<210> SEQ ID NO 46
<211> LENGTH: 4501
<212> TYPE: DNA
<213> ORGANISM: Homo Sapiens

```
<400> SEQUENCE: 46
ttcacttgtc ctacaggatt ccccatggaa tcttggagtt tttgaggcga gagggatcct    60
ggataccact gagttctatc tttcatccaa taaacacaga agtggacgcc tggacaggca   120
aagtgacttg accaaggcag gtgcacagct attctgcaac attgggaaca aatctcaggt   180
cttttgattt tttgtttcca ctttactctc ttttcatttc ccagaaacaa agttttcatg   240 tgctttttt  tatagtgata tgtttggaat gcattagcta gtaatttagg aagggaaaaa   300
aataaacaca caagagataa acctgtcagg aggacaaacc tgtattgctt ctgattggct   360
cagagggtga ttattatcat ggtagagaat tatttaatca gtgtaagtaa aatttctctg   420
tgggctgggc actgtacaaa gactcaaacg aatctgtcta cagatctgaa aagcagatac   480
gagatctgtg aatggctggg gtttccaagc ccacagtaca agcatgggcc acaccttaca   540
gcttggagga ctgagccctg aaaatgggca agttccttca cttctctgaa ccttattttt   600
cccacattta aaacaaggat gagtagtttc tgaggtcctt tttacgactt ctcttcctac   660
agactctagc atcctataac ttgatacaaa gagggtggat atgaactcac ctttcctaga   720
aaagttccag gaaagagaat accaggtcat cctagtaggt gtgtagacag gccagataga   780
tcttgaaact tactcagttc ttcccagatg tataactcta tcattgttct tagctgtcaa   840
gagaaagcag gagagcctgc atcttcattc tttttttttt ttttttttt  tttggagacg   900 gagtctcact ccatcaccta ggctagagtg cagtggcatg atctcagctc actgcaagct   960
ccgcctccca ggttcacgcc attcctctgc ctcagcctcc caagtaactg ggactacagg  1020
cgcccaccac cacacctggc taatttttg  tgttgttagt acagacgggg tttcaccatg  1080
ttagccagga tggtctcgat ctcctgacct cgtgatccgc ccaccttggc ctctcaaagt  1140
gctgggatta caggcgtgag ccaccgcacc cagcctgcat cttcattctt actgttagcc  1200
tcaggttcac cccacctagc ttattaagtg atgttgaata accaattctt acatattatt  1260
aggctcatgg acaccatgac atccagactg atgggtgcct gctgaagggg gtgaccctag  1320
caggaggact cccctacgca aggattcatg gagtttgctg tttcttttcc ttagggtgag  1380
aaccaaactg ccttcacacg gtgggcagag gggaactgac tcaggtttgg aataagagag  1440
aacatcccaa ctgaaaagct cttggaattc gctgaacttc aagacactgt gtggaccagc  1500
ttaggatagg gagtgagaag aaattaacca aaaggtaatt tcgttacttt tcagctggaa  1560
aaaagatcag attatacttg tgctttcata attaagtagc tgctggaaaa aaacgcttca  1620
gatgctttct atgagaaaac tgctgcttga agttcagcag aagttatcta cttgatactt  1680
atattccagg caaggccttc cgttggagaa aatatcggca cttttggacaa aactgaaatg  1740 tgaaaagaaa gggaagagag ggcctctatc atgtaagatg cttatccaaa gtggatttgg  1800
tctggaaagt cttctaaaac cttccacatg actgtggaat aagtcatgtg gggcgcgggg  1860
ataagcgaat ctctcaaatt ccaccacgta tgccctcatt caacctggat ccttagagtg  1920
gcctccaggg cactctgctc aggactcagt cagctgttgg ccacacccat gctctccagt  1980
ctcctgagac cctatttggt tctgagaggg ctaaaaagca gtgtggctaa atatcccagg  2040
cctcaaagta ttcctactgt ggttggggaa gcaatagaat catacccat  aaaacaatga  2100 aaacagtgct agaaaaacat cgagagacag aaacatctct acgagttagg ccacagttag  2160
agtgaaggca gggaaggttt ttaaagctgg gtggagggga caagtcaaaa agatgtggaa  2220
actggtttcc ctttcctatg gctaaagtgc tcaaggggga aaaggagtt  tcaaaaatgt  2280 tcttggaaat accatctctc acgaattctt cggcctctgc tgtcccaatg tcacttgtct  2340
```

-continued

| | |
|---|---|
| gagatgtaaa cagaggagtt ctgagaaaga agctgaactt gcatttctcc ctgtttctat | 2400 |
| ttgttccaaa cttgtggcat ttctaacagg atgaagcgga agagaaaggg aaagagacaa | 2460 |
| aagtgtagaa agatggaaga tcccagctgc aaatggccat ttgcagttag atggaacagc | 2520 |
| tgctgacgtt cagggaaatg catgtctctc ttcagatggg aaggagcagt ggaaagggt | 2580 |
| gacgagttcc tggctggcca ccaatcatcc catctttctg tgccggttcc tcatctggaa | 2640 |
| agtgggagtg atacttgtgc ttgcttttcc tacccacaaa gattattgtg agagctataa | 2700 |
| tacggtgaga tacagaatcc tgcttttaaa aatacaaagc agaatcaaga tgtcaataat | 2760 |
| aaggatagta attgtgttag ttatctgcaa tcatctatta tagctagtcg tctaggatcc | 2820 |
| tggatcgttc tcctggtttt actacagttt tggatcagct caccccaaa tcccttgctg | 2880 |
| aagggtggag ctctgtcagc catgggcagg gaaccacttc ctcttgcctt tctactttct | 2940 |
| gtctttcaaa catgcccagg gtctttgcac ttgctgttcc ccctgcctgg tacctctctc | 3000 |
| ctgtggcttg ccccagagct gatccttgtc tttgtccact tctcagcgag gatggcactt | 3060 |
| cagggagccc ttcccttact atcgcagaga gagcaggccc tccccagtca tgtccaaccc | 3120 |
| agaactctgt tttgtttct tcatagccct agcatcacag aaaatcaccc tgtgcattca | 3180 |
| tggatgtcca cgggggcaag ggctttgtgt tgcttaaccc agcatcctga accgtgtttg | 3240 |
| ttgaatgaat acagaacccc gtttgctctg ggagagcaca gaaaacagtc ttctatcata | 3300 |
| tatcatagcc agctgcaaac agcagatggc ttcccatatc ccagagagta agaaccagag | 3360 |
| agagagagaa agagagagag tttgggtctt tctcctctgt gcctgctctc tccagagaaa | 3420 |
| ctggagggt agcagttagc attcccccgc tggttccacc aagcacagtc aaggtctcta | 3480 |
| ggacatggcc acccctcacc tgtggaagcg gtcctgctgg ggtgggtggg tgttagttgg | 3540 |
| ttctggtttg ggtcagagac acccagtggc ccaggtgggc gtggggccag ggcgcagacg | 3600 |
| agaaggggca cgagggctcc gctccgagga cccagcggca agcaccggtc ccgggcgcgc | 3660 |
| cccagcccac ccactcgcgt gcccacggcg gcattattcc ctataaggat ctgaacgatc | 3720 |
| cgggggcggc cccgcccgt tacccccttgc ccccggcccc gccccctttt tggagggccg | 3780 |
| atgaggtaat gcggctctgc cattggtctg aggggggcggg cccaacagc ccgaggcggg | 3840 |
| gtccccgggg gcccagcgct atatcactcg gccgcccagg cagcggcgca gagcgggcag | 3900 |
| caggcaggcg gcgggcgctc agacggcttc tcctcctcct cttgctcctc cagctcctgc | 3960 |
| tccttcgccg ggaggccgcc cgccgagtcc tgcgccagcg ccgaggcagc ctcgctgcgc | 4020 |
| cccatcccgt cccgccgggc actcggaggg cagcgcgccg gaggccaagg ttgccccgca | 4080 |
| cggcccggcg ggcgagcgag ctcgggctgc agcagccccg ccggcggcgc gcacggcaac | 4140 |
| tttggagagg cgagcagcag ccccggcagc ggcggcagca gcggcaatga ccccttggct | 4200 |
| cgggctcatc gtgctcctgg gcagctggag cctggggac tggggcgccg aggcgtgcac | 4260 |
| atgctcgccc agccacccc aggacgcctt ctgcaactcc gacatcggta agcgctcctg | 4320 |
| gtgccccgcc cgagcccac gctgcagcca ggactgcagc gctgcttagg gaggcagggc | 4380 |
| gagccccact cctttcctct gccccaggag aggggcagac ggggttgggg cggagtggag | 4440 |
| aaactcgatg tccttgggcg ggggcgctgg catagctgag aggggaagat gccctgcaga | 4500 |
| g | 4501 |

<210> SEQ ID NO 47
<211> LENGTH: 3001
<212> TYPE: DNA
<213> ORGANISM: Homo Sapiens

```
<400> SEQUENCE: 47
gaagtgctaa tgtcagattt ttacccacta cataagccca ctcttgtact agggcagtga    60
ctttcttctt tgggtgagac cttgaaatct gggattataa ttttgaatta taattataaa   120
atggtatttg gctgtaaatt atctccttt tttttctgtt cctcacagtt gatattatgg    180
attcccataa ggattcatgt cttctattca ctttaatgaa cagttgttgg gcaacaattc   240
tagaagagtt ccaattctca tcaggagaat ggacaaggtg gagaagcaga gaaaatgcaa   300
tgagtagaat gtctaagtca tcactttgga attgactgaa cataaataaa aatgagaaag   360
atacgtaaaa agaagggaa tgggtaagca gggtgatgtc tgggagagga ggggctccat    420
agccatgaga gtcaactctg taacaccta tagggttaca acactgccct tcatatactg    480
aggtagcagc agggaaactt tttaattatt agaaatattg aactttgcct cccaccccca   540
aacattttc tcattcagtt cctgttcttt tttatttctg taattttac tgtttcaaaa     600
atgatctttt ttctttcgga agaagcaatt cttcaaatcc agttcacata aggggatttg   660
atatgttcaa caagctccaa atacactgta tccagcaata cctactacat gcctactttg   720
agctctgagc aacctgcacc tcaagcctag ttctcattgt tttgcttttg gcaaattttc   780
actaagtgcc cttcctcccc aaacacacgt atatgtctac cagaccctaa agcccttat    840
gaacatgcaa actcctccct tctgaaaacc tttgcgtgag tggtcagcag gctaattcat   900
ccattgcaat gtggctttgt gttagggttc tgtttccgtg ctgcctgcaa gataatcaca   960
gatgtgactg catcttagaa gttcctgaat cttcaagac agtctggttc acaagaaaat  1020
taaaaggtgg aggtcgggcg cggtggctca cgcctgcaat cccagcactt tgggaggccg  1080
aggcgggcgg atcacctgag gttgggagtt cgaaaccagc ctgaccaaca tggggaaacc  1140
ccgtctctgc taaaaataca aaattagcca ggcgtggtgg tgcatgcctg taatcccagc  1200
tactcgggag gctgaggcag gagaatcgct tgaacccggg aggcagaggt tgcgatgagc  1260
cgagatcgtg ccattgcact ccagcctggg caacaagagc gaaactctgc cacacacaca  1320
caaacacaca cacacacaca cacacggtgt agtttaggaa gtaaaaaaaa aaaaaaaaa   1380
aaaatcagat ctcccctcac acctcagatc tgaaggcaca aactctaggg ccagggcgtt  1440
cgcctaccca actccacatg cacttgcagg tcacctagca ctcaggtacc tagcactcag  1500
gtacattgtg gctccttacc tctcacgaca gcagcaacaa cgttgattgg aagtttatca  1560
ctgtgtgtta cgggccatgg gccatgtgtg ttagaattt atgtgaaatt aacatttaat  1620
tctcacggac acccctgaaa cagatgccac agccccatt ttgccaacga ggcagctgag  1680
gttcccagag gctcaatacc agcaccatga ccgcagcac gcaaggcaaa cacagccgga  1740
ggtgagcaca tacctgcttc gcaccccatg cgcctaacca caaggttccc tccctccagg  1800
aaggccgttg tcttccctgg gacgacttgc cagctctgag gcatgacagt acgggccccc  1860
agaagggtga ccaggaggcc ctcctcgtcc cagctgccgg cgtcgccgcc cactgcaggg  1920
cccgggctgt gactcgtggg gacggttccc tgcgccccgg cggggaggt gggcggggag   1980
gggcggcggg gcgccgggc ggggctcggg acggccgggc tgggagctgg agcccacagc   2040
gggaagcggc cgccgcccgg gcctcgcagg gctaggcgag gcgaggggg gcggggccgg    2100
gcgctacggg aaggggaggc cgcgcggacc gggagccgca ccgcgccagc cgggctgcag  2160
cggccgcgca ccaaggctgc gatggggctg gagacggaga aggcggacgt acagctcttc  2220
atggacgacg actcctacag ccaccacagc ggcctcgagt acgccgaccc cgagaagttc  2280
gcggactcgg accaggaccg ggatccccac cggctcaact cgcatctcaa ggtgaagccc  2340
```

```
ggggcgggcg ggcccaagtc cccgctgagg ccgggaggtg cgggcgcccc tcagccccgc    2400
cctaacccgt cccaccattg ctaccgggtc ggccccgcag ggtctgagac ccgcacccctt   2460 ccccggtccc acccgtcacc aggccgcccg cgtagccagg aattcttagc caggttcctg    2520 tgcgccacc gtgaccctaa gagaagaggc ggacgccctg gcacgtcctt ccctcctgct     2580
tcccccgccc aaagcgctcc cggttcccgg ggcgtcaggt tggctgacag ttcggggtcc    2640
ctgcgtcctg tctcctcagc tgggcttcga ggatgtgatc gcagagccgg tgactacgca    2700
ctcctttgac aaagtgtgga tctgcagcca tgccctcttt gaaatcagca aatacgtaat    2760
gtacaagttc ctgacggtgt tcctggccat tcccctggcc ttcattgcgg gaattctctt    2820 tgccacccctc agctgtctgc acatctggtg agacggggca caccgggtgg accggctttc   2880
tgaaacatgg gcatattctc cgccacctgc cccctactct cctcttatcc caggccggcg    2940
tcaggaggag gaacgcgcat cagttcccaa gcagtaggaa gaactggaag gccttgaaag    3000
g                                                                    3001

<210> SEQ ID NO 48
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 48
tttggatttt aatgtgtatt ttatatttat agtataatta atttgggatt agttatatttt   60 tagtttaata atagttaata gtatatggga tagcgtaaat aaattttgcg ttttttgttgt   120 ttttttgggt ttcggagatt ttaattttt ttttagattg taaattttt tgttttttaag    180 tttcggtttt aatattagtt cggtagagga atttagttta atgaggtacg ttttttttt    240 gttattttt atttattaa tttgtttcgt ggtaaacgta ggattgattt ttaaaatta      300 ttttattaat tagtttatat atttattatt tatttgtttt attagaatgt aggttttcgg   360
aaggtaggga tttaaaaaaa tttgttttgt ttttatgtgat ttttttatat taagtatcgt   420
gttcggtata agttgggatt ttagtatata tttcgggacg gaagaatcgt gttttttag    480 aatttagtta gagggtagtt tagtaatgtg ttataggtgg ggcgttcgcg tttcgggcgg    540
acgtattggt ttttcggtcg gcgtgggtgt ggggcgagtg ggtgtgtgcg gggtgtgcgc    600
ggtagagcgc gttagcgagt tcggagcgcg gagttgggag gagtagcgag cgtcgcgtag    660
aattcgtagc gtcggtttgg tagggtagtt cggaggtggg tgggtcgcgt cgttagttcg    720
tttgtagggt ttttattggt cgtttgtcgg tcgttttcg tttaaaaggc ggtaaggagt     780
cgagaggttg tttcggagtg tgaggaggat agtcggatcg agttaacgtc ggggattttg    840 ttttttcgc ggagggatt cggtaattcg tagcggtagg gtttggggtc ggcgtttggg      900
agggatttgc gttttttatt tatttttag ttgtgttttc gtcgtcgttt cggttagttt     960
tcggcgttgg cgtttatggt cggttttcga tagcgtttcg gagggatcgg gggagttttt   1020
aggcgttcgg gtgagtagtt aggcgcggtt tttcggtttt ttcgattttc ggcgttagtt   1080 tttgttttt tagttagggc gcggtggggt ttgttcgggt agtgtttcga gtaattggga    1140
aggttaaggc ggagggaaat ttggtttcgg ggagaagtgc gatcgtagtc gggaggtttt   1200
tttagtttcg cgggtcgggt gagaataggt ggcgtcggtt cgattaggcg ttttgtgtcg   1260
gggcgcgagg atttggagcg aattgttgcg tttcggtggg tcgttttttt ttttttttg    1320 ttttttcggg cggtcgtacg tcgggtcggt cgggtaacgg agagggagtc gttaggaatg   1380
```

```
tggttttggg gattgtttcg ttcggggaag gggagagggt ggttacggtg ttaggagagg      1440
cgcgggagtc gagaggtggc gcgggggtgt tatcgttgtc gtaggttgga gagagattgt      1500
ttttagtgag gcgcgtatcg tttgggcgag ggttttattt tttcgcggcg ttttttggagg     1560 tgggaaagtt gggtgggtat gtgtgtagag aaagggagg cggggaggtt agttattttc       1620
ggagtcggtt ttgatttaa tagatcgttt agcgtttggg gacgtcgatt tcggggtgtc       1680
gtggtgttcg gttttacgcg cgcgcggggt tgagggggtcg gggcgtttt tggtcgttta     1740 gttttaataa agggtgtttt ttttatttc gcgaggaggg gtagtttcgg agattcggtt       1800
tttagcgagc ggggttttag cgtcgggag gtttattttt ttttgggggtt gttattttat     1860 tattattatt gttttttttt tttttaaa aggattggag attgatgtat gaggggggtta       1920 cggaggcgta ggagcggtgg tgatggtttg ggaagcggag ttgaagtgtt ttgggttttg     1980
gtgaggcgtg atagtttatt atgatcgtgt ttaggtagga aaacgtggat gattattacg      2040
atatcggcga ggaatttggt aggtaaaggg ggtattagaa gcgtatttt ttggattgtg       2100 gaaatgtata acgatggggt tattgggtgg taaataaatg tagtttgaat taggcgtttt      2160
tttcgttttt tttggagatg cgtaaattat agagaaaaga gttattaatt tagcggtaaa      2220
tcgtttgatt taagggttg ggggtggagg agaggtagta gtttaggggtt agattatgat     2280 gtatagtata ttgatttagt ttttttggata aaattagatt taattgttcg tgttaatttt    2340
tgttagtttt tgtttttttg tgataatagg ataaatatta agattataat tgtaattgga     2400
gttagttttt atgtgtgatt taaacggagg gtataaatta attaataggt tttaaaaatt     2460
ttagtatttt attttttatt taaattttta gtgtaatttg a                          2501

<210> SEQ ID NO 49
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 49
ttaaattata ttgaaaattt agatagaggg taaagtatta agatttttaa aatttattaa        60
ttagtttgta tttttcgttt aaattatata taaaagttaa ttttaattgt aattataatt       120
ttagtgtttg ttttgttgtt atagaagggt aagggttgat aagagttagt acggataatt       180
aaatttgatt ttgtttaggg gattggatta atatattgtg tattataatt tagttttgaa       240
ttgttgtttt ttttttattt ttaggttttt ggattaggcg gtttatcgtt gggttagtaa       300
tttttttttt tatgatttgc gtattttag aaagggcgag ggagacgttt gatttaaatt        360
gtatttgttt attattaat ggtttatcg ttatgtattt ttataattta ggagggtacg         420
tttttggtat ttttttatt tgttaagttt ttcgtcggtg tcgtagtaat tatttacgtt        480
tttttgtttg aatacggtta tgataaattg ttacgtttta ttaaagtta gggtatttta       540 gtttcgtttt ttagattatt attatcgttt ttgcgttttc gtagttttt tatgtattag       600 ttttttagttt ttttgaagaa aaaaaagg taataataat agtaaaatgg taattttaaa       660
aggaagtaga tttttcggc gttaagattt cgttcgttga agatcggggtt ttcggagttg     720 ttttttttcg cgggggtggag aggagtattt tttgttaaag ttgggcggtt agggacgttt     780
tcgatttttt agtttcgcgc gcgcgtgggg tcgggtatta cggtatttcg aggtcggcgt      840
ttttaaacgt tgggcggttt gttgggatta gaatcggttt cggaagtgat tggttttttc      900 gtttttttt tttttgtata tatgtttatt tagttttttt atttttaggg acgtcgcgga        960
```

-continued

| | |
|---|---|
| agaatgaagt tttcgtttag acggtacgcg ttttattggg agtaatttt ttttagtttg | 1020 |
| cggtaacggt ggtattttcg cgttattttt cggttttcgc gttttttta atatcgtggt | 1080 |
| tatttttttt tttttttcga gcgaggtagt tttagagtt atatttttgg cgatttttt | 1140 |
| ttcgttattc ggtcgattcg gcgtgcggtc gttcggggga gtaagggagg gaagggagcg | 1200 |
| gtttatcgag gcgtagtagt tcgttttaga ttttcgcgtt tcgatataaa gcgtttggtc | 1260 |
| gggtcggcgt tatttgtttt tattcggttc gcggggttgg ggaagttttt cggttgcgat | 1320 |
| cgtatttttt ttcgaagtta agttttttt cgttttggtt ttttagttg ttcgaggtat | 1380 |
| tgttcggata aattttatcg cgttttggtt gggaaagtaa aagttggcgt cggggtcgg | 1440 |
| ggggatcggg gagtcgcgtt tggttattta ttcgggcgtt tgggagtttt ttcggttttt | 1500 |
| tcggagcgtt gtcggaggtc gattataggc gttagcgtcg gagattagtc ggggcggcgg | 1560 |
| cgggaatata gttagggagt gagtgggggg cgtagatttt tttaggcgt cggttttaga | 1620 |
| ttttgtcgtt gcgagttgtc gagttttttt cgcggaggga ataaagtttt cggcgttggt | 1680 |
| tcggttcggt tgttttttt atatttcgaa gtagttttc ggtttttgt cgttttttgg | 1740 |
| gcggagggcg gtcggtaggc ggttaatggg gattttgtaa gcgggttggc ggcgcggttt | 1800 |
| atttattttc gagttgtttt gttaggtcgg cgttgcgggt tttgcgcggc gttcgttgtt | 1860 |
| tttttagtt tcgcgtttcg ggttcgttgg cgcgttttat cgcgtatatt tcgtatatat | 1920 |
| ttattcgttt tatatttacg tcggtcgggg agttagtgcg ttcgttcgga acgcgggcgt | 1980 |
| tttatttgtg atatattgtt aagttgtttt ttgattgggt tttagggaaa tacggttttt | 2040 |
| tcgtttcgag atgtgtattg ggattttagt ttgtgtcggg tacggtgttt ggtatgggaa | 2100 |
| aattatatag aataaaatag attttttttaa attttttgttt ttcggaaatt tgtattttgg | 2160 |
| tgggatagat agataataaa tatgtaagtt aattaataag gtaattttgg aggattagtt | 2220 |
| ttacgtttat tacgaaatag gttaatgaa tagagaatgg taggaaggga gcgtattta | 2280 |
| ttagattggg ttttttttgtc ggattggtgt tggagtcgag gtttgaaggt aagaaggttt | 2340 |
| gtaatttgaa gaaaggggttg aggttttcga gatttaaaga agtaatagag acgtagagtt | 2400 |
| tatttgcgtt atttatatg ttattggtta ttgttgagtt gaaatgtagt tagttttaaa | 2460 |
| ttaattgtgt tgtaagtgta aaatatatat tagagtttaa g | 2501 |

<210> SEQ ID NO 50
<211> LENGTH: 4501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 50

| | |
|---|---|
| tttatttgtt ttataggatt ttttatggaa ttttggagtt tttgaggcga gagggatttt | 60 |
| ggatattatt gagttttatt tttttatttaa taaatataga agtggacgtt tggataggta | 120 |
| aagtgatttg attaaggtag gtgtatagtt attttgtaat attgggaata aattttaggt | 180 |
| tttttgattt tttgttttta ttttatttt tttttatttt ttagaaataa agttttatg | 240 |
| tgttttttt tatagtgata tgtttggaat gtattagtta gtaatttagg aagggaaaaa | 300 |
| aataaatata taagagataa atttgttagg aggataaatt tgtattgttt ttgattggtt | 360 |
| tagagggtga ttattattat ggtagagaat tatttaatta gtgtaagtaa aatttttttg | 420 |
| tgggttgggt attgtataaa gatttaaacg aatttgttta tagatttgaa aagtagatac | 480 |
| gagatttgtg aatggttggg gttttttaagt ttatagtata agtatgggtt atatttttata | 540 |

```
gtttggagga ttgagttttg aaaatgggta agtttttta ttttttgaa ttttattttt      600 tttatattta aaataaggat gagtagtttt tgaggttttt tttacgattt tttttttat      660 agattttagt attttataat ttgatataaa gagggtggat atgaatttat tttttttaga     720
aaagttttag gaaagagaat attaggttat tttagtaggt gtgtagatag gttagataga     780
ttttgaaatt tatttagttt tttttagatg tataatttta ttattgtttt tagttgttaa     840
gagaaagtag gagagtttgt attttatttt tttttttttt tttttttttt tttggagacg     900 gagtttatt ttattattta ggttagagtg tagtggtatg attttagttt attgtaagtt      960 tcgttttta ggtttacgtt attttttgt tttagttttt taagtaattg ggattatagg       1020
cgtttattat tatatttggt taatttttg tgttgttagt atagacgggg ttttattatg      1080
ttagttagga tggtttcgat tttttgattt cgtgattcgt ttattttggt tttttaaagt     1140
gttgggatta taggcgtgag ttatcgtatt tagtttgtat tttatttttt attgttagtt     1200
ttaggtttat tttatttagt ttattaagtg atgttgaata attaattttt atatattatt    1260
aggtttatgg atattatgat atttagattg atgggtgttt gttgaagggg gtgattttag    1320
taggaggatt tttttacgta aggatttatg gagtttgttg tttttttttt ttagggtgag    1380
aattaaattg tttttatacg gtgggtagag gggaattgat ttaggtttgg aataagagag    1440
aatattttaa ttgaaaagtt tttggaattc gttgaatttt aagatattgt gtggattagt    1500
ttaggatagg gagtgagaag aaattaatta aaaggtaatt tcgttatttt ttagttggaa    1560
aaaagattag attatatttg tgtttttata attaagtagt tgttggaaaa aaacgtttta    1620
gatgtttttt atgagaaaat tgttgtttga agtttagtag aagttattta tttgatattt    1680
atattttagg taaggttttt cgttggagaa aatatcggta ttttggataa aattgaaatg    1740
tgaaaagaaa gggaagagag ggttttttatt atgtaagatg tttatttaaa gtggatttgg   1800
tttgaaaagt tttttaaaat tttttatatg attgtggaat aagttatgtg gggcgcgggg    1860
ataagcgaat ttttaaaatt ttattacgta tgttttatt taatttggat ttttagagtg     1920
gttttagggg tattttgttt aggatttagt tagttgttgg ttatatttat gttttttagt    1980
tttttgagat tttatttggt tttgagaggg ttaaaaagta gtgtggttaa atattttagg    2040
ttttaaagta ttttttattgt ggttggggaa gtaatagaat tatattttat aaaataatga   2100
aaatagtgtt agaaaatat cgagagatag aaatattttt acgagttagg ttatagttag     2160
agtgaaggta gggaaggttt ttaaagttgg gtggagggga taagttaaaa agatgtggaa    2220
attggttttt tttttttatg gttaaagtgt ttaaagggga aaaaggagtt ttaaaaatgt    2280
ttttggaaat attatttttt acgaattttt cggttttgt tgttttaatg ttatttgttt     2340
gagatgtaaa tagaggagtt ttgagaaaga agttgaattt gtattttttt ttgtttttat    2400
ttgttttaaa tttgtggtat ttttaatagg atgaagcgga agagaaaggg aaagagataa    2460
aagtgtagaa agatggaaga tttagttgt aaatggttat ttgtagttag atggaatagt     2520
tgttgacgtt tagggaaatg tatgtttttt tttgatgggg aaggagtagt ggaaggggt     2580 gacgagtttt tggttggtta ttaattattt tatttttttg tgtcggtttt ttatttggaa    2640
agtgggagtg atatttgtgt ttgtttttt tatttataaa gattattgtg agagttataa     2700
tacggtgaga tatagaattt tgtttttaaa aatataaagt agaattaaga tgttaataat    2760
aaggatagta attgtgttag ttatttgtaa ttatttatta tagttagtcg tttaggattt    2820
tggatcgttt tttggtttt attatagttt tggattagtt tatttttaaa tttttgttg     2880 aagggtggag ttttgttagt tatgggtagg gaattatttt tttttgtttt tttatttttt    2940
```

```
gtttttaaaa tatgtttagg gttttttgtat ttgttgtttt ttttgtttgg tattttttttt   3000 ttgtggtttg ttttagagtt gattttttgtt tttgtttatt ttttagcgag gatggtattt   3060
tagggagttt ttttttttatt atcgtagaga gagtaggttt tttttagtta tgtttaattt   3120
agaattttgt tttgttttttt ttatagtttt agtattatag aaaattattt tgtgtattta   3180
tggatgttta cggggtaag ggttttgtgt tgtttaattt agtattttga atcgtgtttg   3240
ttgaatgaat atagaatttc gtttgttttg ggagagtata gaaaatagtt ttttattata   3300
tattatagtt agttgtaaat agtagatggt ttttatatt ttagagagta agaattagag   3360
agagagagaa agagagagag tttgggtttt tttttttgt gtttgttttt tttagagaaa   3420
ttggaggggt agtagttagt atttttcgt tggttttatt aagtatagtt aaggttttta   3480
ggatatggtt atttttttatt tgtggaagcg gttttgttgg ggtgggtggg tgttagttgg   3540
ttttggtttg ggttagagat atttagtggt ttaggtgggc gtggggttag ggcgtagacg   3600
agaagggata cgagggtttc gtttcgagga tttagcggta agtatcggtt tcgggcgcgt   3660
tttagtttat ttattcgcgt gtttacggcg gtattatttt ttataaggat ttgaacgatt   3720
cgggggcggt ttcgtttcgt tatttttgt tttcggtttc gttttttttt tggagggtcg   3780
atgaggtaat gcggttttgt tattggtttg aggggcggg ttttaatagt tcgaggcggg   3840
gttttcgggg gtttagcgtt atattattcg gtcgttagg tagcggcgta gagcgggtag   3900
taggtaggcg gcgggcgttt agacggtttt tttttttttt tttgttttt tagttttttgt   3960 tttttcgtcg ggaggtcgtt cgtcgagttt tgcgttagcg tcgaggtagt ttcgttgcgt   4020
tttatttcgt ttcgtcgggt attcggaggg tagcgcgtcg gaggttaagg ttgtttcgta   4080
cggttcggcg ggcgagcgag ttcggggttgt agtagtttcg tcggcggcgc gtacggtaat   4140
tttggagagg cgagtagtag tttcggtagc ggcggtagta gcggtaatga tttttttggtt   4200 cgggtttatc gtgttttttgg gtagttggag tttgggggat tggggcgtcg aggcgtgtat   4260
atgttcgttt agttattttt aggacgtttt ttgtaatttc gatatcggta agcgtttttg   4320
gtgtttcgtt cgagttttac gttgtagtta ggattgtagc gttgtttagg gaggtagggc   4380
gagttttatt tttttttttt gttttaggag agggtagac ggggttgggg cggagtggag   4440
aaattcgatg ttttttgggcg ggggcgttgg tatagttgag aggggaagat gttttgtaga   4500
g                                                                  4501
```

<210> SEQ ID NO 51
<211> LENGTH: 4501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 51

```
ttttgtaggg tattttttttt ttttagttat gttagcgttt tcgtttaagg atatcgagtt     60 ttttttatttc gttttaattt cgtttgtttt tttttggggg tagaggaaag gagtgggtt    120 cgttttgttt ttttaagtag cgttgtagtt ttggttgtag cgtggggttc gggcggggta    180
ttaggagcgt ttatcgatgt cggagttgta gaaggcgttt tggggtggt tgggcgagta    240 tgtgtacgtt tcggcgtttt agttttttag gtttagttg tttaggagta cgatgagttc    300
gagttaaggg gttattgtcg ttgttgtcgt cgttgtcggg gttgttgttc gtttttttaa   360
agttgtcgtg cgcgtcgtcg gcggggttgt tgtagttcga gttcgttcgt tcgtcgggtc    420
gtgcggggta attttggttt tcggcgcgtt gttttttcgag tgttcggcgg gacgggatgg   480
```

```
ggcgtagcga ggttgtttcg gcgttggcgt aggattcggc gggcggtttt tcggcgaagg    540
agtaggagtt ggaggagtaa gaggaggagg agaagtcgtt tgagcgttcg tcgtttgttt    600
gttgttcgtt ttgcgtcgtt gtttgggcgg tcgagtgata tagcgttggg ttttcgggga    660
tttcgtttcg ggttgttggg gttcgttttt ttagattaat ggtagagtcg tattatttta    720
tcggtttttt aaaaagggggg cggggtcggg ggtaaggggt aacgggcgg ggtcgttttc    780 ggatcgttta gattttttata gggaataatg tcgtcgtggg tacgcgagtg ggtgggttgg    840
ggcgcgttcg ggatcggtgt ttgtcgttgg gttttcggag cggagttttc gtgttttttt    900
tcgtttgcgt tttggtttta cgtttatttg ggttattggg tgttttttgat ttaaattaga    960 attaattaat atttatttat tttagtagga tcgtttttat aggtgagggg tggttatgtt   1020
ttagagattt tgattgtgtt tggtggaatt agcgggggaa tgttaattgt tatttttta   1080 gttttttttgg agagagtagg tatagaggag aaagatttaa attttttttt tttttttttt   1140
tttttggttt ttattttttg ggatatggga agttatttgt tgtttgtagt tggttatgat   1200
atatgataga agattgtttt ttgtgttttt ttagagtaaa cggggttttg tatttattta   1260
ataaatacgg tttaggatgt tgggttaagt aatataaagt ttttgttttc gtggatattt   1320
atgaatgtat agggtgattt tttgtgatgt tagggttatg aagaaaataa aatagagttt   1380
tgggttggat atgattgggg agggtttgtt tttttttgcga tagtaaggga agggttttt    1440 gaagtgttat tttcgttgag aagtggataa agataaggat tagttttggg gtaagttata   1500
ggagagaggt attaggtagg gggaatagta agtgtaaaga ttttgggtat gtttgaaaga   1560
tagaaagtag aaaggtaaga ggaagtggtt ttttgtttat ggttgataga gttttatttt   1620
ttagtaaggg atttggggggt gagttgattt aaaattgtag taaaattagg agaacgattt   1680
aggattttag acgattagtt ataatagatg attgtagata attaatataa ttattatttt   1740
tattattgat attttgattt tgttttgtat ttttaaaagt aggattttgt attttatcgt   1800
attatagttt ttataataat ttttgtgggt aggaaaagta agtataagta ttatttttat   1860
tttttagatg aggaatcggt atagaaagat gggatgattg gtggttagtt aggaattcgt   1920 tattttttt tattgttttt tttatttga agagagatat gtattttttt gaacgttagt   1980
agttgtttta tttaattgta aatggttatt tgtagttggg atttttttatt tttttatatt   2040 tttgttttt tttttttttt tttcgttttta ttttgttaga atgttataa gtttggaata   2100 aatagaaata gggagaaatg taagtttagt tttttttta gaatttttt gtttatattt   2160 tagataagta atattgggat agtagaggtc gaagaattcg tgagagatgg tatttttaag   2220 aatattttttg aaattttttt tttttttttg agtatttag ttataggaaa gggaaattag   2280
tttttatatt ttttgatttt gttttttta ttagttttta aaaattttt ttgttttat   2340 tttaattgtg gtttaattcg tagagatgtt tttgttttttc gatgttttttt tagtattgtt   2400 tttattgttt tatggggtat gattttattg ttttttaat tatagtagga atattttgag   2460
gtttgggata tttagttata ttgttttttta gttttttag aattaaatag ggttttagga   2520
gattggagag tatgggtgtg gttaatagtt gattgagttt tgagtagagt gttttggagg   2580 ttatttaag gatttaggtt gaatgagggt atacgtggtg gaatttgaga gattcgttta   2640
ttttcgcgtt ttatatgatt tattttatag ttatgtggaa ggttttagaa gatttttag   2700 attaaattta ttttggataa gtattttata tgatagaggt ttttttttt ttttttttt   2760 atattttagt tttgttaaa gtgtcgatat tttttttaac ggaaggtttt gtttggaata   2820
taagtattaa gtagataatt tttgttgaat tttaagtagt agttttttta tagaaagtat   2880
```

-continued

```
ttgaagcgtt ttttttttagt agttatttaa ttatgaaagt ataagtataa tttgatttt      2940 ttttagttg aaaagtaacg aaattatttt ttggttaatt ttttttatt ttttatttta      3000 agttggttta tatagtgttt tgaagtttag cgaattttaa gagtttttta gttgggatgt      3060 ttttttat tttaaatttg agttagtttt ttttgttta tcgtgtgaag gtagtttggt      3120
ttttatttta aggaaaagaa atagtaaatt ttatgaattt ttgcgtaggg gagttttttt      3180
gttagggtta tttttttag taggtattta ttagtttgga tgttatggtg tttatgagtt      3240
taataatatg taagaattgg ttatttaata ttatttaata agttaggtgg ggtgaatttg      3300
aggttaatag taagaatgaa gatgtaggtt gggtgcggtg gtttacgttt gtaattttag      3360
tattttgaga ggttaaggtg ggcggattac gaggttagga gatcgagatt attttggtta      3420
atatggtgaa atttcgtttg tattaataat ataaaaaatt agttaggtgt ggtggtgggc      3480
gtttgtagtt ttagttatt gggaggttga ggtaggagaa tggcgtgaat tgggaggcg      3540 gagtttgtag tgagttgaga ttatgttatt gtattttagt ttaggtgatg gagtgagatt      3600 tcgttttaa aaaaaaaaa aaaaaaaaa agaatgaaga tgtaggtttt tttgttttt      3660 tttgatagtt aagaataatg atagagttat atatttggga agaattgagt aagttttaag      3720
atttatttgg tttgtttata tatttattag gatgatttgg tattttttt tttggaattt      3780 ttttaggaaa ggtgagttta tattattttt ttttgtatta agttatagga tgttagagtt      3840
tgtaggaaga gaagtcgtaa aaaggatttt agaaattatt tattttttgtt ttaaatgtgg      3900 gaaaaataag gttagagaa gtgaaggaat tgtttattt ttagggtta gtttttaag      3960 ttgtaaggtg tggtttatgt ttgtattgtg ggtttggaaa tttagttat ttatagattt      4020 cgtatttgtt ttttagattt gtagatagat tcgtttgagt ttttgtatag tgtttagttt      4080
atagagaaat ttatttata ttgattaaat aatttttat tatgataata attatttttt      4140
gagttaatta gaagtaatat aggtttgttt ttttgatagg tttatttttt gtgtgtttat      4200 tttttttt ttttaaatta ttagttaatg tatttttaaat atattattat aaaaaaaagt      4260
atatgaaaat tttgttttg ggaaatgaaa agagagtaaa gtggaaataa aaaattaaaa      4320
gatttgagat ttgttttaa tgttgtagaa tagttgtgta tttgttttgg ttaagttatt      4380
ttgtttgttt aggcgtttat ttttgtgttt attggatgaa agatagaatt tagtggtatt      4440
taggattttt ttcgttttaa aaatttaag attttatggg gaattttgta ggataagtga      4500
a                                                                     4501
```

<210> SEQ ID NO 52
<211> LENGTH: 3001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 52

```
gaagtgttaa tgttagattt ttatttatta tataagttta ttttgtatt agggtagtga       60 ttttttttt tgggtgagat tttgaaattt gggattataa ttttgaatta taattataaa      120
atggtatttg gttgtaaatt atttttttt ttttttgtt tttatagtt gatattatgg      180 atttttataa ggatttatgt tttttatta ttttaatgaa tagttgttgg gtaataattt      240
tagaagagtt ttaatttta ttaggagaat ggataaggtg gagaagtaga gaaaatgtaa      300
tgagtagaat gtttaagtta ttattttgga attgattgaa tataaataaa aatgagaaag      360
atacgtaaaa aagaagggaa tgggtaagta gggtgatgtt tgggagagga ggggttttat      420
```

-continued

```
agttatgaga gttaattttg taatatttta tagggttata atattgtttt ttatatattg    480
aggtagtagt agggaaattt tttaattatt agaaatattg aattttgttt tttatttta    540 aatatttttt ttatttagtt tttgttttt tttattttg taatttttat tgttttaaaa    600 atgattttt ttttttcgga agaagtaatt tttaaattt agtttatata aggggatttg    660
atatgtttaa taagttttaa atatattgta tttagtaata tttattatat gtttattttg    720
agttttgagt aatttgtatt ttaagtttag tttttattgt tttgttttg gtaaattttt    780 attaagtgtt tttttttt aaatatacgt atatgtttat tagattttaa agttttttat    840
gaatatgtaa atttttttt tttgaaaatt tttgcgtgag tggttagtag gttaattat    900 ttattgtaat gtggttttgt gttagggttt tgttttcgtg ttgtttgtaa gataattata    960
gatgtgattg tattttagaa gtttttgaat tttttaagat agtttggttt ataagaaaat   1020
taaaaggtgg aggtcgggcg cggtggttta cgtttgtaat tttagtattt tgggaggtcg   1080
aggcgggcgg attatttgag gttgggagtt cgaaattagt ttgattaata tggggaaatt   1140 tcgttttgt taaaaatata aaattagtta ggcgtggtgg tgtatgtttg taattttagt   1200
tattcgggag gttgaggtag gagaatcgtt tgaattcggg aggtagaggt tgcgatgagt   1260
cgagatcgtg ttattgtatt ttagtttggg taataagagc gaaattttgt tatatatata   1320
taaatatata tatatatata tatacggtgt agtttaggaa gtaaaaaaaa aaaaaaaa    1380 aaaattagat ttttttttat attttagatt tgaaggtata aattttaggg ttagggcgtt   1440
cgtttattta atttatatg tatttgtagg ttatttagta tttaggtatt tagtatttag   1500
gtatattgtg gttttttatt tttacgata gtagtaataa cgttgattgg aagtttatta   1560
ttgtgtgtta cgggttatgg gttatgtgtg ttagaatttt atgtgaaatt aatatttaat   1620
ttttacggat atttttgaaa tagatgttat agttttatt ttgttaacga ggtagttgag   1680
gtttttagag gtttaatatt agtattatga gtcgtagtac gtaaggtaaa tatagtcgga   1740
ggtgagtata tatttgtttc gtattttatg cgtttaatta taaggttttt ttttttag    1800 aaggtcgttg tttttttgg gacgattgt tagttttgag gtatgatagt acgggttttt   1860
agaagggtga ttaggaggtt tttttcgttt tagttgtcgg cgtcgtcgtt tattgtaggg   1920
ttcgggttgt gattcgtggg gacggttttt tgcgtttcgg cggggaggt gggcggggag    1980 gggcggcggg gcgtcgggc ggggttcggg acgtcgggt tggagttgg agtttatagc     2040 gggaagcggt cgtcgttcgg gtttcgtagg gttaggcgag gcgaggggg gcggggtcgg   2100 gcgttacggg aaggggaggt cgcgcggatc gggagtcgta tcgcgttagt cgggttgtag   2160
cggtcgcgta ttaaggttgc gatggggttg gagacggaga aggcggacgt atagttttt   2220 atggacgacg atttttatag ttattatagc ggtttcgagt acgtcgattt cgagaagttc   2280
gcggattcgg attaggatcg ggattttat cggtttaatt cgtattttaa ggtgaagttc   2340
ggggcgggcg ggtttaagtt ttcgttgagg tcgggaggtg cgggcgtttt ttagtttcgt   2400
tttaattcgt tttattattg ttatcgggtc ggtttcgtag ggtttgagat tcgtattttt   2460
tttcggtttt attcgttatt aggtcgttcg cgtagttagg aatttttagt taggttttg    2520 tgcgtttatc gtgattttaa gagaagaggc ggacgttttg gtacgtttt ttttttgtt    2580 tttttcgttt aaagcgtttt cggttttcgg ggcgttaggt tggttgatag ttcggggttt   2640
ttgcgttttg ttttttagt tgggtttcga ggatgtgatc gtagagtcgg tgattacgta   2700
tttttttgat aaagtgtgga tttgtagtta tgtttttttt gaaattagta aatacgtaat   2760
gtataagttt ttgacggtgt ttttggttat ttttttggtt tttattgcgg gaattttttt   2820
```

-continued

```
tgttattttt agttgtttgt atatttggtg agacggggta tatcggtggg atcggttttt      2880
tgaaatatgg gtatattttt cgttatttgt tttttatttt tttttttattt taggtcggcg      2940 ttaggaggag gaacgcgtat tagttttaa gtagtaggaa gaattggaag gttttgaaag        3000
g                                                                      3001

<210> SEQ ID NO 53
<211> LENGTH: 3001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 53 tttttttaagg ttttttagtt tttttattg tttgggaatt gatgcgcgtt ttttttttg         60 acgtcggttt gggataagag gagagtaggg ggtaggtggc ggagaatatg tttatgtttt       120
agaaagtcgg tttattcggt gtgtttcgtt ttattagatg tgtagatagt tgagggtggt      180
aaagagaatt ttcgtaatga aggttagggg aatggttagg aatatcgtta ggaatttgta      240
tattacgtat ttgttgattt taaagagggg atggttgtag atttatattt tgttaaagga      300
gtgcgtagtt atcggttttg cgattatatt ttcgaagttt agttgaggag ataggacgta      360
gggatttcga attgttagtt aatttgacgt ttcgggaatc gggagcgttt tgggcggggg      420
aagtaggagg gaaggacgtg ttagggcgtt cgttttttt tttagggtta cggtgggcgt       480
ataggaattt ggttaagaat tttttggttac gcggcggtt tggtgacggg tgggatcggg      540
gaagggtgcg ggttttagat tttgcggggt cgattcggta gtaatggtgg gacgggttag      600
ggcggggttg aggggcgttc gtattttcg gttttagcgg ggatttgggt tcgttcgttt       660
cgggttttat tttgagatgc gagttgagtc ggtgggatt tcggtttgg ttcgagttcg        720 cgaattttc ggggtcggcg tattcgaggt cgttgtggtg gttgtaggag tcgtcgttta       780
tgaagagttg tacgttcgtt tttttcgttt ttagttttat cgtagttttg gtgcgcggtc      840
gttgtagttc ggttggcgcg gtgcggtttt cggttcgcgc ggttttttt tttcgtagcg      900 ttcggtttcg ttttttttcg tttcgtttag ttttgcgagg ttcgggcggc ggtcgttttt      960
cgttgtgggt tttagttttt agttcggtcg tttcgagttt cgtttcggcg tttcgtcgtt     1020
ttttttcgtt tatttttttc gtcggggcgt agggaatcgt tttacgagt tatagttcgg      1080 gttttgtagt gggcggcgac gtcggtagtt gggacgagga gggttttttg gttatttttt     1140
tgggggttcg tattgttatg ttttagagtt ggtaagtcgt tttagggaag ataacggttt     1200
ttttggaggg agggaatttt gtggttaggc gtatggggtg cgaagtaggt atgtgtttat     1260
tttcggttgt gtttgttttg cgtgttgcgg tttatggtgt tggtattgag ttttgggaa     1320 ttttagttgt tcgttggta aaatggggt tgtggtattt gttttagggg tgttcgtgag      1380
aattaaatgt taattttata taaaatttta atatatatgg tttatggttc gtaatatata     1440 gtgataaaatt tttaattaac gttgttgttg ttgtcgtgag aggtaaggag ttataatgta    1500
tttgagtgtt aggtatttga gtgttaggtg atttgtaagt gtatgtggag ttgggtaggc    1560
gaacgttttg gttttagagt ttgtgttttt agatttgagg tgtgagggga gatttgatt      1620 tttttttttt tttttttta tttttaaat tatatcgtgt gtgtgtgtgt gtgtgtgttt      1680
gtgtgtgtgt ggtagagttt cgttttttgtt gtttaggttg gagtgtaatg gtacgatttc    1740
ggtttatcgt aatttttgtt tttcgggttt aagcgatttt tttgttttag tttttcgagt     1800
agttgggatt ataggtatgt attattacgt ttggttaatt ttgtattttt agtagagacg     1860
```

```
gggtttttttt atgttggtta ggttggtttc gaattttttaa ttttaggtga ttcgttcgtt    1920
tcggtttttt aaagtgttgg gattgtaggc gtgagttatc gcgttcgatt tttattttt     1980 aatttttttg tgaattagat tgttttgaaa gatttaggaa ttttttaagat gtagttatat   2040 ttgtgattat tttgtaggta gtacggaaat agaattttaa tataaagtta tattgtaatg   2100
gatgaattag tttgttgatt atttacgtaa aggtttttag aagggaggag tttgtatgtt   2160
tataaagggt tttagggttt ggtagatata tacgtgtgtt tggggaggaa gggtattag     2220 tgaaaatttg ttaaaagtaa aataatgaga attaggtttg aggtgtaggt tgtttagagt   2280
ttaaagtagg tatgtagtag gtattgttgg atatagtgta tttggagttt gttgaatata   2340 ttaaatttt ttatgtgaat tggatttgaa gaattgtttt tttcgaaaga aaaagatta    2400 tttttgaaat agtaaaaatt atagaaataa aaagaatag gaattgaatg agaaaaatgt    2460
ttgggggtgg gaggtaaagt ttaatatttt taataattaa aaagtttttt tgttgttatt   2520
ttagtatatg aagggtagtg ttgtaatttt atagggtgtt atagagttga tttttatggt   2580
tatggagttt ttttttttt agatattatt ttgtttattt atttttttt ttttacgta      2640 tttttttat tttatttat gtttagttaa ttttaaagtg atgatttaga tatttttattt    2700 attgtatttt tttttttt ttatttttgtt tattttttg atgagaattg gaattttttt    2760
agaattgttg tttaataatt gtttattaaa gtgaatagaa gatatgaatt tttatgggaa   2820
tttataatat taattgtgag gaatagaaaa aaaaaggaga taatttatag ttaaatatta   2880
ttttataatt ataatttaaa attataattt tagatttaa ggttttattt aaagaagaaa    2940
gttattgttt tagtataaga gtgggtttat gtagtgggta aaaatttgat attagtatt    3000 t                                                                    3001

<210> SEQ ID NO 54
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 54
tttggatttt aatgtgtatt ttatatttat agtataatta atttgggatt agttatattt      60
tagtttaata atagttaata gtatatggga tagtgtaaat aaattttgtg ttttttgttgt    120 tttttttgggt tttggagatt ttaattttt ttttagattg taaattttt tgttttttaag     180 ttttggtttt aatattagtt tggtagagga atttagttta atgaggtatg tttttttttt    240
gttatttttt attttattaa tttgttttgt ggtaaatgta ggattgattt tttaaaatta    300 tttattaat tagtttatat atttattatt tatttgtttt attagaatgt aggttttgg     360 aaggtaggga tttaaaaaaa tttgttttgt tttatgtgat ttttttatat taagtattgt    420
gtttggtata agttgggatt ttagtatata ttttgggatg gaagaattgt gttttttag     480 aatttagtta gagggtagtt tagtaatgtg ttataggtgg ggtgtttgtg ttttgggtgg   540
atgtattggt tttttggttg gtgtgggtgt ggggtgagtg ggtgtgtgtg ggtgtgtgt   600 ggtagagtgt gttagtgagt ttggagtgtg gagttgggag gagtagtgag tgttgtgtag   660
aatttgtagt gttggtttgg tagggtagtt tggaggtggg tggttgtgt tgttagtttg   720 tttgtagggt tttattggt tgtttgttgg ttgttttttg tttaaaaggt ggtaaggagt   780
tgagaggttg ttttggagtg tgaggaggat agttggattg agttaatgtt ggggattttg   840
ttttttttgt ggaggggatt tggtaatttg tagtggtagg gtttggggtt ggtgtttggg   900
```

| | |
|---|---:|
| agggatttgt gtttttatt tatttttag ttgtgtttt gttgttgttt tggttagttt | 960 |
| ttggtgttgg tgtttatggt tggttttga tagtgttttg gagggattgg gggagtttt | 1020 |
| aggtgtttgg gtgagtagtt aggtgtggtt ttttggtttt tttgattttt ggtgttagtt | 1080 |
| tttgttttt tagttagggt gtggtggggt ttgtttgggt agtgttttga gtaattggga | 1140 |
| aggttaaggt ggagggaaat tggttttgg ggagaagtgt gattgtagtt gggaggtttt | 1200 |
| tttagttttg tgggttgggt gagaataggg ggtgttggt tgattaggtg ttttgtgttg | 1260 |
| gggtgtgagg atttggagtg aattgttgtg ttttggtggg ttgtttttt tttttttg | 1320 |
| tttttttggg tggttgtatg ttgggttggt tgggtaatgg agagggagtt gttaggaatg | 1380 |
| tggttttggg gattgttttg tttggggaag gggagagggt ggttatggtg ttaggagagg | 1440 |
| tgtgggagtt gagaggtggt gtgggggtgt tattgttgtt gtaggttgga gagagattgt | 1500 |
| ttttagtgag gtgtgtattg tttgggtgag ggttttattt ttttgtggtg tttttggagg | 1560 |
| tgggaaagtt gggtgggtat gtgtgtagag aaagggagg tggggaggtt agttattttt | 1620 |
| ggagttggtt ttgatttaa tagattgttt agtgtttggg gatgttgatt ttgggtgtt | 1680 |
| gtggtgtttg gttttatgtg tgtgtggggt tgagggggtg ggggtgtttt tggttgttta | 1740 |
| gttttaataa agggtgtttt tttttatttt gtgaggaggg gtagttttgg agatttggtt | 1800 |
| tttagtgagt ggggttttag tgttgggag gtttattttt ttttgggtt gttatttat | 1860 |
| tattattatt gttttttt ttttttaaa aggattggag attgatgtat gaggggtta | 1920 |
| tggaggtgta ggagtggtgg tgatggttg ggaagtggag ttgaagtgtt ttgggttttg | 1980 |
| gtgaggtgtg atagtttatt atgattgtgt ttaggtagga aaatgtggat gattattatg | 2040 |
| atattggtga ggaatttggt aggtaaaggg ggtattagaa gtgtattttt ttggattgtg | 2100 |
| gaaatgtata atgatggggt tattgggtgg taaataaatg tagtttgaat taggtgtttt | 2160 |
| tttgttttt tttggagatg tgtaaattat agagaaaaga gttattaatt tagtggtaaa | 2220 |
| ttgtttgatt taagggtttg ggggtggagg agaggtagta gtttagggtt agattatgat | 2280 |
| gtatagtata ttgatttagt ttttggata aaattagatt taattgtttg tgttaattt | 2340 |
| tgttagtttt tgtttttg tgataatagg ataaatatta agattataat tgtaattgga | 2400 |
| gttagttttt atgtgtgatt taaatggagg gtataaatta attaataggt tttaaaaatt | 2460 |
| ttagtatttt attttttatt taaatttta gtgtaatttg a | 2501 |

<210> SEQ ID NO 55
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 55

| | |
|---|---:|
| ttaaattata ttgaaaattt agatagaggg taaagtatta agatttttaa aatttattaa | 60 |
| ttagtttgta tttttttgttt aaattatata taaaagttaa ttttaattgt aattataatt | 120 |
| ttagtgtttg ttttgttgtt atagaagggt aagggttgat aagagttagt atggataatt | 180 |
| aaatttgatt ttgtttaggg gattggatta atatattgtg tattataatt tagttttgaa | 240 |
| tgttgttttt tttttatttt ttaggttttt ggattaggtg gtttattgtt gggttagtaa | 300 |
| ttttttttt tatgatttgt gtatttttag aaagggtgag ggagatgttt gatttaaatt | 360 |
| gtatttgttt attatttaat ggttttattg ttatgtattt ttataattta ggagggtatg | 420 |

```
tttttggtat ttttttttatt tgttaagttt tttgttggtg ttgtagtaat tatttatgtt    480
tttttgtttg aatatggtta tgataaattg ttatgtttta ttaaagttta gggtattta     540 gttttgtttt ttagattatt attattgttt ttgtgttttt gtagttttt tatgtattag     600 tttttagttt ttttgaagaa aaaaaaagg taataataat agtaaaatgg taattttaaa     660
aggaagtaga ttttttggt gttaagattt tgtttgttga agattgggtt tttggagttg     720 ttttttttg tggggtggag aggagtattt tttgttaaag ttgggtggtt agggatgttt     780 ttgattttt agtttgtgt gtgtgtgggg ttgggtatta tggtattttg aggttggtgt     840
ttttaaatgt tgggtggttt gttgggatta gaattggttt tggaagtgat tggtttttt     900 gttttttttt ttttgtata tatgtttatt tagtttttt attttaggg atgttgtgga     960 agaatgaagt ttttgtttag atggtatgtg tttattggg agtaatttt tttagtttg    1020 tggtaatggt ggtattttg tgttatttt tggttttgt gttttttta atattgtggt    1080 tatttttttt ttttttttga gtgaggtagt tttagagtt atattttgg tgattttttt    1140 tttgttattt ggttgatttg gtgtgtggtt gtttggggga gtaagggagg gaagggagtg    1200
gtttattgag gtgtagtagt ttgttttaga ttttgtgtt ttgatataaa gtgtttggtt    1260
gggttggtgt tatttgtttt tatttggttt gtggggttgg ggaagtttt tggttgtgat    1320 tgtattttt tttgaagtta agtttttttt tgttttggtt ttttagttg tttgaggtat    1380 tgtttggata aattttattg tgttttggtt gggaaagtaa aagttggtgt tggggttgg    1440 ggggattggg gagttgtgtt tggttattta tttgggtgtt tgggagtttt tttggttttt    1500
ttggagtgtt gttggaggtt gattataggt gttagtgttg gagattagtt ggggtggtgg    1560
tgggaatata gttagggagt gagtgggggg tgtagatttt ttttaggtgt tggttttaga    1620
ttttgttgtt gtgagttgtt gagttttttt tgtggaggga ataaagtttt tggtgttggt    1680
ttggtttggt tgttttttt atattttgaa gtagttttt ggtttttgt tgttttttgg    1740 gtggagggtg gttggtaggt ggttaatggg gattttgtaa gtgggttggt ggtgtggttt    1800
atttattttt gagttgtttt gttaggttgg tgttgtgggt tttgtgtggt gtttgttgtt    1860 tttttagtt ttgtgtttg ggtttgttgg tgtgttttat tgtgtatatt ttgtatatat    1920
ttatttgttt tatatttatg ttggttgggg agttagtgtg tttgtttgga atgtgggtgt    1980
tttatttgtg atatattgtt aagttgtttt ttgattgggt tttagggaaa tatggttttt    2040
ttgttttgag atgtgtattg ggattttagt ttgtgttggg tatggtgttt ggtatgggaa    2100
aattatatag aataaaatag atttttttaa attttgtttt tttggaaatt tgtattttgg    2160
tgggatagat agataataaa tatgtaagtt aattaataag gtaattttgg aggattagtt    2220
ttatgtttat tatgaaatag gttaatggaa tagagaatgg taggaaggga gtgtattta     2280 ttagattggg ttttttgtt ggattggtgt tggagttgag gtttgaaggt aagaaggttt    2340
gtaatttgaa gaaagggttg aggttttga gatttaaaga agtaatagag atgtagagtt    2400
tatttgtgtt attttatatg ttattggtta ttgttgagtt gaaatgtagt tagttttaaa    2460
ttaattgtgt tgtaagtgta aaatatatat tagagtttaa g                       2501
```

<210> SEQ ID NO 56
<211> LENGTH: 4501
<212> TYPE: DNA
<213> ORGANISM: Artificial Sequence
<220> FEATURE:
<223> OTHER INFORMATION: chemically treated genomic DNA (Homo sapiens)

```
<400> SEQUENCE: 56
tttatttgtt ttataggatt ttttatggaa ttttggagtt tttgaggtga gagggatttt      60
ggatattatt gagttttatt ttttatttaa taaatataga agtggatgtt tggataggta     120
aagtgatttg attaaggtag gtgtatagtt attttgtaat attgggaata aattttaggt     180
tttttgattt tttgttttta ttttattttt tttttatttt ttagaaataa agttttatg      240
tgtttttttt tatagtgata tgtttggaat gtattagtta gtaatttagg aagggaaaaa     300
aataaatata taagagataa atttgttagg aggataaatt tgtattgttt ttgattggtt     360
tagagggtga ttattattat ggtagagaat tatttaatta gtgtaagtaa aattttttg      420
tgggttgggt attgtataaa gatttaaatg aatttgttta tagatttgaa aagtagatat     480
gagatttgtg aatggttggg gttttttaagt ttatagtata agtatgggtt atattttata     540
gtttggagga ttgagttttg aaaatgggta agttttttta ttttttttgaa ttttattttt     600
tttatattta aaataaggat gagtagtttt tgaggttttt tttatgatttt ttttttttat     660
agattttagt atttttataat ttgatataaa gagggtggat atgaatttat tttttttaga    720
aaagttttag gaaagagaat attaggttat tttagtaggt gtgtagatag gttagataga     780
ttttgaaatt tatttagttt tttttagatg tataatttta ttattgtttt tagttgttaa     840
gagaaagtag gagagtttgt attttatttt tttttttttt tttttttttt tttggagatg     900
gagttttatt ttattattta ggttagagtg tagtggtatg attttagtttt attgtaagtt    960
ttgtttttta ggtttatgtt attttttttgt tttagttttt taagtaattg ggattatagg   1020
tgtttattat tatatttggt taatttttttg tgttgttagt atagatgggg ttttattatg   1080
ttagttagga tggttttgat ttttttgattt tgtgatttgt ttattttggt tttttaaagt   1140
gttgggatta taggtgtgag ttattgtatt tagtttgtat ttttattttt attgttagtt   1200
ttaggtttat tttatttagt ttattaagtg atgttgaata attaatttttt atatattatt   1260
aggtttatgg atattatgat atttagattg atgggtgttt gttgaagggg gtgatttag     1320
taggaggatt tttttatgta aggatttatg gagtttgttg ttttttttttt ttagggtgag   1380
aattaaattg tttttatatg gtgggtagag gggaattgat ttaggtttgg aataagagag   1440
aatattttaa ttgaaaagtt tttggaattt gttgaatttt aagatattgt gtggattagt    1500
ttaggatagg gagtgagaag aaattaatta aaaggtaatt tgttattttt ttagttggaa    1560
aaaagattag attatatttg tgttttata attaagtagt tgttggaaaa aaatgtttta    1620
gatgtttttt atgagaaaat tgttgtttga agtttagtag aagttattta tttgatattt    1680
atattttagg taaggttttt tgttggagaa atattggta ttttggataa aattgaaatg     1740
tgaaaagaaa gggaagagag ggttttttatt atgtaagatg tttattaaaa gtggatttgg   1800
tttggaaagt tttttaaaat ttttttatatg attgtggaat aagttatgtg gggtgtgggg   1860
ataagtgaat tttttaaatt ttattatgta tgttttttatt taatttggat ttttagagtg   1920
gtttttaggg tatttttgttt aggatttagt tagttgttgg ttatatttat gttttttagt   1980
tttttgagat tttatttggt tttgagaggg ttaaaagta gtgtggttaa atattttagg     2040
ttttaaagta tttttattgt ggttgggaa gtaatgaaat tatattttat aaaataatga    2100
aaatagtgtt agaaaatat tgagagatag aaatatttt atgagttagg ttatagttag     2160
agtgaaggta gggaaggttt ttaaagtttggg gtggagggga taagttaaaa agatgtggaa   2220
attggttttt tttttttatg gttaaagtgt ttaaagggga aaaaggagtt ttaaaaatgt   2280
ttttggaaat attattttttt atgaattttt tggttttttgt tgttttaatg ttatttgttt   2340
```

```
gagatgtaaa tagaggagtt ttgagaaaga agttgaattt gtattttttt ttgtttttat    2400
ttgttttaaa tttgtggtat ttttaatagg atgaagtgga agagaaaggg aaagagataa    2460
aagtgtagaa agatggaaga tttagttgt aaatggttat ttgtagttag atggaatagt     2520
tgttgatgtt tagggaaatg tatgttttt tttagatggg aaggagtagt ggaaaggggt     2580
gatgagtttt tggttggtta ttaattattt tattttttg tgttggtttt ttatttggaa     2640
agtgggagtg atatttgtgt ttgttttttt tatttataaa gattattgtg agagttataa    2700
tatggtgaga tatagaattt tgttttaaa aatataaagt agaattaaga tgttaataat     2760
aaggatagta attgtgttag ttatttgtaa ttatttatta tagttagttg tttaggattt    2820
tggattgttt ttttggtttt attatagttt tggattagtt tatttttaaa tttttttgttg  2880 aagggtggag ttttgttagt tatgggtagg gaattatttt tttttgtttt tttattttt    2940 gttttttaaa tatgtttagg gttttgtat ttgttgtttt ttttgtttgg tatttttttt    3000
ttgtggtttg ttttagagtt gattttgtt tttgtttatt tttagtgag atggtatt       3060 tagggagttt tttttttatt attgtagaga gagtaggttt ttttagtta tgtttaattt   3120 agaattttgt tttgtttttt ttatagtttt agtattata g aaaattattt tgtgtattta  3180
tggatgttta tgggggtaag ggttttgtgt tgtttaattt agtattttga attgtgttg   3240 ttgaatgaat atagaattt gtttgttttg ggagagtata gaaatagtt ttttattata    3300 tattatagtt agttgtaaat agtagatggt ttttatatt ttagagagta agaattagag   3360
agagagagaa agagagagag tttgggtttt tttttttgt gtttgttttt tttagagaaa   3420 ttggagggt agtagttagt atttttttgt tggttttatt aagtatagtt aaggttttta   3480
ggatatggtt atttttttatt tgtggaagtg gttttgttgg ggtgggtggg tgttagttgg  3540
ttttggtttg ggtagagat atttagtggt ttaggtgggt gtggggttag ggtgtagatg   3600
agaaggggta tgagggtttt gttttgagga tttagtggta agtattggtt ttgggtgtgt   3660
tttagtttat ttatttgtgt gtttatggtg gtattatttt ttataaggat ttgaatgatt    3720
tgggggtggt tttgttttgt tattttttgt ttttggtttt gttttttttt tggagggttg   3780
atgaggtaat gtggttttgt tattggtttg agggggtggg ttttaatagt ttgaggtggg   3840 gttttgggg gtttagtgtt atattatttg gttgtttagg tagtggtgta gagtgggtag    3900
taggtaggtg gtgggtgttt agatggtttt ttttttttt tttgtttttt tagttttgt     3960 ttttttgttg ggaggttgtt tgttgagttt tgtgttagtg ttgaggtagt tttgttgtgt    4020
tttattttgt tttgttgggt atttggaggg tagtgtgttg gaggtaagg ttgttttgta    4080 tggtttggtg ggtgagtgag tttgggttgt agtagttttg ttggtggtgt gtatggtaat   4140
tttgagagtg tgagtagtag ttttggtagt ggtggtagta gtggtaatga tttttttggtt  4200 tgggtttatt gtgttttgg gtagttggag tttgggggat tggggtgttg aggtgtgtat    4260
atgtttgttt agttattttt aggatgtttt ttgtaatttt gatattggta agtgttttg    4320 gtgttttgtt tgagttttat gttgtagtta ggattgtagt gttgtttagg gaggtagggt   4380 gagtttatt ttttttttt gttttaggag aggggtagat ggggttgggg tggagtggag    4440
aaatttgatg ttttgggtg ggggtgttgg tatagttgag aggggaagat gttttgtaga    4500
g                                                                   4501
```

<210> SEQ ID NO 57
<211> LENGTH: 4501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 57

```
ttttgtaggg tatttttttt ttttagttat gttagtgttt ttgtttaagg atattgagtt      60
tttttatttt gttttaattt tgtttgtttt tttttggggg tagaggaaag gagtggggtt     120
tgttttgttt ttttaagtag tgttgtagtt ttggttgtag tgtggggttt gggtggggta     180
ttaggagtgt ttattgatgt tggagttgta gaaggtgttt tgggggtggt tgggtgagta     240
tgtgtatgtt ttggtgtttt agttttttag gttttagttg tttaggagta tgatgagttt     300
gagttaaggg gttattgttg ttgttgttgt tgttgttggg gttgttgttt gttttttttaa    360
agttgttgtg tgtgttgttg gtggggttgt tgtagtttga gtttgtttgt ttgttgggtt    420
gtgtgggta attttggttt ttggtgtgtt gttttttgag tgtttggtgg gatgggatgg     480
ggtgtagtga ggttgttttg gtgttggtgt aggattggt gggtggtttt ttggtgaagg      540
agtaggagtt ggaggagtaa gaggaggagg agaagttgtt tgagtgtttg ttgtttgttt     600
gttgtttgtt ttgtgttgtt gtttgggtgg ttgagtgata tagtgttggg ttttttgggga   660
ttttgttttg ggttgttggg gtttgttttt ttagattaat ggtagagttg tattattta    720
ttggtttttt aaaaagggg tggggttggg ggtaaggggt aatgggtgg ggttgttttt     780
ggattgttta gattttata gggaataatg ttgttgtggg tatgtgagtg ggtgggttgg     840
ggtgtgtttg ggattggtgt ttgttgttgg gttttttggag tggagttttt gtgtttttt    900
ttgtttgtgt tttggttta tgtttatttg ggttattggg tgttttgat ttaaattaga     960
attaattaat attatttat tttagtagga ttgttttat aggtgagggg tggttatgtt    1020
ttagagattt tgattgtgtt tggtggaatt agtgggggaa tgttaattgt tatttttta     1080
gttttttttgg agagagtagg tatagaggag aaagatttaa atttttttt ttttttttt   1140
tttttggttt ttattttttg ggatatggga agttatttgt tgtttgtagt tggttatgat   1200
atatgataga agattgtttt ttgtgtttttt tagagtaaa tggggttttg tatttattta   1260
ataaatatgg tttaggatgt tgggttaagt aatataaagt ttttgttttt gtggatattt   1320
atgaatgtat agggtgattt tttgtgatgt tagggttatg aagaaaataa aatagagttt   1380
tgggttggat atgattgggg agggtttgtt tttttgtga tagtaaggga agggtttttt    1440
gaagtgttat ttttgttgag aagtggataa agataaggat tagttttggg gtaagttata   1500
ggagagaggt attaggtagg gggaatagta agtgtaaaga ttttgggtat gtttgaaaga   1560
tagaaagtag aaaggtaaga ggaagtggtt ttttgtttat ggttgataga gttttatttt    1620
ttagtaaggg atttggggt gagttgattt aaaattgtag taaaattagg agaatgattt    1680
aggattttag atgattagtt ataatagatg attgtagata attaatataa ttattatttt   1740
tattattgat attttgattt tgttttgtat ttttaaaagt aggattttgt atttttattgt   1800
attatagttt ttataataat ttttgtgggt aggaaaagta agtataagta ttatttttat   1860
tttttagatg aggaattggt atagaaagat gggatgattg gtggttagtt aggaatttgt   1920
tattttttt tattgttttt ttttatttga agagagatat gtatttttt gaatgttagt    1980
agttgtttta tttaattgta aatggttatt tgtagttggg atttttttatt tttttatatt  2040
tttgttttttt tttttttttt ttttgtttta ttttgttaga aatgttataa gtttggaata  2100
aatagaaata gggagaaatg taagtttagt tttttttta gaattttttt gtttatattt    2160
tagataagtg atattgggat agtagaggtt gaagaatttg tgagagatgg tatttttaag   2220
```

```
aatattttg  aaattttttt  tttttttttg  agtattttag  ttataggaaa  gggaaattag   2280
tttttatatt  tttttgattt  gttttttta   tttagttta   aaaattttt   ttgttttat    2340
tttaattgtg  gtttaatttg  tagagatgtt  tttgttttt   gatgtttttt  tagtattgtt   2400
tttattgttt  tatggggtat  gattttattg  ttttttaat   tatagtagga  atattttgag   2460
gtttgggata  tttagttata  ttgtttttta  gttttttag   aattaaatag  ggttttagga   2520
gattggagag  tatgggtgtg  gttaatagtt  gattgagttt  tgagtagagt  gttttggagg   2580
ttattttaag  gatttaggtt  gaatgagggt  atatgtggtg  gaatttgaga  gatttgttta   2640
tttttgtgtt  ttatatgatt  tatttatag   ttatgtggaa  ggttttagaa  gatttttag    2700
attaaattta  ttttggataa  gtattttata  tgatagaggt  tttttttttt  tttttttttt   2760
atattttagt  tttgtttaaa  gtgttgatat  ttttttaat   ggaaggtttt  gtttggaata   2820
taagtattaa  gtagataatt  tttgttgaat  tttaagtagt  agtttttta   tagaaagtat   2880
ttgaagtgtt  tttttttagt  agttatttaa  ttatgaaagt  ataagtataa  tttgatttt    2940
tttttagttg  aaaagtaatg  aaattatttt  ttggttaatt  tttttttatt  ttttatttta   3000
agttggttta  tatagtgttt  tgaagtttag  tgaattttaa  gagtttttta  gttgggatgt   3060
tttttttat   tttaaatttg  agttagtttt  tttttgttta  ttgtgtgaag  gtagtttggt   3120
ttttatttta  aggaaaagaa  atagtaaatt  ttatgaattt  ttgtgtaggg  gagtttttt    3180
gttagggtta  ttttttttag  taggtatta   ttagttgga   tgttatggtg  tttatgagtt   3240
taataatatg  taagaattgg  ttatttaata  ttatttaata  agttaggtgg  ggtgaatttg   3300
aggttaatag  taagaatgaa  gatgtaggtt  gggtgtggtg  gtttatgttt  gtaattttag   3360
tattttgaga  ggttaaggtg  ggtggattat  gaggttagga  gattgagatt  attttggtta   3420
atatggtgaa  attttgtttg  tattaataat  ataaaaaatt  agttaggtgt  ggtggtgggt   3480
gtttgtagtt  ttagttattt  gggaggttga  ggtaggagaa  tggtgtgaat  tgggaggtg    3540
gagtttgtag  tgagttgaga  ttatgttatt  gtattttagt  ttaggtgatg  gagtgagatt   3600
ttgttttaa   aaaaaaaaaa  aaaaaaaaaa  agaatgaaga  tgtaggtttt  tttgtttttt   3660
tttgatagtt  aagaataatg  atagagttat  atatttggga  agaattgagt  aagttttaag   3720
atttatttgg  tttgtttata  tatttattag  gatgatttgg  tattttttt   tttggaattt   3780
ttttaggaaa  ggtgagttta  tatttatttt  ttttgtatta  agttatagga  tgttagagtt   3840
tgtaggaaga  gaagttgtaa  aaaggatttt  agaaattatt  tattttgtt   ttaaatgtgg   3900
gaaaaataag  gtttagagaa  gtgaaggaat  ttgtttattt  ttagggttta  gttttttaag   3960
ttgtaaggtg  tggtttatgt  ttgtattgtg  ggtttggaaa  ttttagttat  ttatagattt   4020
tgtatttgtt  tttagattt   gtagatagat  ttgtttgagt  ttttgtatag  tgtttagttt   4080
atagagaaat  tttatttata  ttgattaaat  aattttttat  tatgataata  attatttttt   4140
gagttaatta  gaagtaatat  aggtttgttt  ttttgatagg  tttatttttt  gtgtgtttat   4200
tttttttttt  ttttaaatta  ttagttaatg  tatttaaat   atattattat  aaaaaaaagt   4260
atatgaaaat  tttgttttg   ggaaatgaaa  agagagtaaa  gtggaaataa  aaaattaaaa   4320
gatttgagat  ttgtttttaa  tgttgtagaa  tagttgtgta  tttgtttgg   ttaagttatt   4380
ttgtttgttt  aggtgtttat  ttttgtgttt  attggatgaa  agatagaatt  tagtggtatt   4440
taggattttt  tttgttttaa  aaattttaag  attttatggg  gaattttgta  ggataagtga   4500
a                                                                        4501
```

-continued

<210> SEQ ID NO 58
<211> LENGTH: 3001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 58

| gaagtgttaa | tgttagattt | ttatttatta | tataagttta | tttttgtatt | agggtagtga | 60 |
| tttttttttt | tgggtgagat | tttgaaattt | gggattataa | ttttgaatta | taattataaa | 120 |
| atggtatttg | gttgtaaatt | atttttttt | ttttttgtt | ttttatagtt | gatattatgg | 180 |
| attttataa | ggatttatgt | tttttattta | ttttaatgaa | tagttgttgg | gtaataattt | 240 |
| tagaagagtt | ttaattttta | ttaggagaat | ggataaggtg | gagaagtaga | gaaaatgtaa | 300 |
| tgagtagaat | gtttaagtta | ttattttgga | attgattgaa | tataaataaa | aatgagaaag | 360 |
| atatgtaaaa | aagaagggaa | tgggtaagta | gggtgatgtt | tgggagagga | ggggttttat | 420 |
| agttatgaga | gttaattttg | taatatttta | tagggtatata | atattgtttt | ttatatattg | 480 |
| aggtagtagt | agggaaattt | tttaattatt | agaaatattg | aattttgttt | tttatttta | 540 |
| aatatttttt | ttatttagtt | tttgtttttt | tttattttg | taatttttat | tgttttaaaa | 600 |
| atgattttt | tttttttgga | agaagtaatt | ttttaaattt | agtttatata | agggatttg | 660 |
| atatgtttaa | taagttttaa | atatattgta | tttagtaata | tttattatat | gtttatttg | 720 |
| agttttgagt | aatttgtatt | ttaagtttag | ttttttattgt | tttgttttg | gtaaatttt | 780 |
| attaagtgtt | tttttttttt | aaatatatgt | atatgtttat | tagatttaa | agttttttat | 840 |
| gaatatgtaa | atttttttt | tttgaaaatt | tttgtgtgag | tggttagtag | gttaatttat | 900 |
| ttattgtaat | gtggttttgt | gttagggttt | tgttttgtg | ttgtttgtaa | gataattata | 960 |
| gatgtgattg | tattttagaa | gttttgaat | ttttaagat | agtttggttt | ataagaaaat | 1020 |
| taaaaggtgg | aggttgggtg | tggtggttta | tgtttgtaat | tttagtattt | tgggaggttg | 1080 |
| aggtgggtgg | attatttgag | gttgggagtt | tgaaattagt | ttgattaata | tggggaaatt | 1140 |
| ttgttttgt | taaaaatata | aaattagtta | ggtgtggtgg | tgtatgtttg | taatttagt | 1200 |
| tatttgggag | gttgaggtag | gagaattgtt | tgaatttggg | aggtagaggt | tgtgatgagt | 1260 |
| tgagattgtg | ttattgtatt | ttagtttggg | taataagagt | gaaattttgt | tatatatata | 1320 |
| taaatatata | tatatatata | tatatggtgt | agtttaggaa | gtaaaaaaaa | aaaaaaaaa | 1380 |
| aaaattagat | ttttttttat | attttagatt | tgaaggtata | aattttaggg | ttagggtgtt | 1440 |
| tgtttatttta | attttatatg | tatttgtagg | ttatttagta | tttaggtatt | tagtatttag | 1500 |
| gtatattgtg | gttttttatt | ttttatgata | gtagtaataa | tgttgattgg | aagtttatta | 1560 |
| ttgtgtgtta | tgggttatgg | gttatgtgtg | ttagaatttt | atgtgaaatt | aatatttaat | 1620 |
| ttttatggat | attttttgaaa | tagatgttat | agtttttatt | ttgttaatga | ggtagttgag | 1680 |
| gttttttagag | gtttaatatt | agtattatga | gttgtagtat | gtaaggtaaa | tatagttgga | 1740 |
| ggtgagtata | tatttgtttt | gtattttatg | tgtttaatta | taaggttttt | ttttttagg | 1800 |
| aaggttgttg | tttttttttgg | gatgatttgt | tagttttgag | gtatgatagt | atgggttttt | 1860 |
| agaagggtga | ttaggaggtt | tttttgtttt | tagttgttgg | tgttgttgtt | tattgtaggg | 1920 |
| tttgggttgt | gatttgtggg | gatggttttt | tgtgttttgg | tggggaggt | gggtggggag | 1980 |
| gggtggtggg | gtgttgggggt | ggggtttggg | atggttgggt | tgggagttgg | agtttatagt | 2040 |
| gggaagtggt | tgttgtttgg | gttttgtagg | gttaggtgag | gtgaggggggg | gtggggttgg | 2100 |
| gtgttatggg | aaggggaggt | tgtgtggatt | gggagttgta | ttgtgttagt | tgggttgtag | 2160 |

```
tggttgtgta ttaaggttgt gatggggttg gagatggaga aggtggatgt atagttttt    2220
atggatgatg attttatag ttattatagt ggttttgagt atgttgattt tgagaagttt    2280
gtggatttgg attaggattg ggattttat tggtttaatt tgtattttaa ggtgaagttt    2340
ggggtgggtg ggtttaagtt tttgttgagg ttgggaggtg tgggtgtttt ttagttttgt    2400
tttaatttgt tttattattg ttattgggtt ggttttgtag ggtttgagat ttgtattttt    2460
ttttggtttt atttgttatt aggttgtttg tgtagttagg aattttagt taggtttttg     2520
tgtgtttatt gtgattttaa gagaagaggt ggatgttttg gtatgttttt tttttttgtt    2580
ttttttgttt aaagtgtttt tggttttgg ggtgttaggt tggttgatag tttggggttt     2640
ttgtgttttg tttttttagt tgggtttga ggatgtgatt gtagagttgg tgattatgta     2700
ttttttgat aaagtgtgga tttgtagtta tgtttttttt gaaattagta aatatgtaat    2760
gtataagttt ttgatggtgt ttttggttat tttttggtt tttattgtgg gaattttttt    2820
tgttattttt agttgtttgt atatttggtg agatgggta tattgggtgg attggttttt     2880
tgaaatatgg gtatatttt tgttattgt tttttatttt tttttatt taggttggtg       2940
ttaggaggag gaatgtgtat tagtttttaa gtagtaggaa gaattggaag gttttgaaag    3000
g                                                                     3001

<210> SEQ ID NO 59
<211> LENGTH: 3001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 59 tttttttaagg ttttttagtt ttttttattg tttgggaatt gatgtgtgtt tttttttttg     60
atgttggttt gggataagag gagagtaggg ggtaggtggt ggagaatatg tttatgtttt    120
agaaagttgg tttatttggt gtgttttgtt ttattagatg tgtagatagt tgagggtggt    180
aaagagaatt tttgtaatga aggttagggg aatggttagg aatattgtta ggaatttgta    240
tattatgtat ttgttgattt taagagggt atggttgtag atttatattt tgttaaagga    300
gtgtgtagtt attggttttg tgattatatt tttgaagttt agttgaggag ataggatgta    360
gggattttga attgttagtt aatttgatgt tttgggaatt gggagtgttt tgggtggggg    420
aagtaggagg gaaggatgtg ttagggtgtt tgttttttt tttagggtta tggtgggtgt      480
ataggaattt ggttaagaat ttttggttat gtgggtggtt tggtgatggg tgggattggg     540
gaagggtgtg ggtttttagat tttgtgggt tgatttggta gtaatggtgg gatgggttag    600
ggtgggtta aggggtgttt gtatttttg gtttagtgg ggatttgggt ttgtttgttt       660
tgggtttat tttgagatgt gagttgagtt ggtgggatt ttggttttgg tttgagtttg     720
tgaatttttt ggggttggtg tatttgaggt tgttgtggtg gttgtaggag ttgttgttta    780
tgaagagttg tatgttgtt ttttttgttt ttagttttat tgtagtttg gtgtgtggtt     840
gttgtagttt ggttggtgtg gtgtggtttt tggtttgtgt ggttttttt tttgtagtg     900
tttggttttg ttttttttg ttttgtttag ttttgtgagg tttgggtggt ggttgttttt    960
tgttgtgggt tttagttttt agtttggttg tttttgagtt tgttttggtg tttgttgtt     1020
ttttttgtt tattttttt gttggggtgt agggaattgt tttatgagt tatagtttgg     1080
gttttgtagt gggtggtgat gttggtagtt gggatgagga gggttttttg gttattttt     1140
tgggggtttg tattgttatg tttagagtt ggtaagttgt ttagggaag ataatggttt    1200
```

-continued

```
ttttggaggg agggaattttt gtggttaggt gtatggggtg tgaagtaggt atgtgtttat    1260
ttttggttgt gtttgttttg tgtgttgtgg tttatggtgt tggtattgag tttttgggaa    1320
ttttagttgt tttgttggta aaatgggggt tgtggtattt gttttagggg tgtttgtgag    1380
aattaaatgt taattttata taaaatttta atatatatgg tttatggttt gtaatatata    1440
gtgataaatt tttaattaat gttgttgttg ttgttgtgag aggtaaggag ttataatgta    1500
tttgagtgtt aggtatttga gtgttaggtg atttgtaagt gtatgtggag ttgggtaggt    1560
gaatgttttg gttttagagt ttgtgttttt agatttgagg tgtgagggga gatttgattt    1620
tttttttttt tttttttta tttttttaaat tatattgtgt gtgtgtgtgt gtgtgtgttt    1680
gtgtgtgtgt ggtagagttt tgttttttgtt gtttaggttg gagtgtaatg gtatgattt     1740
ggtttattgt aatttttgtt ttttgggttt aagtgatttt tttgttttag ttttttgagt    1800
agttgggatt ataggtatgt attattatgt ttggttaatt ttgtatttttt agtagagatg    1860
gggttttttt atgttggtta ggttggtttt gaattttttaa ttttaggtga tttgtttgtt    1920
ttggtttttt aaagtgttgg gattgtaggt gtgagttatt gtgtttgatt tttatttttt    1980
aattttttg tgaattagat tgttttgaaa gatttaggaa tttttaagat gtagttatat     2040
ttgtgattat tttgtaggta gtatggaaat agaatttttaa tataaagtta tattgtaatg   2100
gatgaattag tttgttgatt atttatgtaa aggtttttag aagggaggag tttgtatgtt    2160
tataaagggt tttagggttt ggtagatata tatgtgtgtt tggggaggaa gggtatttag    2220
tgaaaatttg ttaaaagtaa aataatgaga attaggtttg aggtgtaggt tgtttagagt    2280
ttaaagtagg tatgtagtag gtattgttgg atatagtgta tttggagttt gttgaatata    2340
ttaaattttt ttatgtgaat tggatttgaa gaattgtttt ttttgaaaga aaaaagatta    2400
tttttgaaat agtaaaaatt atagaaataa aaaagaatag gaattgaatg agaaaaatgt    2460
ttgggggtgg gaggtaaagt ttaatatttt taataattaa aaagttttttt tgttgttatt   2520
ttagtatatg aagggtagtg ttgtaatttt ataggggtgtt atagagttga tttttatggt   2580
tatggagttt tttttttttt agatattatt ttgtttattt attttttttt ttttttatgta   2640
ttttttttat ttttatttat gtttagttaa ttttaaagtg atgatttaga tattttattt    2700
attgtattt ttttgttttt ttattttgtt tattttttttg atgagaattg gaattttttt   2760
agaattgttg tttaataatt gtttattaaa gtgaatagaa gatatgaatt tttatgggaa    2820
tttataatat taattgtgag gaatagaaaa aaaaaggaga taatttatag ttaaatatta    2880
ttttataatt ataatttaaa attataatttt tagattttaa ggtttttattt aaagaagaaa  2940
gttattgttt tagtataaga gtgggtttat gtagtgggta aaaatttgat attagtatttt   3000
t                                                                    3001
```